US006495697B1

(12) United States Patent
Tateishi et al.

(10) Patent No.: US 6,495,697 B1
(45) Date of Patent: Dec. 17, 2002

(54) SILVER HALIDE COLOR PHOTOGRAPHIC LIGHTSENSITIVE MATERIAL AND NOVEL PYRROLOTRIAZOLE COMPOUND

(75) Inventors: Keiichi Tateishi, Minami-Ashigara (JP); Hisashi Mikoshiba, Minami-Ashigara (JP); Naoto Matsuda, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/121,593

(22) Filed: Apr. 15, 2002

Related U.S. Application Data

(62) Division of application No. 09/675,213, filed on Sep. 29, 2000, now Pat. No. 6,399,291.

(30) Foreign Application Priority Data

Sep. 30, 1999 (JP) .......................................... 11-279838

(51) Int. Cl.[7] .......................................... C07D 487/04
(52) U.S. Cl. .................... 548/262.4; 544/132; 544/366; 546/199
(58) Field of Search ....................... 548/262.4; 544/132, 544/366; 546/199

(56) References Cited

U.S. PATENT DOCUMENTS 5,256,526 A 10/1993 Suzuki et al.
5,756,274 A 5/1998 Matsuda et al.
5,994,046 A 11/1999 Kawai
6,132,945 A 10/2000 Saito et al.

FOREIGN PATENT DOCUMENTS

EP 0545300 9/1993

OTHER PUBLICATIONS

Japanese patent application Kokai Publication No. 10–198009 (Partial English Translation) (Jul. 31, 1998).

*Primary Examiner*—Joseph K. McKane
*Assistant Examiner*—Rebecca Anderson
(74) *Attorney, Agent, or Firm*—Birch, Stewart, Kolasch & Birch, LLP

(57) ABSTRACT

A silver halide color photographic lightsensitive material contains a coupler represented by formula (I) below in at least one layer on a support (in this formula, X represents a hydrogen atom or a group which can split off by a coupling reaction with an oxidized form of an aromatic primary amine color developing agent, each of $R_1$ and $R_2$ represents an electron-attracting group having a Hammett's substituent constant p value of 0.20 or more, and the sum of the p values of $R_1$ and $R_2$ is 0.65 or more, and each of $G_1$ and $G_2$ represents a nitrogen atom or a substituent). A pyrrolotriazole compound represented by formula (I) below is also provided.

(I)

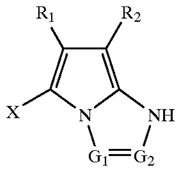

10 Claims, No Drawings

SILVER HALIDE COLOR PHOTOGRAPHIC LIGHTSENSITIVE MATERIAL AND NOVEL PYRROLOTRIAZOLE COMPOUND

This application is a divisional of application Ser. No. 09/675,213, filed on Sep. 29, 2000, now U.S. Pat. No. 6,399,241 the entire contents of which are hereby incorporated by reference and for which priority is claimed under 35 U.S.C. §120; and this application claims priority of application Ser. No. 11-279838 filed in Japan on Sep. 30, 1999 under 35 U.S.C. §119.

CROSS-REFERENCE TO RELATED APPLICATIONS

This application is based upon and claims the benefit of priority from the prior Japanese Patent Application No. 11-279838, filed Sep. 30, 1999, the entire contents of which are incorporated herein by reference.

BACKGROUND OF THE INVENTION

The present invention relates to a pyrrolotriazole compound having a specific structure and a silver halide color photographic lightsensitive material which improves the color reproduction and dye image stability, suppresses various stains, and increases the processing stability by using the pyrrolotriazole cyan coupler.

It is well known that in silver halide color photographic lightsensitive materials, an aromatic primary amine-based color developing agent oxidized by using an exposed silver halide as an oxidizer reacts with couplers to form dyes such as indophenol, indoaniline, indamine, azomethine, phenoxazine, and phenazine, thereby forming images. This photographic scheme uses subtraction color processes and forms color images by yellow, magenta, and cyan dyes.

To form a cyan dye image, a phenol- or naphthol-based coupler is conventionally used. However, dyes formed from these couplers have unpreferable absorption in regions from yellow to magenta and hence deteriorate the color reproduction. So, solving this problem has been desired.

Especially in recent years, demands on so-called digital photography are increasing by which image information is converted into digital information, image processing is performed, and after that, a silver halide color photographic lightsensitive material is exposed on the basis of the information. In this digital photography, a silver halide color photographic lightsensitive material having a wide color reproduction range, in which formed dyes have no such unpreferable absorption as described above, is desired.

Also, reversal films are desired to have high saturation and a wide color reproduction range. However, a method which emphasizes the interlayer effect has drawbacks such as deterioration of the processing dependency. Therefore, it has been required to realize high saturation and wide color reproduction by couplers superior in hue.

As means for solving this problem, heterocyclic compounds as described in, e.g., U.S. Pat. Nos. 4,728,598 and 4,873,183 and European Patent Publication No. 0249453A2 have been proposed. Unfortunately, these couplers have fatal drawbacks such as low coupling activity and low dye image stability. As couplers which have solved these problems, pyrrolotriazole couplers described in U.S. Pat. No. 5,256,526 and European Patent 0545300 have been proposed. Although these couplers are superior in hue and coupling activity, color photographic lightsensitive materials using these couplers have no sufficient dye image stability. So, the couplers must be further improved. Also, the couplers have the problem (so-called blix fading) that the color generation reduces by leuco conversion of a dye (a dye is partially decolored by reduction) during bleach-fixing. Additionally, diverse cyan stains are produced. Furthermore, conventionally known pyrrolotriazole cyan couplers produce a magenta stain with time when processed using formalin.

BRIEF SUMMARY OF THE INVENTION

It is, therefore, an object of the present invention to provide 1): a novel pyrrolotriazole compound having a specific structure, which is useful as a synthetic intermediate of coupler in a silver halide color photographic lightsensitive material and can be used as a useful intermediate of chemical, medicinal or agrichemical organic compound, and to provide 2): a silver halide color photographic lightsensitive material which improves the color reproduction and dye image stability by the use of the pyrrolotriazole cyan coupler and which reduces a cyan stain produced by the reaction with a residual color developing agent, causes blix fading little, minimizes a magenta stain, and improves the processing stability.

The present inventors extensively studied 2-position substituents and split-off groups of pyrrolotriazole-based couplers having good hue and have found that the above problems can be solved by a coupler, represented by the following formula, having an entirely new structure conventionally unknown. That is, the object of the present invention is achieved by the following means.

(1) A silver halide color photographic lightsensitive material comprising at least one layer on a support, wherein the at least one layer contains a coupler represented by formula (I) below:

(I)

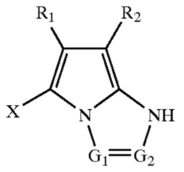

wherein X represents a hydrogen atom or a group capable of splitting off by a coupling reaction with an oxidized form of an aromatic primary amine color developing agent; each of $R_1$ and $R_2$ represents an electron-attracting group having a Hammett's substituent constant σp value of not less than 0.20, the sum of the σp values of $R_1$ and $R_2$ being not less than 0.65; and each of $G_1$ and $G_2$ represents a nitrogen atom or a substituent represented by formula (II), provided that one of $G_1$ and $G_2$ being a nitrogen atom and the other being a substituent represented by formula (II) below:

(II)

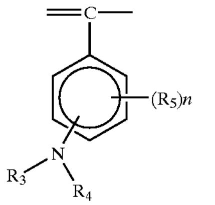

wherein $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a hydrogen atom or a substituent bonded by a carbon atom, $R_3$ and $R_4$ being capable of combining to form a ring; $R_5$ represents a substituent, and n represents an integer of 0 to 4, provided that a group represented by $R_1$, $R_2$, $R_3$, $R_4$, $R_5$, or X may be a divalent group, and thereby the coupler represented by formula (I) may form a polymer, which is a dimer or a higher-order polymer, or may form a homopolymer or a copolymer by combining with a polymeric chain.

(2) The lightsensitive material according to (1), characterized in that the coupler represented by formula (I) is represented by formula (III) below:

(III)

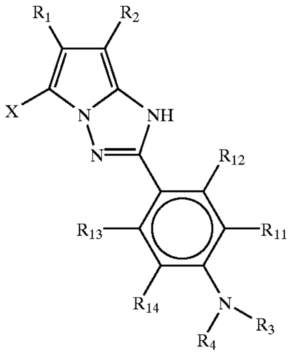

wherein X represents a hydrogen atom or a group capable of splitting off by a coupling reaction with an oxidized form of an aromatic primary amine color developing agent; each of $R_1$ and $R_2$ represents an electron-attracting group having a Hammett's substituent constant σp value of not less than 0.20, the sum of the σp values of $R_1$ and $R_2$ being not less than 0.65; $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, substituted or nonsubstituted acyl group, substituted or nonsubstituted alkyloxycarbonyl group, substituted or nonsubstituted aryloxycarbonyl group and substituted or nonsubstituted carbamoyl group, $R_3$ and $R_4$ being capable of combining to form a ring; and each of $R_{11}$ to $R_{14}$ independently represents a hydrogen atom or a substituent.

(3) A pyrrolotriazole compound represented by formula (I) below:

(I)

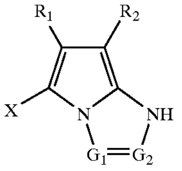

wherein X represents a member selected from the group consisting of a hydrogen atom, halogen atom, 1- to 32-carbon alkyloxy group, 6- to 32-carbon aryloxy group, 1- to 32-carbon alkylthio group, 6- to 32-carbon arylthio group, 2- to 32-carbon heterocyclic thio group, 2- to 32-carbon alkyloxycarbonyloxy group, 7- to 32-carbon aryloxycarbonyloxy group, 1- to 32-carbon carbamoyloxy group, 3- to 32-carbon heterocyclic carbonyloxy group, or 2- to 32-carbon, 5- or 6-membered nitrogen-containing heterocyclic group which bonds to a coupling active position by a nitrogen atom; each of $R_1$ and $R_2$ represents an electron-attracting group having a Hammett's substituent constant σp value of not less than 0.20, the sum of the σp values of $R_1$ and $R_2$ being not less than 0.65; and each of $G_1$ and $G_2$ represents a nitrogen atom or a substituent represented by formula (II), provided that one of $G_1$ and $G_2$ being a nitrogen atom and the other being a substituent represented by formula (II) below:

(II)

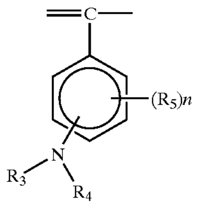

wherein $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a hydrogen atom or a substituent bonded by a carbon atom, $R_3$ and $R_4$ being capable of combining to form a ring; $R_5$ represents a substituent, and n represents an integer of 0 to 4, provided that a group represented by $R_1$, $R_2$, $R_3$, $R_4$, $R_5$, or X may be a divalent group, and thereby the coupler represented by formula (I) may form a polymer, which is a dimer or a higher-order polymer, or may form a homopolymer or a copolymer by combining with a polymeric chain.

(4) The pyrrolotriazole compound according to (3), characterized in that the compound represented by formula (I) is represented by formula (III) below:

(III)

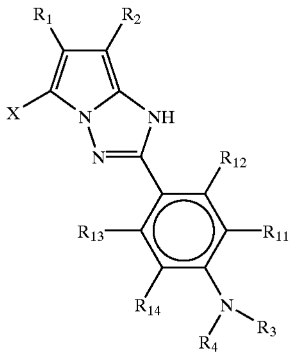

wherein X represents a member selected from the group consisting of a hydrogen atom, halogen atom, 1- to 32-carbon alkyloxy group, 6- to 32-carbon aryloxy group, 1- to 32-carbon alkylthio group, 6- to 32-carbon arylthio group, 2- to 32-carbon heterocyclic thio group, 2- to 32-carbon alkyloxycarbonyloxy group, 7- to 32-carbon aryloxycarbonyloxy group, 1- to 32-carbon carbamoyloxy group, 3- to 32-carbon heterocyclic carbonyloxy group, or 2- to 32-carbon, 5- or 6-membered nitrogen-containing heterocyclic group which bonds to a coupling active position by a nitrogen atom; each of $R_1$ and $R_2$ represents an electron-attracting group having a Hammett's substituent constant σp value of not less than 0.20, the sum of the σp values of $R_1$ and $R_2$ being not less than 0.65; $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, substituted or nonsubstituted acyl group, substituted or nonsubstituted alkyloxycarbonyl group, substituted or nonsubstituted aryloxycarbonyl group and substituted or nonsubstituted carbamoyl group, $R_3$ and $R_4$ being capable of combining to form a ring; and each of $R_{11}$ to $R_{14}$ independently represents a hydrogen atom or a substituent.

(5) The pyrrolotriazole compound according to (3), characterized in that the compound represented by formula (I) is represented by formula (IV) below:

(IV)

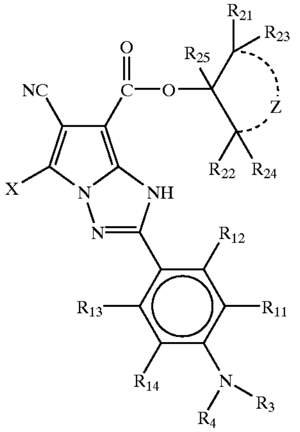

wherein X represents a member selected from the group consisting of a hydrogen atom, halogen atom, substituted or nonsubstituted alkylthio group, substituted or nonsubstituted arylthio group, substituted or nonsubstituted heterocyclic thio group, substituted or nonsubstituted alkyloxycarbonyloxy group, substituted or nonsubstituted aryloxycarbonyloxy group, substituted or nonsubstituted carbamoyloxy group, and substituted or nonsubstituted heterocyclic carbonyloxy group; $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group, $R_3$ and $R_4$ being capable of combining to form a ring; $R_{11}$ represents a member selected from the group consisting of a substituted or nonsubstituted acylamino group, substituted or nonsubstituted alkylsulfonylamino group, substituted or nonsubstituted arylsulfonylamino group, and nitro group; $R_{12}$, $R_{13}$, and $R_{14}$ can be the same or different and each represents a member selected from the group consisting of a hydrogen atom, halogen atom, alkyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group; $R_{21}$, $R_{22}$, $R_{23}$, $R_{24}$, and $R_{25}$ can be the same or different and each represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group; and Z represents a non-metallic atom group required to form a 5- to 8-membered ring, the ring being able to be substituted, be a saturated ring, or have a unsaturated bond.

(6) The lightsensitive material according to (1), characterized in that each substituent of the formula (I) is as follows:

X represents a member selected from the group consisting of a hydrogen atom, halogen atom, alkyloxy group, aryloxy group, alkylthio group, arylthio group, heterocyclic thio group, alkyloxycarbonyloxy group, aryloxycarbonyloxy group, carbamoyloxy group, heterocyclic carbonyloxy group, and 5- or 6-membered nitrogen-containing heterocyclic group which bonds to a coupling active position by a nitrogen atom; each of $R_1$ and $R_2$ represents a member selected from the group consisting of an acyl group, acyloxy group, carbamoyl group, alkyloxycarbonyl group, aryloxycarbonyl group, cyano group, nitro group, dialkylphosphono group, diarylphosphono group, diarylphosphinyl group, alkylsulfinyl group, arylsulfinyl group, alkylsulfonyl group, arylsulfonyl group, sulfonyloxy group, acylthio group, sulfamoyl group, thiocyanate group, thiocarbonyl group, alkyl halide group, alkoxy halide group, aryloxy halide group, alkylamino halide group, alkylthio halide group, aryl group which is substituted by another electron attracting group having a σp value of 0.20 or more, heterocyclic group, halogen atom, azo group, and selenocyanate group; $G_1$ and $G_2$ represent a nitrogen atom and the substituent represented by the formula (II), respectively; and each of $R_3$, $R_4$, $R_5$, and n has the same meaning as defined in (1).

(7) The lightsensitive material according to (6), characterized in that each substituent of the formula (I) is as follows:

X represents a hydrogen atom; and each of $R_1$, $R_2$, $G_1$, $G_2$, $R_3$, $R_4$, $R_5$, and n has the same meaning as defined in (6).

(8) The lightsensitive material according to (2), characterized in that each substituent of the formula (III) is as follows:

X represents a hydrogen atom; each of $R_1$ and $R_2$ represents a member selected from the group consisting of an acyl group, acyloxy group, carbamoyl group, alkyloxycarbonyl group, aryloxycarbonyl group, cyano group, nitro group, alkylsulfinyl group, arylsulfinyl group, alkylsulfonyl group, arylsulfonyl group, sulfamoyl group, alkyl halide group, alkyloxy halide group, alkylthio halide group, aryloxy halide group, aryl group substituted by two or more another electron-attracting groups having σp values of 0.20 or more, and 5- to 8-membered heterocyclic group having a nitrogen atom, oxygen atom, or sulfur atom; each of $R_{11}$, $R_{12}$, $R_{13}$, and $R_{14}$ represents a member selected from the group consisting of a hydrogen atom, halogen atom, alkyl group, alkenyl group, alkynyl group, cycloalkyl group, cycloalkenyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group; and each of $R_3$ and $R_4$ has the same meaning as defined in (2).

(9) The lightsensitive material according to (8), characterized in that each substituent of the formula (III) is as follows:

$R_3$ and $R_4$ combine to form a ring; and each of X, $R_1$, $R_2$, $R_{11}$, $R_{12}$, $R_{13}$, and $R_{14}$ has the same meaning as defined in (8).

(10) The lightsensitive material according to (1), characterized in that the coupler represented by formula (I) is represented by formula (V) below:

(V)

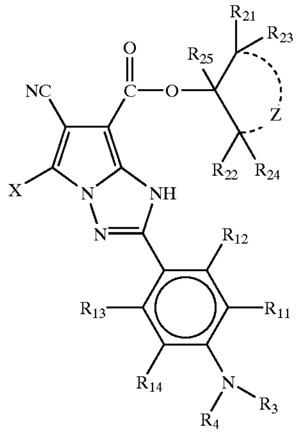

wherein X represents a member selected from the group consisting of a hydrogen atom, halogen atom, substituted or nonsubstituted alkylthio group, substituted or nonsubstituted arylthio group, substituted or nonsubstituted heterocyclic thio group, substituted or nonsubstituted alkyloxycarbonyloxy group, substituted or nonsubstituted aryloxycarbonyloxy group, substituted or nonsubstituted carbamoyloxy group, and substituted or nonsubstituted heterocyclic carbonyloxy group; $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group, $R_3$ and $R_4$ being capable of combining to form a ring; $R_{11}$ represents a member selected from the group consisting of a substituted or nonsubstituted acylamino group, substituted or nonsubstituted alkylsulfonylamino group, substituted or nonsubstituted arylsulfonylamino group, and nitro group; $R_{12}$, $R_{13}$, and $R_{14}$ can be the same or different and each represents a member selected from the group consisting of a hydrogen atom, halogen atom, alkyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group; $R_{21}$, $R_{22}$, $R_{23}$, $R_{24}$, and $R_{25}$ can be the same or different and each represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group; and Z represents a non-metallic atom group required to form a 5- to 8-membered ring, the ring being able to be substituted, be a saturated ring, or have a unsaturated bond.

(11) The lightsensitive material according to (10), characterized in that each substituent of the formula (V) is as follows:

$R_3$ and $R_4$ combine to form a ring; and each of X, $R_{11}$, $R_{12}$, $R_{13}$, $R_{14}$, $R_{21}$, $R_{22}$, $R_{23}$, $R_{24}$, and $R_{25}$ has the same meaning as defined in (10).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The present invention will be described in detail below. A Hammett's substituent constant σp value used in this specification will be briefly described below. The Hammett's rule is an empirical rule proposed in 1935 by L. P. Hammett in order to quantitatively argue the effects of substituents on reaction or equilibrium of benzene derivatives. The rule is widely regarded as appropriate in these days. The substituent constants obtained by the Hammett's rule include a σp value and σm value, and these values are described in a large number of general literature. For example, the values are described in detail in J. A. Dean ed., "Lange's Handbook of Chemistry", the 12th edition, 1979 (McGraw-Hill) and "The Extra Number of The Domain of Chemistry", Vol. 122, pp.

96 to 103, 1979 (Nanko Do), the disclosures of which are incorporated herein by reference. In the present invention, each substituent is restricted or explained by the Hammett's substituent constant σp. However, this does not mean that the present invention is limited to substituents having the already known values found in these literature. That is, the present invention includes, of course, substituents having values that fall within the above range when measured on the basis of the Hammett's rule even if they are unknown in literature. A compound represented by formula (I) or (III) of the present invention is not a benzene derivative. However, the σp value is used as a measure indicating the electron effect of a substituent, regardless of the substitution position.

In the present invention, the σp value will be used in this sense in the remainder of the text. Also, "lipophilic nature," mentioned in the present invention means that the solubility in water is 10% or less at room temperature.

In this specification, a heterocyclic ring is a ring internally having a hetero atom and can also have aromatic nature. Examples of the hetero atom are N, S, O and P. This heterocyclic ring can further have a substituent. Also, substituents mentioned in this specification and substituents which an alkyl group, alkenyl group, alkynyl group, cycloalkyl group, cycloalkenyl group, aryl group, and heterocyclic ring can have can be any substitutable groups unless specified otherwise. Examples of the substitutable groups are an alkyl group, alkenyl group, alkynyl group, cycloalkyl group, cycloalkenyl group, aryl group, heterocyclic group, acyl group, acyloxy group, acylamino group, alkyloxy group, aryloxy group, heterocyclic oxy group, alkyloxycarbonyl group, aryloxycarbonyl group, heterocyclic oxy carbonyl group, alkylcarbamoyl group, arylcarbamoyl group, alkylsulfonyl group, arylsulfonyl group, alkylsulfamoyl group, arylsulfamoyl group, alkylsulfonamide group, arylsulfonamide group, alkylamino group, arylamino group, alkylsulfinyl group, arylsulfinyl group, alkylthio group, arylthio group, mercapto group, hydroxy group, cyano group, nitro group, hydroxyamino group, and halogen atom.

A cyan coupler represented by formula (I) of the present invention will be described in detail below.

In a cyan coupler of the present invention, X represents a hydrogen atom or a group which can split off by a coupling reaction with an oxidized form of an aromatic primary amine color developing agent. Preferred examples of the group which can split off are a halogen atom, alkyloxy group, aryloxy group, acyloxy group, alkylsulfonyloxy or arylsulfonyloxy group, acylamino group, alkylsulfonamide or arylsulfonamide group, alkyloxycarbonyloxy group, aryloxycarbonyloxy group, alkylthio group, arylthio group, heterocyclic thio group, carbamoylamino group, carbamoyloxy group, heterocyclic carbonyloxy group, 5- or 6-membered nitrogen-containing heterocyclic group, imide group, and arylazo group. These groups can be further substituted by substituents enumerated for $R_1$ and $R_2$ in formula (I) to be described later.

More specifically, examples of X are a hydrogen atom, halogen atom (e.g., a fluorine atom, chlorine atom, and bromine atom), alkyloxy group (e.g., ethoxy, dodecyloxy, methoxyethylcarbamoylmethoxy, carboxypropyloxy, methanesulfonylethoxy, and ethoxycarbonylmethoxy), aryloxy group (e.g., 4-methylphenoxy, 4-chlorophenoxy, 4-methoxyphenoxy, 4-carboxyphenoxy, 3-ethoxycarbonylphenoxy, 3-acetylaminophenoxy, and 2-carboxyphenoxy), acyloxy group (e.g., acetoxy, tetradecanoyloxy, and benzoyloxy), alkylsulfonyloxy or arylsulfonyloxy group (e.g., methanesulfonyloxy and toluenesulfonyloxy), acylamino group (e.g., dichloroacetylamino and heptafluorobutyrylamino), alkylsulfonamide or arylsulfonamide group (e.g., methanesulfonylamino, trifluoromethanesulfonylamino, and p-toluenesulfonylamino), alkyloxycarbonyloxy group (e.g., ethoxycarbonyloxy and benzyloxycarbonyloxy), aryloxycarbonyloxy group (e.g., phenoxycarbonyloxy), alkylthio group, arylthio group, heterocyclic thio group (e.g., dodecylthio, 1-carboxydodecylthio, phenylthio, 2-butoxy-5-t-octylphenylthio, and tetrazolylthio), carbamoylamino group (e.g., N-methylcarbamoylamino and N-phenylcarbamoylamino), carbamoyloxy group (e.g., N,N-diethylcarbamoyloxy, N-ethylcarbamoyloxy, and N-ethyl-N-phenylcarbamoyloxy), heterocyclic carbonyloxy group (e.g., morpholinocarbonyloxy and piperidinocarbonyloxy), 5- or 6-membered nitrogen-containing heterocyclic group (e.g., imidazolyl, pyrazolyl, triazolyl, tetrazolyl, and 1,2-dihydro-2-oxo-1-pyridyl), imide group (e.g., succinimide and hydantoinyl), and arylazo group (e.g., phenylazo and 4-methoxyphenylazo). In addition, X sometimes takes the form of a bis coupler obtained by condensing a 4-equivalent coupler by aldehydes or ketones, as a split-off group bonded via a carbon atom. X can also contain photographically useful groups such as a development inhibitor and development accelerator.

X is preferably a hydrogen atom, halogen atom, 1- to 32-carbon alkyloxy group, 6- to 32-carbon aryloxy group, 1- to 32-carbon alkylthio group, 6- to 32-carbon arylthio group, 2- to 32-carbon alkyloxycarbonyloxy group, 7- to 32-carbon aryloxycarbonyloxy group, 1- to 32-carbon carbamoyloxy group, 3- to 32-carbon heterocyclic carbonyloxy group, or 2- to 32-carbon, 5- or 6-membered nitrogen-containing heterocyclic group which bonds to a coupling active position by a nitrogen atom. X is more preferably a hydrogen atom, halogen atom, alkylthio group, arylthio group, alkyloxycarbonyloxy group, aryloxycarbonyloxy group, carbamoyloxy group, or heterocyclic carbonyloxy group. X is particularly preferably a hydrogen atom, halogen atom, arylthio group, carbamoyloxy group, or heterocyclic carbonyloxy group. X is further preferably a hydrogen atom or heterocyclic carbonyloxy group, and most preferably, a hydrogen atom.

A cyan coupler of the present invention forms a cyan image because both $R_1$ and $R_2$ are electron-attracting groups having σp values of 0.20 or more and the sum of the σp values of $R_1$ and $R_2$ is 0.65 or more. The sum of the σp values of $R_1$ and $R_2$ is preferably 0.70 or more, and the upper limit is about 2.0.

Each of $R_1$ and $R_2$ is an electron-attracting group having a Hammett's substituent constant σp value of 0.20 or more, preferably 0.30 or more. The upper limit of the σp value is 1.0 or less.

Practical examples of an electron-attracting group having a σp value of 0.20 or more represented by $R_1$ and $R_2$ are an acyl group, acyloxy group, carbamoyl group, alkyloxycarbonyl group, aryloxycarbonyl group, cyano group, nitro group, dialkylphosphono group, diarylphosphono group, diarylphosphinyl group, alkylsulfinyl group, arylsulfinyl group, alkylsulfonyl group, arylsulfonyl group, sulfonyloxy group, acylthio group, sulfamoyl group, thiocyanate group, thiocarbonyl group, alkyl halide group, alkoxy halide group, aryloxy halide group, alkylamino halide group, alkylthio halide group, aryl group which is substituted by another electron attracting group having a σp value of 0.20 or more, heterocyclic group, halogen atom, azo group, and selenocyanate group.

Of groups represented by $R_1$ and $R_2$, those which can further have substituents can further have substituents such as a halogen atom, alkyl group, alkenyl group, alkynyl group, cycloalkyl group, cycloalkenyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group.

More specific examples of substituents of $R_1$ and $R_2$ are a halogen atom (e.g., a chlorine atom and bromine atom), alkyl group, alkenyl group, alkynyl group, cycloalkyl group, cycloalkenyl group (e.g., a 1- to 32-carbon, straight-chain or branched-chain alkyl group, 7- to 38-carbon aralkyl group, 2- to 32-carbon alkenyl group, 2- to 32-carbon, straight-chain or branched chain alkynyl group, 3- to 32-carbon, straight-chain or branched-chain cycloalkyl group, and 3- to 32-carbon, straight-chain or branched-chain cycloalkenyl group; more specifically, methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecaneamido}phenyl}propyl, 2-ethoxytridecyl, trifluoromethyl, cyclopentyl, and 3-(2,4-di-t-amylphenoxy)propyl), aryl group (e.g., phenyl, 4-t-butylphenyl, 2,4-di-t-amylphenyl, and 4-tetradecaneamidophenyl), heterocyclic group (e.g., imidazolyl, pyrazolyl, triazolyl, 2-furyl, 2-thienyl, 2-pyrimidinyl, and 2-benzothiazolyl), cyano group, hydroxy group, nitro group, carboxy group, sulfo group, amino group, alkyloxy group (e.g., methoxy, ethoxy, 2-methoxyethoxy, 2-dodecylethoxy, and 2-methanesulfonylethoxy), aryloxy group (e.g., phenoxy, 2-methylphenoxy, 4-t-butylphenoxy, 3-nitrophenoxy, 3-t-butyloxycarbamoylphenoxy, and 3-methoxycarbamoyl), acylamino group (e.g., acetamide, benzamide, tetradecaneamide, 2-(2,4-di-t-amylphenoxy)butaneamide, 4-(3-t-butyl-4-hydroxyphenoxy)butaneamide, and 2-{4-(4-hydroxyphenylsulfonyl)phenoxy}decaneamide), alkylamino group (e.g., methylamino, butylamino, dodecylamino, diethylamino, and methylbutylamino), anilino group (e.g., phenylamino, 2-chloroanilino, 2-chloro-5-tetradecaneaminoanilino, 2-chloro-5-dodecyloxycarbonylanilino, N-acetylanilino, 2-chloro-5-{2-(3-t-butyl-4-hydroxyphenoxy)dodecaneamido}anilino), ureido group (e.g., phenylureido, methylureido, and N,N-dibutylureido), sulfamoylamino group (e.g., N,N-dipropylsulfamoylamino and N-methyl-N-decylsulfamoylamino), alkylthio group (e.g., methylthio, octylthio, tetradecylthio, 2-phenoxyethylthio, 3-phenoxypropylthio, and 3-(4-t-butylphenoxy)propylthio), arylthio group (e.g., phenylthio, 2-butoxy-5-t-octylphenylthio, 3-pentadecylphenylthio, 2-carboxyphenylthio, and 4-tetradecaneamidophenylthio), alkyloxycarbonylamino group (e.g., methoxycarbonylamino and tetradecyloxycarbonylamino), sulfonamide group (e.g., methanesulfonamide, hexadecanesulfonamide, benzenesulfonamide, p-toluenesulfonamide, octadecanesulfonamide, and 2-methoxy-5-t-butylbenzenesulfonamide), carbamoyl group (e.g., N-ethylcarbamoyl, N,N-dibutylcarbamoyl, N-(2-dodecyloxyethyl)carbamoyl, N-methyl-N-dodecylcarbamoyl, and N-{3-(2,4-di-t-amylphenoxy)propyl}carbamoyl), sulfamoyl group (e.g., N-ethylsulfamoyl, N,N-dipropylsulfamoyl, N-(2-dodecyloxyethyl)sulfamoyl, N-ethyl-N-dodecylsulfamoyl, and N,N-diethylsulfamoyl), sulfonyl group (e.g., methanesulfonyl, octanesulfonyl, benzenesulfonyl, and toluenesulfonyl), alkyloxycarbonyl group (e.g., methoxycarbonyl, butyloxycarbonyl, dodecyloxycarbonyl, and octadecyloxycarbonyl), heterocyclic oxy group (e.g., 1-phenyltetrazole-5-oxy and 2-tetrahydropyranyloxy), azo group (e.g., phenylazo, 4-methoxyphenylazo, 4-pivaloylaminophenylazo, and 2-hydroxy-4-propanoylphenylazo), acyloxy group (e.g., acetoxy), carbamoyloxy group (e.g., N-methylcarbamoyloxy and N-phenylcarbamoyloxy), silyloxy group (e.g., trimethylsilyloxy and dibutylmethylsilyloxy), aryloxycarbonylamino group (e.g., phenoxycarbonylamino), imide group (e.g., N-succinimide, N-phthalimide, and 3-octadecenylsuccinimide), heterocyclic thio group (e.g., 2-benzothiazolylthio, 2,4-di-phenoxy-1,3,5-triazole-6-thio, and 2-pyridylthio), sulfinyl group (e.g., dodecanesulfinyl, 3-pentadecylphenylsulfinyl, and 3-phenoxypropylsulfinyl), phosphonyl group (e.g., phenoxyphosphonyl, octyloxyphosphonyl, and phenylphosphonyl), aryloxycarbonyl group (e.g., phenoxycarbonyl), and acyl group (e.g., acetyl, 3-phenylpropanoyl, benzoyl, and 4-dodecyloxybenzoyl).

Note that in each of $R_1$ and $R_2$, alkyl of a group having an alkyl portion means straight-chain or branched-chain alkyl or cycloalkyl. Note also that substituted alkyl groups include aralkyl, alkenyl, alkynyl, and cycloalkenyl.

Accordingly, an alkyloxycarbonyl group includes a straight-chain or branched-chain alkyloxycarbonyl group, aralkyloxycarbonyl group, alkenyloxycarbonyl group, alkynyloxycarbonyl group, cycloalkyloxycarbonyl group, and cycloalkenoxycarbonyl group.

$R_1$ and $R_2$ will be described in more detail below. Examples of an electron-attracting group having a $\sigma p$ value of 0.20 or more are an acyl group (e.g., acetyl, 3-phenylpropanoyl, benzoyl, and 4-dodecyloxybenzoyl), acyloxy group (e.g., acetoxy), carbamoyl group (e.g., carbamoyl, N-ethylcarbamoyl, N-phenylcarbamoyl, N,N-dibutylcarbamoyl, N-(2-dodecyloxyethyl)carbamoyl, N-(4-n-pentadecaneamido)phenylcarbamoyl, N-methyl-N-dodecylcarbamoyl, and N-{3-(2,4-di-t-amylphenoxy)propyl}carbamoyl), alkyloxycarbonyl group (e.g., methoxycarbonyl, ethoxycarbonyl, iso-propyloxycarbonyl, tert-butyloxycarbonyl, iso-butyloxycarbonyl, butyloxycarbonyl, dodecyloxycarbonyl, octadecyloxycarbonyl, cyclohexyloxycarbonyl, and cyclohexenoxycarbonyl), aryloxycarbonyl group (e.g., phenoxycarbonyl), cyano group, nitro group, dialkylphosphono group (e.g., dimethylphosphono), diarylphosphono group (e.g., diphenylphosphono), diarylphosphinyl group (e.g., diphenylphosphinyl), alkylsulfinyl group (e.g., 3-phenoxypropylsulfinyl), arylsulfinyl group (e.g., 3-pentadecylphenylsulfinyl), alkylsulfonyl group (e.g., methanesulfonyl and octanesulfonyl), arylsulfonyl group (e.g., benzenesulfonyl and toluenesulfonyl), sulfonyloxy group (methanesulfonyloxy and toluenesulfonyloxy), acylthio group (e.g., acetylthio and benzoylthio), sulfamoyl group (e.g., N-ethylsulfamoyl, N,N-dipropylsulfamoyl, N-(2-dodecyloxyethyl)sulfamoyl, N-ethyl-N-dodecylsulfamoyl, and N,N-diethylsulfamoyl), thiocyanate group, thiocarbonyl group (e.g., methylthiocarbonyl and phenylthiocarbonyl), alkyl halide group (e.g., trifluoromethane and heptafluoropropane), alkyloxy halide group (e.g., trifluoromethyloxy), aryloxy halide group (e.g., pentafluorophenyloxy), alkylamino halide group (e.g., N,N-di-(trifluoromethyl)amino), alkylthio halide group (e.g., difluoromethylthio and 1,1,2,2-tetrafluoroethylthio), aryl group which is substituted by another electron-attracting group having a σp value of 0.20 or more (e.g., 2,4-dinitrophenyl, 2,4,6-trichlorophenyl, and pentachlorophenyl), heterocyclic group (e.g., 2-benzoxazolyl, 2-benzothiazolyl, 1-phenyl-2-benzimidazolyl, 5-chloro-1-tetrazolyl, and 1-pyrrolyl), halogen atom (e.g., chlorine atom and bromine atom), azo group (e.g., phenylazo), and selenocyanate group.

Of these substituents, those which can further have substituents can further have substituents as described above.

Preferred examples of $R_1$ and $R_2$ are a 2- to 32-carbon acyl group, 2- to 32-carbon acyloxy group, 1- to 32-carbon carbamoyl group, 2- to 32-carbon alkyloxycarbonyl group, 7- to 32-carbon aryloxycarbonyl group, cyano group, nitro group, 1- to 32-carbon alkylsulfinyl group, 6- to 32-carbon arylsulfinyl group, 1- to 32-carbon alkylsulfonyl group, 6- to 32-carbon arylsulfonyl group, 0- to 32-carbon sulfamoyl group, 1- to 32-carbon alkyl halide group, 1- to 32-carbon alkyloxy halide group, 1- to 32-carbon alkylthio halide group, 7- to 32-carbon aryloxy halide group, 7- to 32-carbon aryl group substituted by two or more another electron-attracting groups having σp values of 0.20 or more, and 5- to 8-membered, 1- to 36-carbon heterocyclic group having a nitrogen atom, oxygen atom, or sulfur atom.

More Preferred examples of $R_1$ and $R_2$ are 2- to 32-carbon alkyloxycarbonyl group, nitro group, cyano group, 6- to 32-carbon arylsulfonyl group, 1- to 32-carbon carbamoyl group, and 1- to 32-carbon alkyl halide group. $R_1$ is most preferably a cyano group. $R_2$ is particularly preferably a 2- to 32-carbon alkyloxycarbonyl group, and most preferably, a branched 4- to 32-carbon alkyloxycarbonyl group (particularly a cycloalkyloxycarbonyl group).

In a cyan coupler of the present invention, each of $G_1$ and $G_2$ represents a nitrogen atom or a substituent represented by formula (II). One of $G_1$ and $G_2$ is a nitrogen atom, and the other is a substituent represented by formula (II).

(II)

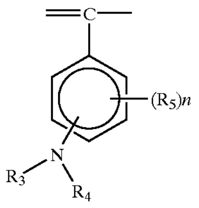

In formula (II), $R_3$ represents a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, or substituted or nonsubstituted heterocyclic group, and $R_4$ represents a hydrogen atom or a substituent bonded by a carbon atom. $R_5$ represents a substituent. n represents an integer of 0 to 4.

More specifically, an alkyl group, alkenyl group, alkynyl group, cycloalkyl group, and cycloalkenyl group represented by $R_3$ are a 1- to 32-carbon, straight-chain or branched-chain alkyl group, 7- to 32-carbon aralkyl group, 2- to 32-carbon alkenyl group, 2- to 32-carbon alkynyl group, 3- to 32-carbon cycloalkyl group, and 3- to 32-carbon cycloalkenyl group. Practical examples are methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecaneamido}phenyl}propyl, 2-ethoxytridecyl, trifluoromethyl, cyclopentyl, and 3-(2,4-di-t-amylphenoxy)propyl). An aryl group represented by $R_3$ is preferably a 6- to 36-carbon aryl group, and-a monocyclic group is more preferable. Practical examples are phenyl, 4-t-butylphenyl, 2-methylphenyl, 2,4,6-trimethylphenyl, 2-methoxyphenyl, 4-methoxyphenyl, 2,6-dichlorophenyl, 2-chlorophenyl, and 2,4-dichlorophenyl. A heterocyclic group represented by $R_3$ is preferably a 5- to 8-membered, 1- to 36-carbon heterocyclic group having a nitrogen atom, oxygen atom, or sulfur atom. A heterocyclic group is more preferably a 5- or 6-membered ring bonded by a nitrogen atom. These rings can also form a condensed ring together with a benzene ring or a hetero ring. Practical examples are imidazolyl, pyrazolyl, triazolyl, piperidino, pyrrolidyl, pyrrolyl, morpholino, pyrazolidyl, and thiazolidyl, and pyrrolidyl is preferable.

Of these substituents, those which can further have substituents can be further substituted by substituents enumerated for $R_1$ and $R_2$ described above.

Preferred examples of $R_3$ are a substituted or nonsubstituted alkyl group, substituted or nonsubstituted alkenyl group, substituted or nonsubstituted alkynyl group, substituted or nonsubstituted cycloalkyl group, and substituted or nonsubstituted cycloalkenyl group.

$R_4$ represents a hydrogen atom or a substituent bonded by a carbon atom. Examples of the substituent bonded by a carbon atom are a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, substituted or nonsubstituted acyl group, substituted or nonsubstituted alkyloxycarbonyl group, substituted or nonsubstituted aryloxycarbonyl group, and substituted or nonsubstituted carbamoyl group.

More specifically, a hydrogen atom, alkyl group, alkenyl group, alkynyl group, cycloalkyl group, and cycloalkenyl group represented by $R_4$ are a 1- to 32-carbon, straight-chain or branched-chain alkyl group, 7- to 32-carbon aralkyl group, 2- to 32-carbon alkenyl group, 2- to 32-carbon alkynyl group, 3- to 32-carbon cycloalkyl group, and 3- to 32-carbon cycloalkenyl group. Practical examples are methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecaneamido}phenyl}propyl, 2-ethoxytridecyl, trifluoromethyl, cyclopentyl, and 3-(2,4-di-t-amylphenoxy)propyl). An aryl group represented by $R_4$ is preferably a 6- to 36-carbon aryl group, and a monocyclic group is more preferable. Practical examples are phenyl, 4-t-butylphenyl, 2-methylphenyl, 2,4,6-trimethylphenyl, 2-methoxyphenyl, 4-methoxyphenyl, 2,6-dichlorophenyl, 2-chlorophenyl, and 2,4-dichlorophenyl. An acyl group represented by $R_4$ is preferably a 2- to 32-carbon acyl group. Practical examples are acetyl, pivaloyl, octanoyl, and benzoyl. Examples of an alkyloxycarbonyl group, aryloxycarbonyl group, and carbamoyl group are those described above as groups which substitute $R_1$ and $R_2$.

Of these substituents, those which can further have substituents can be further substituted by substituents enumerated as groups which substitute $R_1$ and $R_2$ described above.

Preferred examples of $R_4$ are a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group.

$R_3$ and $R_4$ can combine to form a 5- or 6-membered ring bonded by a nitrogen atom. Practical examples are imidazolyl, pyrazolyl, triazolyl, piperidyl, piperidino, pyrrolidinyl, pyrrolyl, morpholyl, morpholino, pyrazolidinyl, thiazolidinyl, pyrazolinyl, and piperadinyl. These rings can form a condensed ring together with a benzene ring or a hetero ring.

As $R_3$ and $R_4$, substituents which form a ring structure are preferred to those which do not. Of these substituents, groups forming a 6-membered ring bonded by a nitrogen atom are preferable. Of these groups, morpholino, piperadinyl substituted by an acyl group, piperidino, and piperidino substituted by a carboxyl group are preferable.

Examples of $R_5$ are a halogen atom, alkyl group, alkenyl group, alkynyl group, cycloalkyl group, cycloalkenyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group.

Practical examples of $R_5$ are groups described above as groups which substitute $R_1$ and $R_2$.

Of these substituents, those which can further have substituents can be further substituted by substituents enumerated as groups which substitute $R_1$ and $R_2$ described above.

Preferred examples of $R_5$ are an alkyl group, alkenyl group, alkynyl group, cycloalkyl group, cycloalkenyl group, aryl group, heterocyclic group, cyano group, nitro group, acylamino group, anilino group, ureido group, sulfamoylamino group, alkylthio group, arylthio group, alkyloxycarbonylamino group, sulfonamide group (alkylsulfonylamino group and arylsulfonylamino group), carbamoyl group, sulfamoyl group, sulfonyl group, alkyloxycarbonyl group, heterocyclic oxy group, acyloxy group, carbamoyloxy group, aryloxycarbonylamino group, imide group, heterocyclic thio group, sulfinyl group, phosphonyl group, aryloxycarbonyl group, and acyl group.

$R_5$ is more preferably a nitro group (particularly useful as intermediate of coupler in a silver halide color photographic lightsensitive material), substituted or nonsubstituted, 2- to 32-carbon acylamino group, substituted or nonsubstituted, 1 to 32-carbon alkylsulfonylamino group, or substituted or nonsubstituted, 6- to 40-carbon arylsulfonylamino group. $R_5$ is most preferably a nitro group or a 6- to 40-carbon arylsulfonylamino group having a substituent. The substituent, which the arylsulfonylamino group has, is preferably a 1- to 32-carbon alkoxy group, 1- to 32-carbon alkyl group, 1- to 32-carbon sulfonylamino group, 1- to 32-carbon acylamino group, or halogen atom.

n is an integer of 0 to 4, preferably 1 or 2, and most preferably, 1.

In a cyan coupler represented by formula (I), a group represented by $R_1$, $R_2$, $R_3$, $R_4$, $R_5$, or X can be a divalent group, and thereby the coupler represented by formula (I) can form a polymer, which is a dimer or a higher-order polymer, or can form a homopolymer or a copolymer by combining with a polymeric chain. In the case of forming a polymer, monomer, that is, the coupler represented by formula (I) can be the same or different. In the case of forming a homopolymer or a copolymer by combining with a polymeric chain, its typical example is a homopolymer or copolymer of an addition polymer ethylene type unsaturated compound having a cyan coupler moiety represented by formula (I). When this is the case, one or more types of cyan color-forming repeating units having a cyan coupler moiety represented by formula (I) can be contained in the polymer. Alternatively, the polymer can be a copolymer containing one or more types of non-color-forming ethylene type monomers as copolymerization components. The number of the cyan color-forming repeating unit having a cyan coupler moiety represented by formula (I) is preferably 3 to 1,000, and more preferably, 10 to 100. The unit is more specifically represented by formula (P) below.

(P)

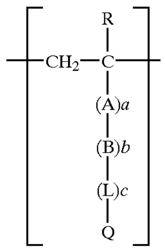

In formula (P), R represents a hydrogen atom, 1- to 4-carbon alkyl group, or chlorine atom, A represents —CONH—, —COO—, or a substituted or non-substituted phenylene group, B represents a substituted or nonsubstituted alkylene group, phenylene group, or aralkylene group, and L represents —CONH—, —NHCONH—, —NHCOO—, —NHCO—, —OCONH—, —NH—, —COO—, —OCO—, —CO—, —O—, —S—, $—SO_2—$, $—NHSO_2—$, or $—SO_2NH—$. Each of a, b, and c represents 0 or 1. Q represents a cyan coupler moiety in which a hydrogen atom splits off from $R_1$, $R_2$, $R_3$, $R_4$, $R_{11}$ to $R_{14}$, or X in a compound represented by formula (III). A polymer is preferably a copolymer of a cyan-forming monomer represented by a coupler unit of formula (III) and a non-color-forming, ethylene-type monomer which does not couple with an oxidation product of an aromatic primary amine developing agent.

Examples of the non-color-forming, ethylene-type monomer which does not couple with an oxidation product of an aromatic primary amine developing agent are acrylic acid, α-chloroacrylic acid, α-alkylacrylic acid (e.g., methacrylic acid), amide or ester derived from these acrylic acids (e.g., acrylamide, methacrylamide, n-butylacrylamide, t-butylacrylamide, diacetoneacrylamide, methylacrylate, ethylacrylate, n-propylacrylate, n-butylacrylate, t-butylacrylate, iso-butylacrylate, 2-ethylhexylacrylate, n-octylacrylate, laurylacrylate, methylmethacrylate, ethylmethacrylate, n-butylmethacrylate, and β-hydroxymethacrylate), vinyl ester (e.g., vinyl acetate, vinyl propionate, and vinyl laurate), acrylonitrile, methacrylonitrile, an aromatic vinyl compound (e.g., styrene and its derivative such as vinyltoluene, divinylbenzene, vinylacetophenone, and sulfostyrene), itaconic acid, citraconic acid, crotonic acid, vinylidene chloride, vinyl alkyl ether (e.g., vinyl ethyl ether), maleic ester, N-vinyl-2-pyrrolidone, N-vinylpyridine, and 2- and 4-vinylpyridine.

Acrylic ester, methacrylic ester, and maleic ester are particularly preferable. Two or more types of these non-color-forming, ethylene type monomers can be used together. For example, it is possible to use methylacrylate and butylacrylate, butylacrylate and styrene, butylmethacrylate and methacrylic acid, and methylacrylate and diacetoneacrylamide.

As is well known in the field of polymer couplers, an ethylene-based unsaturated monomer to be copolymerized with a vinyl-based monomer corresponding to formula (I) described above can be so selected as to have good effects on the physical properties and/or chemical properties of a copolymer formed, e.g., the solubility, the compatibility with a binder, such as gelatin, of a photographic colloid composition, the flexibility, and the thermal stability.

To make a silver halide photosensitive material, preferably a red-sensitive silver halide emulsion layer to contain a cyan coupler of the present invention, the use of a so-called incorporated coupler is preferable. For this purpose, at least one group of $R_1$, $R_2$, $R_3$, $R_4$, $R_5$, and X is preferably a so-called ballast group (having a total number of carbon atoms of preferably 10 or more). The total number of carbon atoms of the ballast group is more preferably 10 to 50. Particularly preferably, $R_3$, $R_4$, and $R_5$ have a ballast group.

An especially favorable combination as a cyan coupler represented by formula (I) of the present invention is that x is a hydrogen atom, $R_1$ is a cyano group, $R_2$ is a branched 4- to 32-carbon alkyloxycarbonyl group, $G_1$ is a nitrogen atom, $R_3$ and $R_4$ form a ring structure, preferably 6-membered heterocyclic ring, and $R_5$ is a nitro group, substituted or nonsubstituted, 2- to 32-carbon acylamino group, substituted or nonsubstituted, 1- to 32-carbon alkylsulfonylamino group, or substituted or nonsubstituted, 6- to 40-carbon arylsulfonylamino group. n is particularly preferably 1.

The most favorable combination as a cyan coupler represented by formula (I) of the present invention is that X is a hydrogen atom, $R_1$ is a cyano group, $R_2$ is a 6- to 32-carbon cycloalkyloxycarbonyl group, $G_1$ is a nitrogen atom, $R_3$ and $R_4$ form a ring structure, preferably 6-membered heterocyclic ring, and $R_5$ is a nitro group or a substituted or nonsubstituted, 6- to 40-carbon arylsulfonylamino group. n is particularly preferably 1.

Of couplers represented by formula (I), a coupler having a structure represented by formula (III) is preferable.

(III)

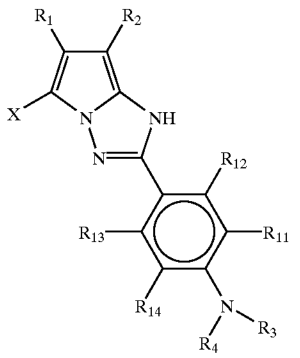

A cyan coupler represented by formula (III) of the present invention will be described in detail below. In formula (III), X, $R_1$, $R_2$, $R_3$, and $R_4$ have the same meanings as X, $R_1$, $R_2$, $R_3$, and $R_4$ in formula (I) described above, and preferred examples of these X, $R_1$, $R_2$, $R_3$, and $R_4$ are also the same.

Each of $R_{11}$ to $R_{14}$ represents a hydrogen atom or a substituent. Examples of the substituent are a halogen atom, alkyl group, alkenyl group, alkynyl group, cycloalkyl group, cycloalkenyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group.

Practical examples of $R_{11}$ to $R_{14}$ are groups enumerated above as groups which substitute $R_1$ and $R_2$ in formula (I) described above.

Preferred examples of $R_{11}$ to $R_{14}$ are a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, substituted or nonsubstituted heterocyclic group, cyano group, nitro group, substituted or nonsubstituted acylamino group, substituted or nonsubstituted anilino group, substituted or nonsubstituted ureido group, substituted or nonsubstituted sulfamoylamino group, substituted or nonsubstituted alkylthio group, substituted or nonsubstituted arylthio group, substituted or nonsubstituted alkyloxycarbonylamino group, substituted or nonsubstituted sulfonamide group (alkylsulfonylamino group and arylsulfonylamino group), substituted or nonsubstituted carbamoyl group, substituted or nonsubstituted sulfamoyl group, substituted or nonsubstituted sulfonyl group, substituted or nonsubstituted alkyloxycarbonyl group, substituted or nonsubstituted heterocyclic oxy group, substituted or nonsubstituted acyloxy group, substituted or nonsubstituted carbamoyloxy group, substituted or nonsubstituted aryloxycarbonylamino group, substituted or nonsubstituted imide group, substituted or nonsubstituted heterocyclic thio group, substituted or nonsubstituted sulfinyl group, substituted or nonsubstituted phosphonyl group, substituted or nonsubstituted aryloxycarbonyl group, and substituted or nonsubstituted acyl group.

$R_{11}$ is more preferably a nitro group (particularly useful as intermediate of coupler in a silver halide color photographic lightsensitive material), substituted or nonsubstituted, 2- to 32-carbon acylamino group, substituted or nonsubstituted, 1 to 32-carbon alkylsulfonylamino group, or substituted or nonsubstituted, 6- to 40-carbon arylsulfonylamino group. $R_{11}$ is most preferably a nitro group or a 6- to 40-carbon arylsulfonylamino group having a substituent. The substituent, which the arylsulfonylamino group has, is preferably a 1- to 32-carbon alkoxy group, 1- to 32-carbon alkyl group, 1- to 32-carbon sulfonylamino group, 1- to 32-carbon acylamino group, or halogen atom.

Each of $R_{12}$ to $R_{14}$ is preferably a hydrogen atom or a 6- to 40-carbon arylsulfonylamino group having a substituent, and most preferably, a hydrogen atom.

A particularly favorable combination as a cyan coupler represented by formula (III) of the present invention is that X is a hydrogen atom, $R_1$ is a cyano group, $R_2$ is a branched 4- to 32-carbon alkyloxycarbonyl group, $R_3$ and $R_4$ form a ring structure, preferably 6-membered heterocyclic ring, and $R_{11}$ is a substituted or nonsubstituted, 2- to 32-carbon acylamino group, substituted or nonsubstituted, 1- to 32-carbon alkylsulfonylamino group, substituted or nonsubstituted, 6- to 40-carbon arylsulfonylamino group, or nitro group. Each of $R_{12}$ to $R_{14}$ is a hydrogen atom or a 6- to 32-carbon arylsulfonylamino group having a substituent. The substituent, which the arylsulfonylamino group has, is preferably a 1- to 32-carbon alkoxy group, 1- to 32-carbon alkyl group, 1- to 32-carbon sulfonylamino group, 1- to 32-carbon acylamino group, or halogen atom.

A cyan coupler represented by formula (III) is more preferably a structure represented by formula (V) below.

(V)

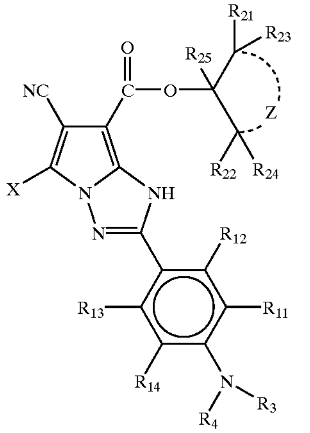

In formula (V), X, $R_3$, $R_4$, $R_{11}$, $R_{12}$, $R_{13}$, and $R_{14}$ have the same meanings as X, $R_3$, $R_4$, $R_{11}$, $R_{12}$, $R_{13}$, and $R_{14}$ in formula (III).

$R_{21}$, $R_{22}$, $R_{23}$, $R_{24}$, and $R_{25}$ can be the same or different and each represents a hydrogen atom or a substituent. Preferred examples of the substituent are a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group. More preferred examples are as follows.

Each of $R_{21}$ and $R_{22}$ represents preferably an alkyl group, alkenyl group, alkynyl group, cycloalkyl group, or cycloalkenyl group. Examples are a 1- to 36-carbon, straight-chain, branched-chain, or cyclic alkyl group, 7- to 36-carbon aralkyl group, 2- to 36-carbon alkenyl group, 2- to 36-carbon alkynyl group, and 3- to 36-carbon cycloalkenyl group, and more specifically, methyl, ethyl, propyl, isopropyl, t-butyl, t-amyl, t-octyl, tridecyl, cyclopentyl, and cyclohexyl. The upper limit of the number of carbon atoms of an alkyl group, alkenyl group, alkynyl group, cycloalkyl group, and cycloalkenyl group is more preferably 12. Each of $R_{21}$ and $R_{22}$ is further preferably a nonsubstituted 1- to 8-carbon alkyl group. Each of $R_{23}$, $R_{24}$, and $R_{25}$ represents a hydrogen atom, alkyl group, alkenyl group, alkynyl group, cycloalkyl group, or cycloalkenyl group. Examples of the alkyl group, alkenyl group, alkynyl group, cycloalkyl group, and cycloalkenyl group are groups previously enumerated as $R_{21}$ and $R_{22}$. Each of $R_{23}$, $R_{24}$, and $R_{25}$ is particularly preferably a hydrogen atom.

Z represents a non-metallic atomic group required to form a 5- to 8-membered ring. This ring can be substituted, can be a saturated ring, or can have an unsaturated bond. A non-metallic atom is preferably a nitrogen atom, oxygen atom, sulfur atom, or carbon atom, and more preferably, a carbon atom.

Examples of a ring formed by Z are a cyclopentane ring, cyclohexane ring, cycloheptane ring, cyclooctane ring, cyclohexene ring, piperazine ring, oxane ring, and thiane ring. These rings can be substituted by the substituents described above.

A ring formed by Z is preferably a cyclohexane ring which can be substituted, and particularly preferably, a cyclohexane ring whose 4-position is substituted by a 1- to 24-carbon alkyl group (which can be substituted by the aforementioned substituents).

A cyan coupler represented by formula (V) used in the present invention has an oil-soluble group in its molecules and hence is readily soluble in a high-boiling organic solvent. Preferably, this coupler itself and a dye formed by oxidation coupling of the coupler with a color formation reducing agent (developing agent) are nondiffusible in a hydrophilic colloid layer.

A particularly favorable combination as a cyan coupler represented by formula (V) of the present invention is that X is a hydrogen atom, each of $R_{21}$ and $R_{22}$ is t-butyl, each of $R_{23}$, $R_{24}$, and $R_{25}$ is a hydrogen atom, Z forms a cyclohexane ring, the 4-position of this cyclohexane ring is substituted by a 1- to 8-carbon alkyl group, $R_3$ and $R_4$ form a ring structure (preferably a group which forms a 6-membered ring bonded by a nitrogen atom, e.g., morpholino, piperadinyl substituted by an acyl group, or piperidino substituted by a carboxyl group), $R_{11}$ is a substituted or nonsubstituted, 1- to 32-carbon alkylsulfonylamino group, substituted or nonsubstituted, 6- to 30-carbon arylsulfonylamino group, or nitro group, and each of $R_{12}$ to $R_{14}$ is a hydrogen atom or a 6- to 30-carbon arylsulfonylamino group having a substituent. The substituent, which the arylsulfonylamino group has, is preferably a 1- to 32-carbon alkoxy group, 1- to 32-carbon alkyl group, 1- to 32-carbon sulfonylamino group, 1- to 32-carbon acylamino group, or halogen atom.

A pyrrolotriazole compound represented by formula (I), (III), and (IV) of the present invention will be described in detail below. Note that compounds represented by formulas (I), (III), and (IV) have conventionally unknown novel structures, are useful as synthetic intermediates of couplers in silver halide color photographic lightsensitive material, and can be used as useful intermediates of chemical, medicinal or agrichemical organic compounds.

Each substituent of formula (I) of the pyrrolotriazole compound represented by formula (I) has the same meaning as that of a cyan coupler represented by formula (I) for use in the silver halide color photographic lightsensitive material mentioned above, with the exception of the definition of X. Also, each substituent of formula (III) of the pyrrolotriazole compound represented by formula (III) has the same meaning as that of a cyan coupler represented by formula (III) for use in the silver halide color photographic lightsensitive material mentioned above, with the exception of the definition of X. Specifically, in the pyrrolotriazole compound represented by formula (I) and (III), X represents a hydrogen atom, halogen atom, 1- to 32-carbon alkyloxy group, 6- to 32-carbon aryloxy group, 1- to 32-carbon alkylthio group, 6- to 32-carbon arylthio group, 2- to 32-carbon alkyloxycarbonyloxy group, 7- to 32-carbon aryloxycarbonyloxy group, 1- to 32-carbon carbamoyloxy group, 3- to 32-carbon heterocyclic carbonyloxy group, or 2- to 32-carbon, 5- or 6-membered nitrogen-containing heterocyclic group which bonds to a coupling active position by a nitrogen atom.

In the pyrrolotriazole compound represented by formula (I), each preferable substituent of X, $R_1$, $R_2$, $G_1$, $G_2$, $R_3$, $R_4$, $R_5$ and n has the same meaning as each preferable substituent of a cyan coupler represented by formula (I) for use in the silver halide color photographic lightsensitive material mentioned above. Also, in the pyrrolotriazole compound represented by formula (III), each preferable substituent of X, $R_1$, $R_2$, $R_3$, $R_4$, $R_{11}$, $R_{12}$, $R_{13}$, and $R_{14}$ has the same meaning as each preferable substituent of a cyan coupler represented by formula (III) for use in the silver halide color photographic lightsensitive material mentioned above.

(IV)

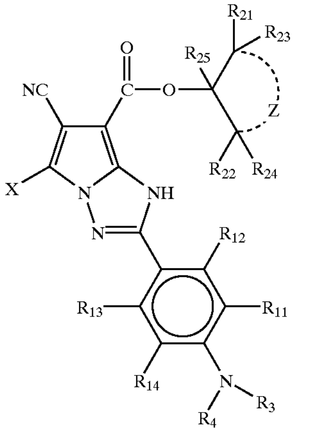

In formula (IV), X, $R_3$, $R_4$, $R_{11}$, $R_{12}$, $R_{13}$, and $R_{14}$ have the same meanings as X, $R_3$, $R_4$, $R_{11}$, $R_{12}$, $R_{13}$, and $R_{14}$ in formula (III) described above.

Also, Z, $R_{21}$, $R_{22}$, $R_{23}$, $R_{24}$, and $R_{25}$ in formula (IV) have the same meanings as Z, $R_{21}$, $R_{22}$, $R_{23}$, $R_{24}$, and $R_{25}$ in formula (V) described above.

A particularly favorable combination as a pyrrolotriazole compound represented by formula (IV) of the present invention is that X is a hydrogen atom, each of $R_{21}$ and $R_{22}$ is t-butyl, each of $R_{23}$, $R_{24}$, and $R_{25}$ is a hydrogen atom, Z forms a cyclohexane ring, the 4-position of this cyclohexane ring is substituted by a 1- to 8-carbon alkyl group, $R_3$ and $R_4$ form a ring structure (preferably a group which forms a 6-membered ring bonded by a nitrogen atom, e.g., morpholino, piperadinyl substituted by an acyl group, or piperidino substituted by a carboxyl group), $R_{11}$ is a substituted or nonsubstituted, 1- to 32-carbon alkylsulfonylamino group, substituted or nonsubstituted, 6- to 30-carbon arylsulfonylamino group, or nitro group, and each of $R_{12}$ to $R_{14}$ is a hydrogen atom or a 6- to 30-carbon arylsulfonylamino group having a substituent. The substituent, which the arylsulfonylamino group has, is preferably a 1- to 32-carbon alkoxy group, 1- to 32-carbon alkyl group, 1- to 32-carbon sulfonylamino group, 1- to 32-carbon acylamino group, or halogen atom.

Practical examples of cyan couplers and pyrrolotriazole compounds defined by the present invention will be presented below. However, the present invention is not limited to these examples.

(1)

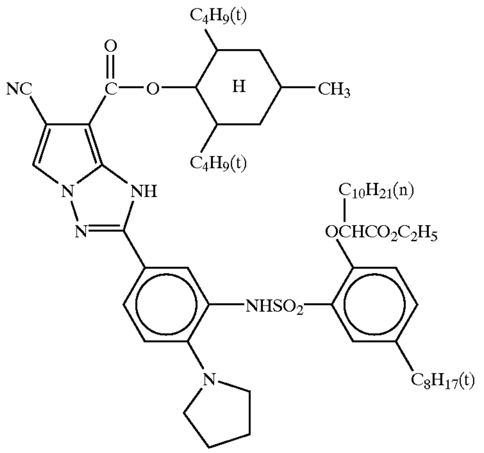

-continued (2)

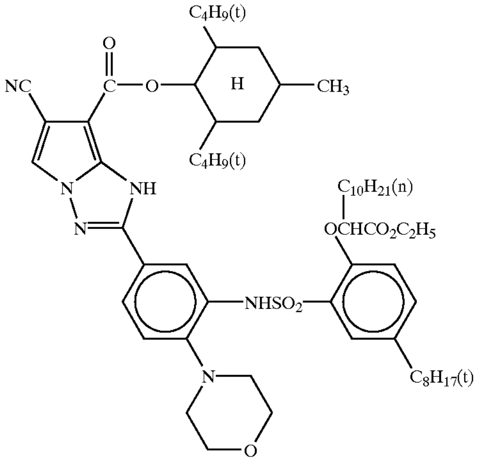

(3)

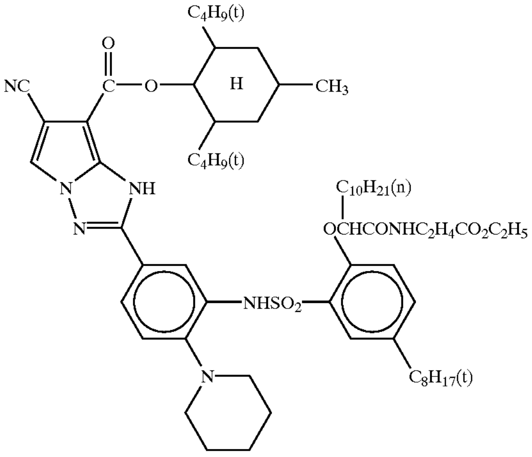

(4)

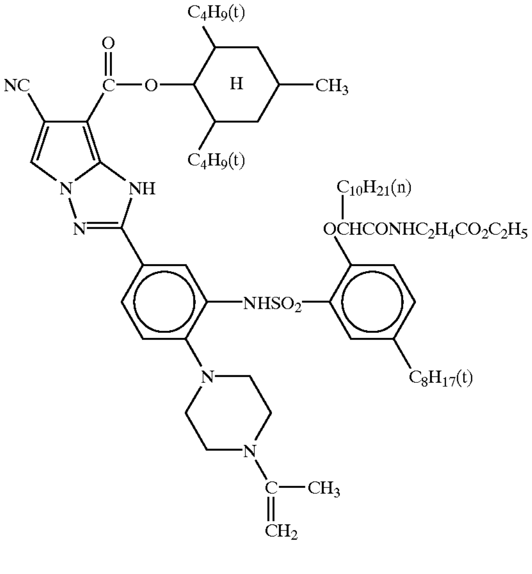

-continued
(5)
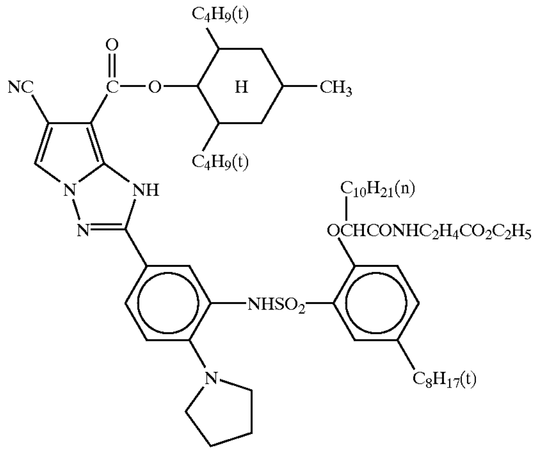
(6)
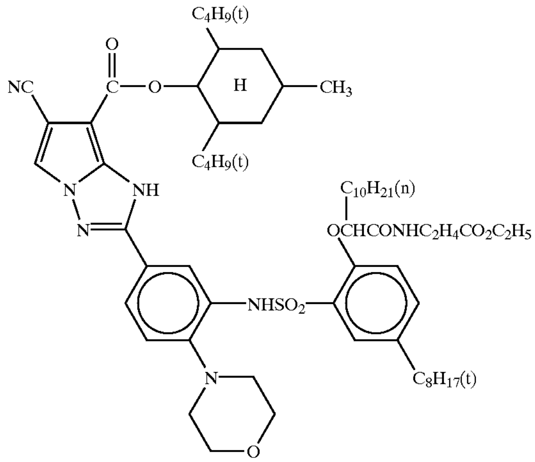
(7)
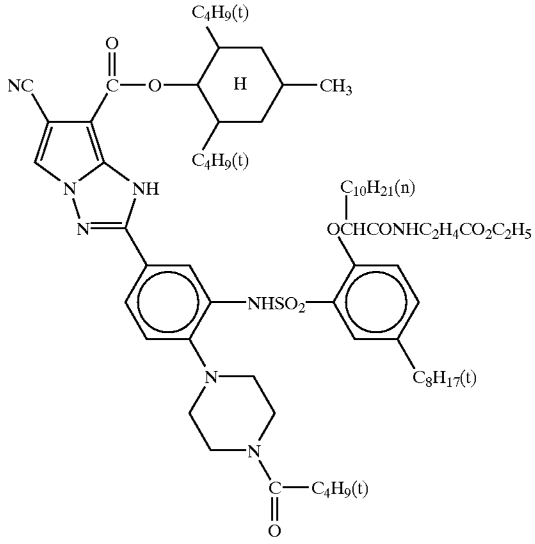
-continued
(8)
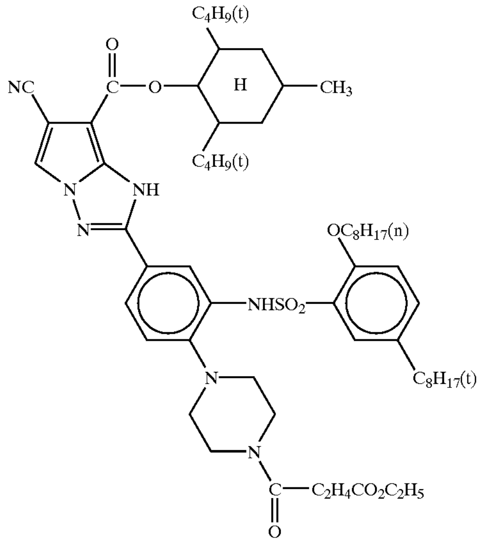
(9)
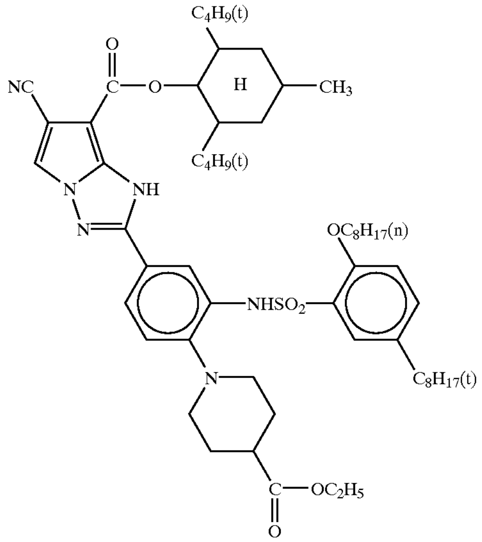
(10)
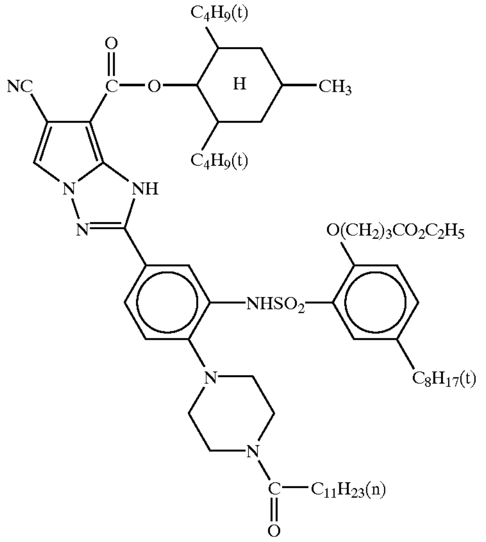

-continued
(11)
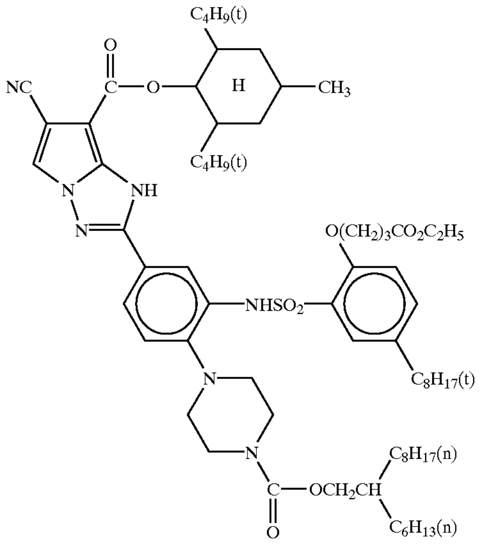
(12)
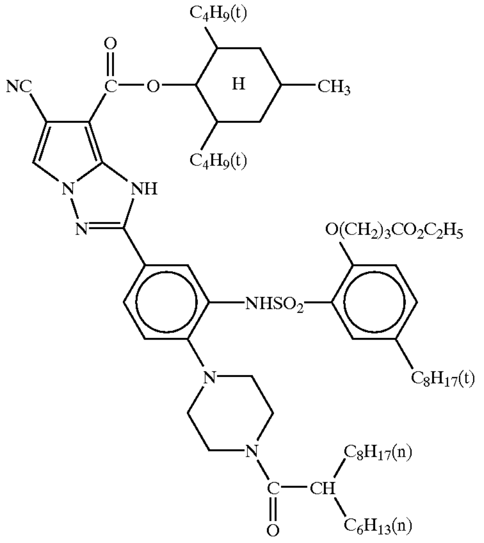
(13)
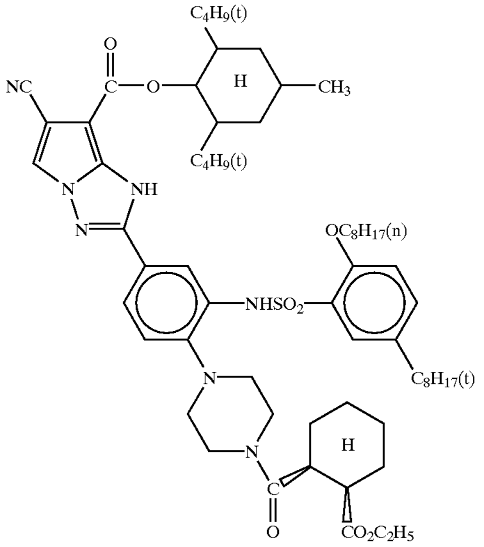
-continued
(14)
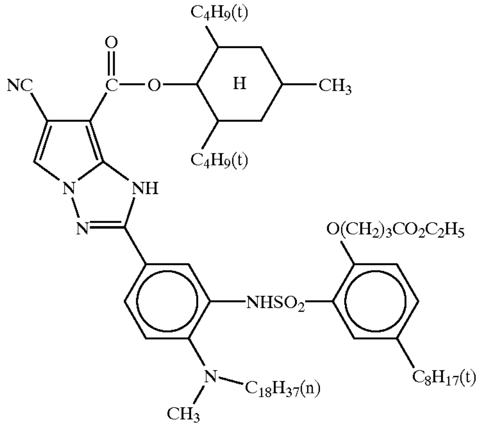
(15)
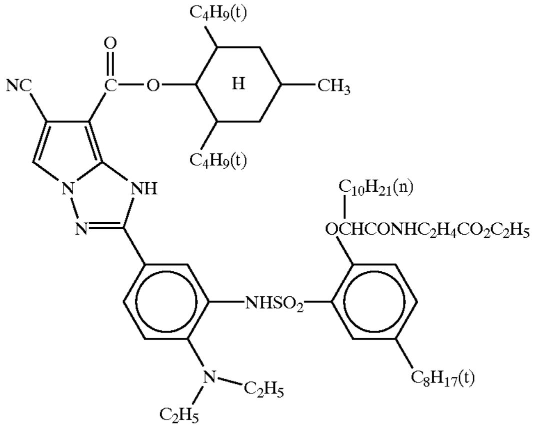
(16)
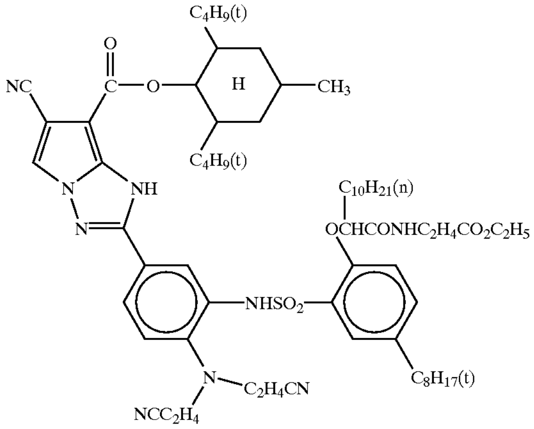

-continued
(17)
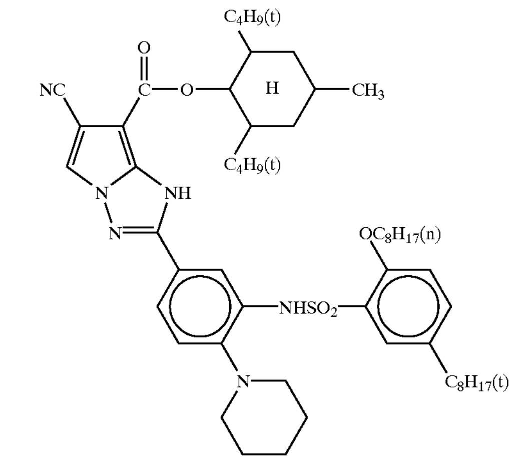
(18)
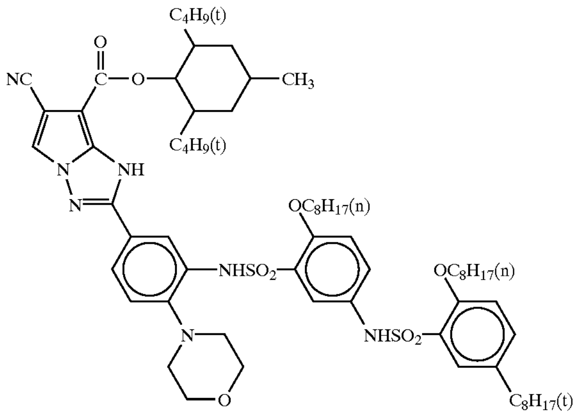
(19)
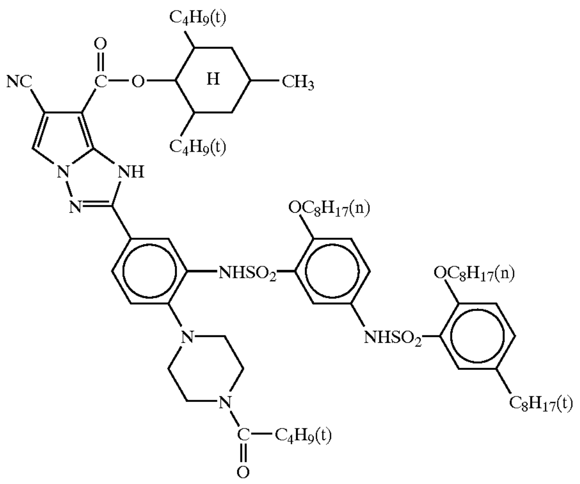
-continued
(20)
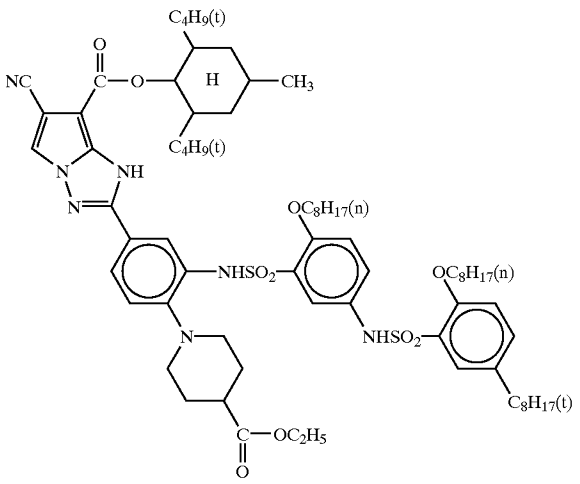
(21)
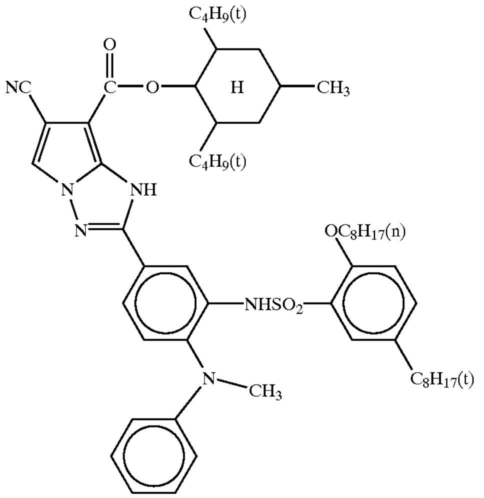
(22)
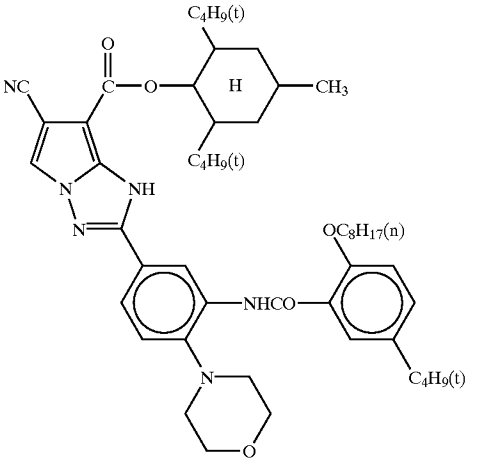

-continued
(23)
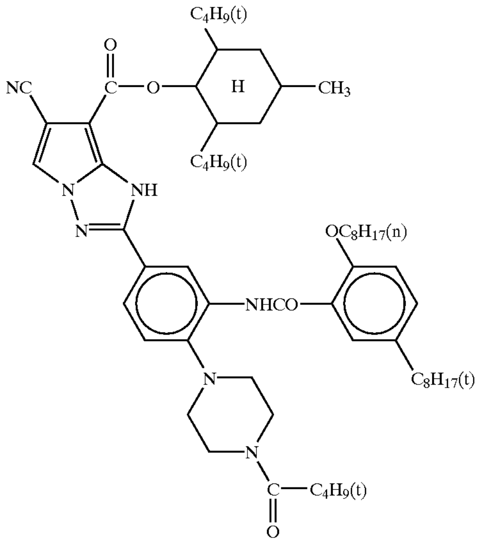
(24)
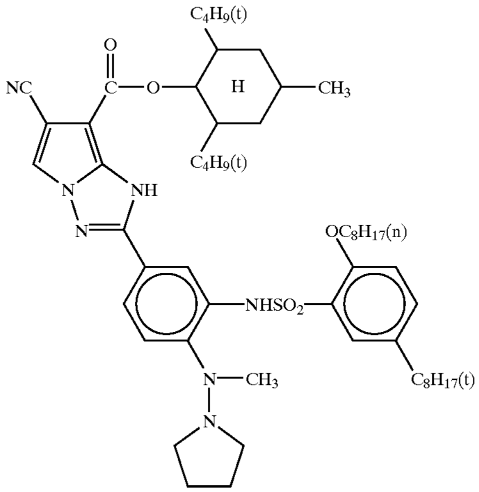
(25)
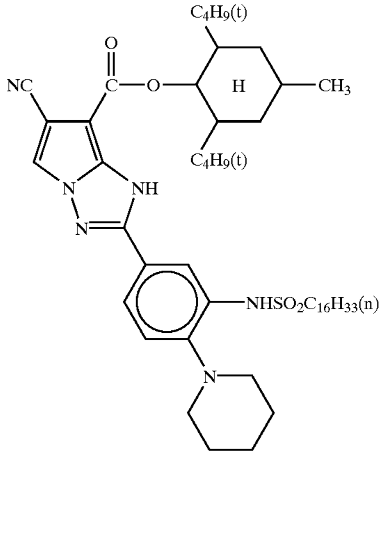
-continued
(26)
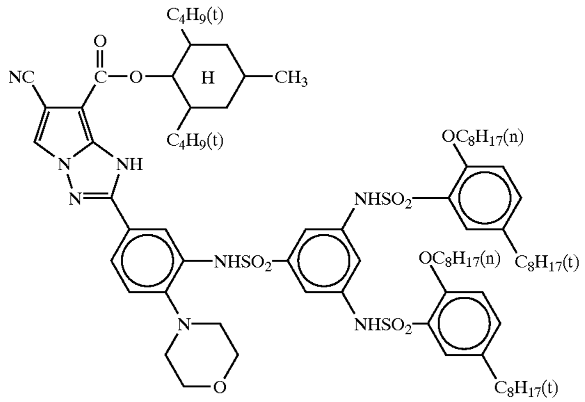
(27)
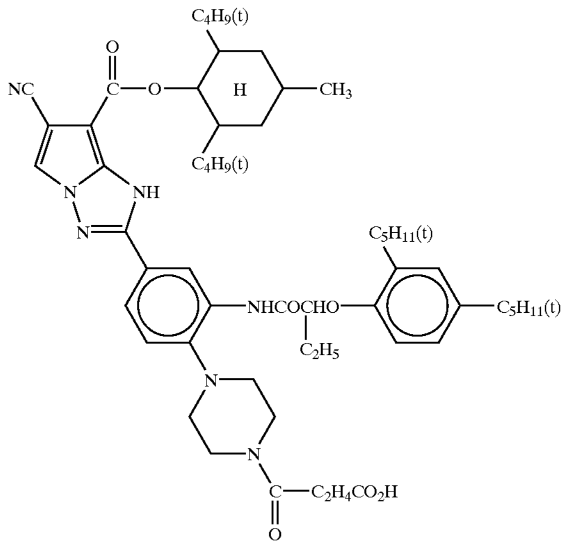
(28)
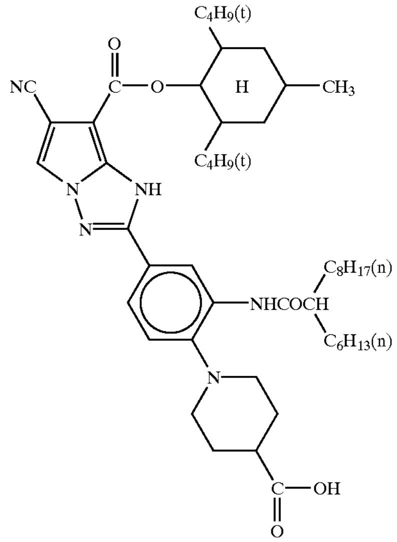

-continued
(29)
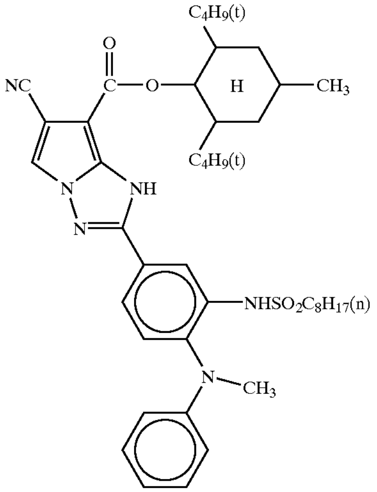
(30)
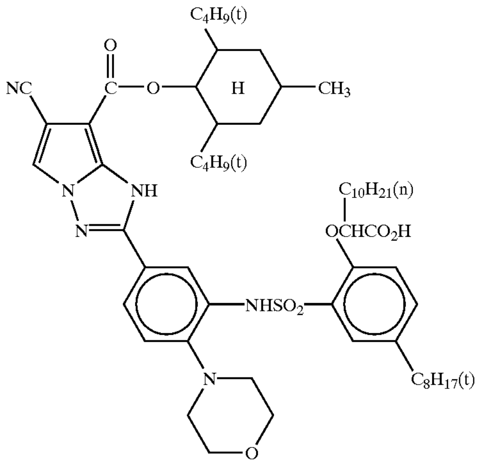
(31)
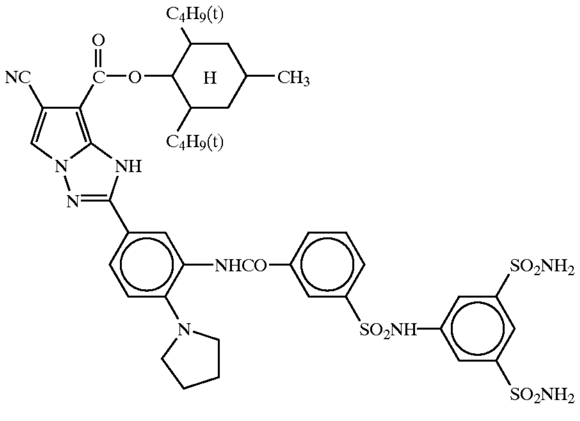
-continued
(32)
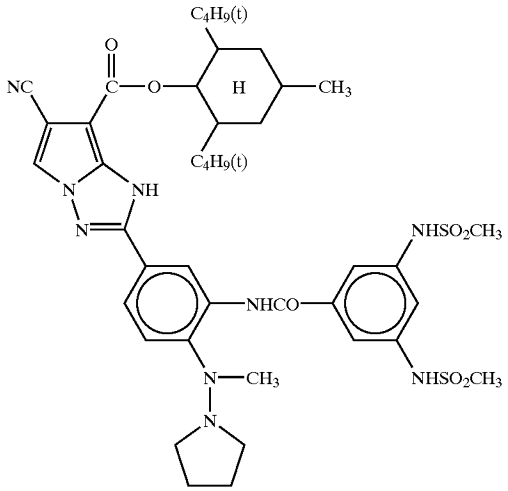
(33)
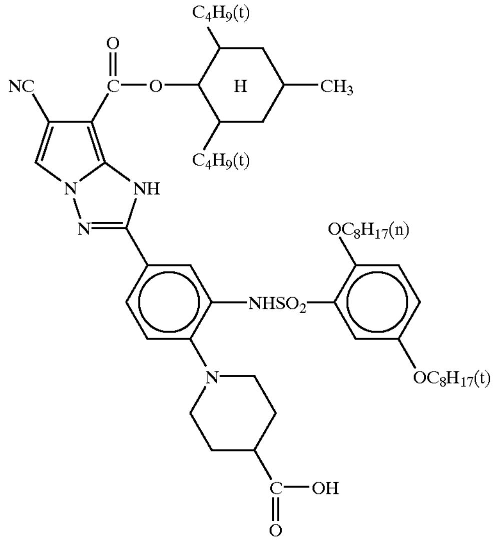
(34)
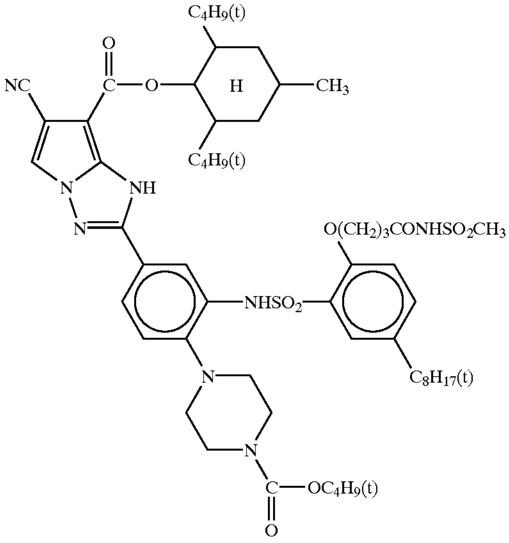

-continued
(35)
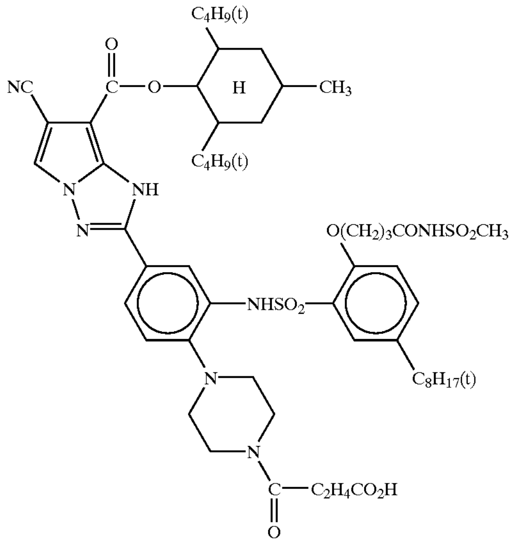
(36)
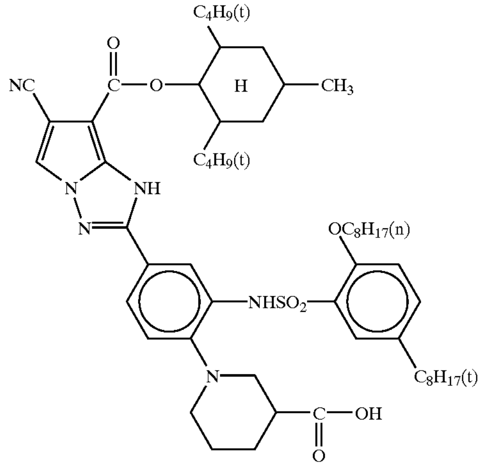
(37)
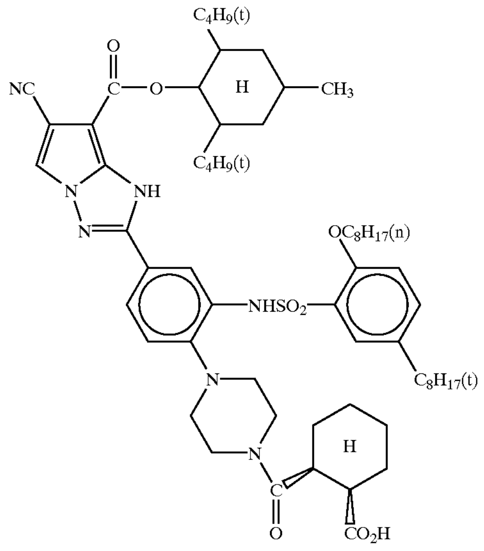
-continued
(38)
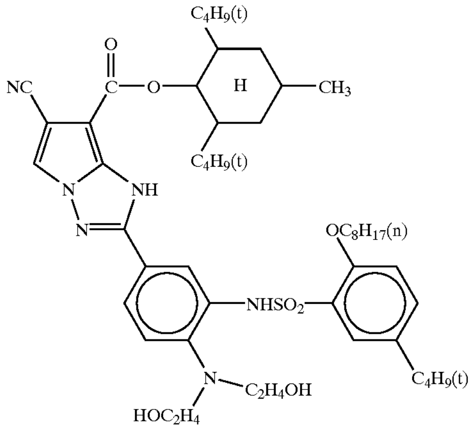
(39)
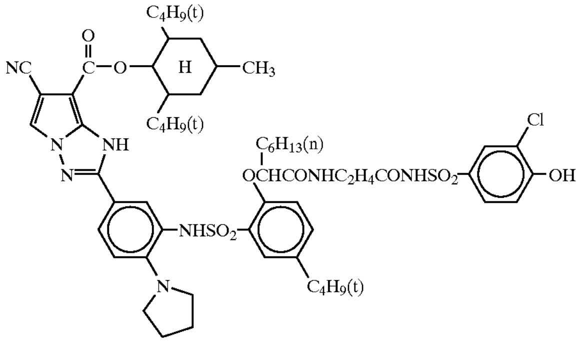
(40)
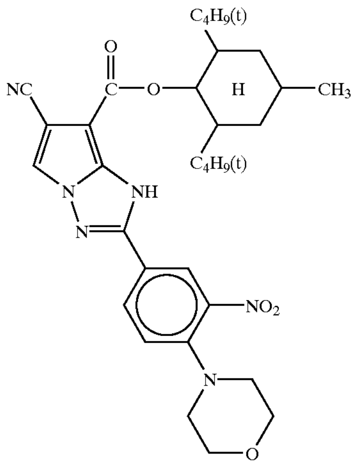

-continued
(41)
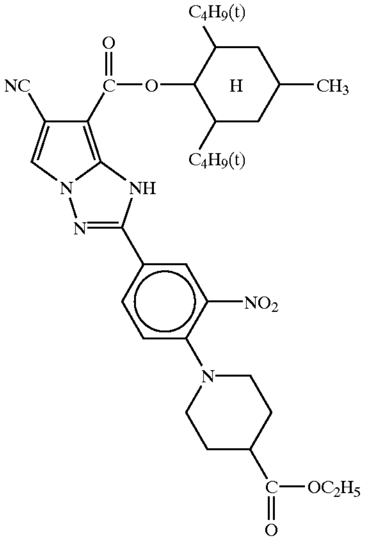
(42)
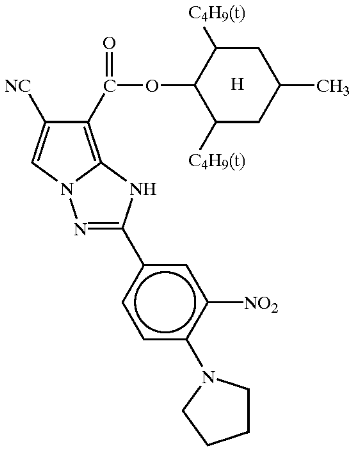
(43)
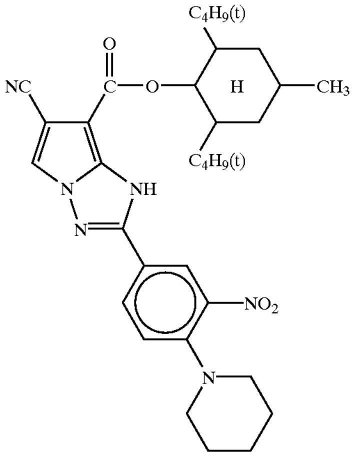
-continued
(44)
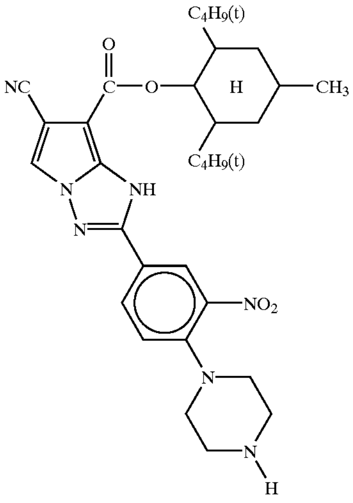
(45)
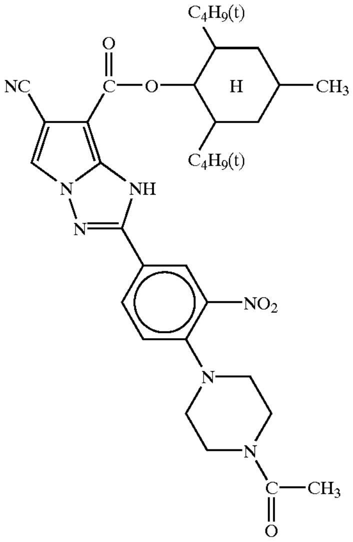
(46)
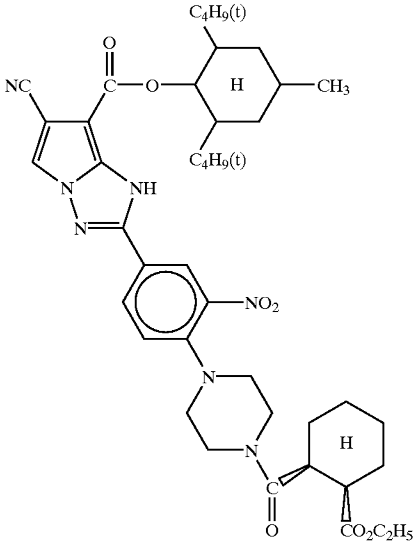

-continued
(47)
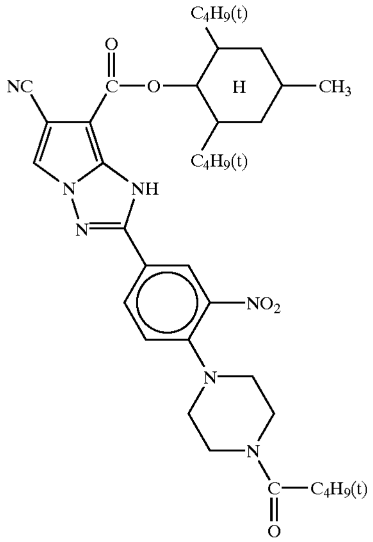
(48)
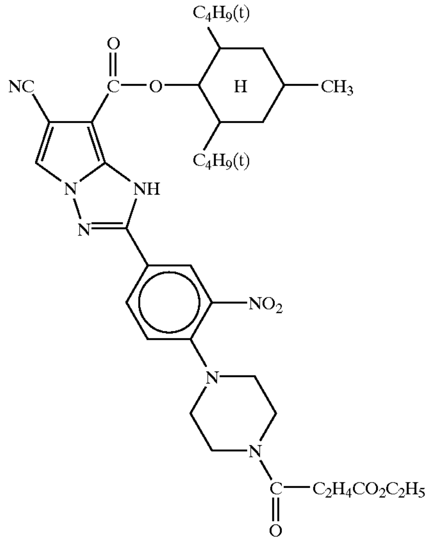
(49)
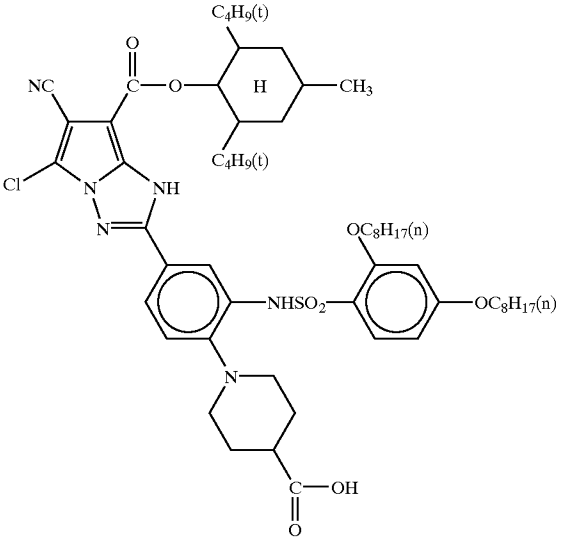
-continued
(50)
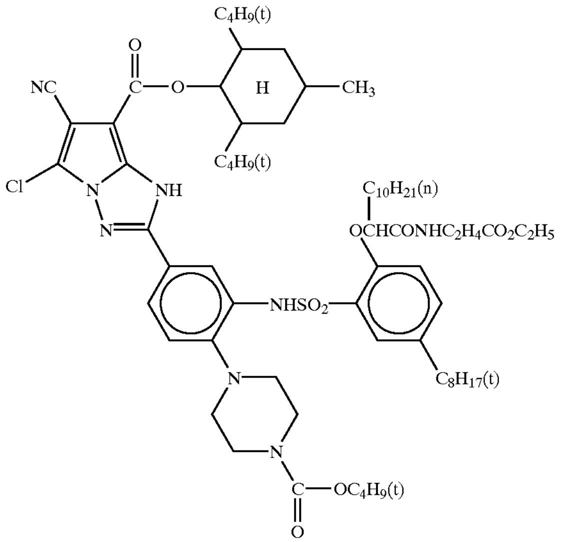
(51)
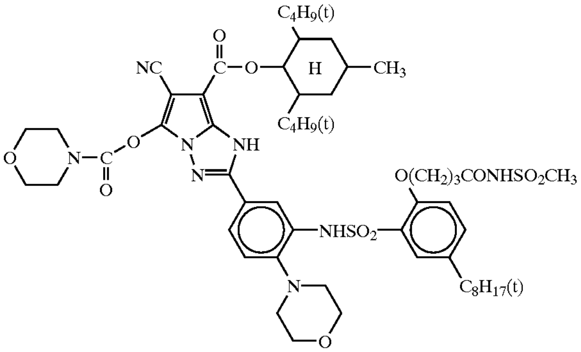
(52)
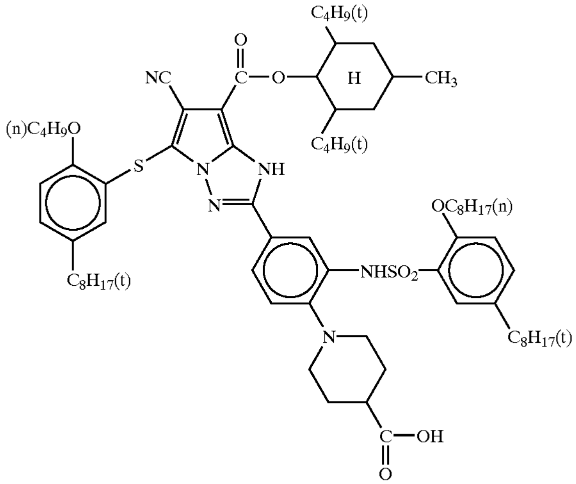

-continued
(53)
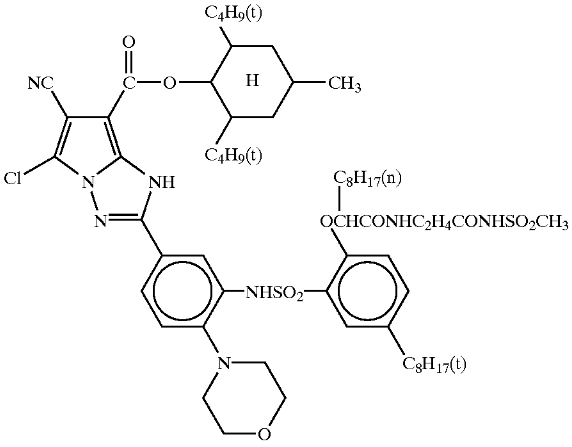
(54)
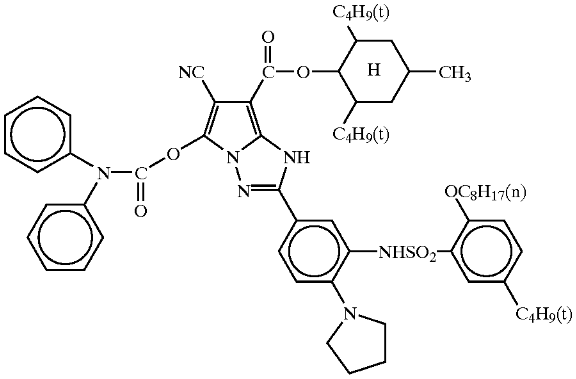
(55)
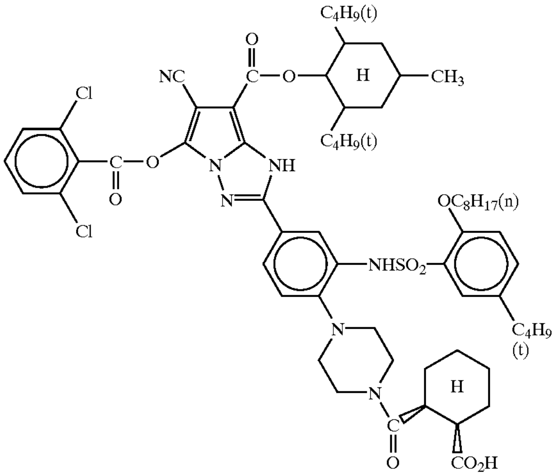
-continued
(56)
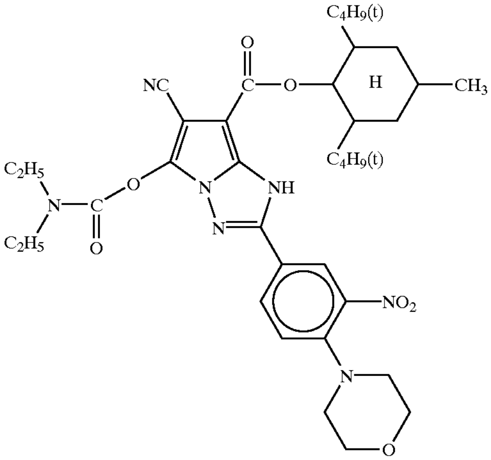
(57)
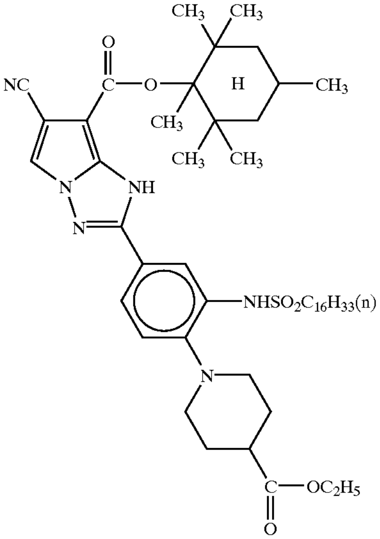
(58)
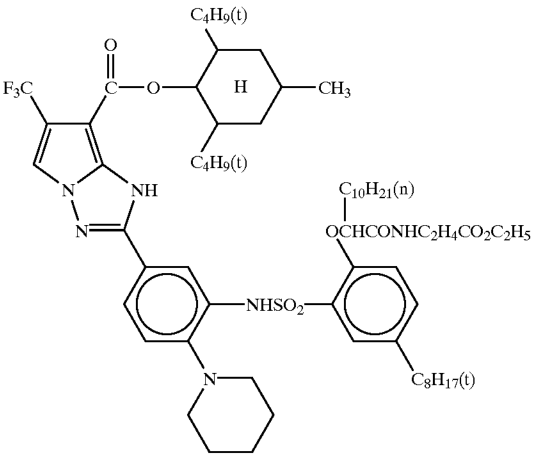

-continued
(59)
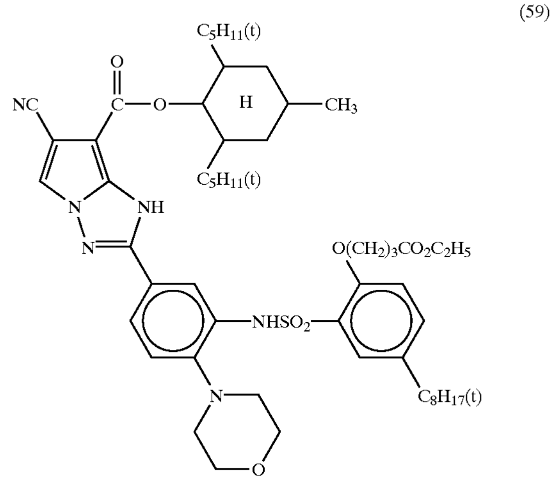
(60)
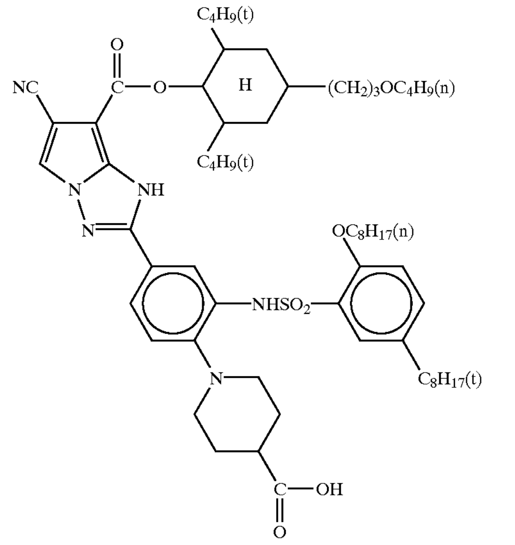
(61)
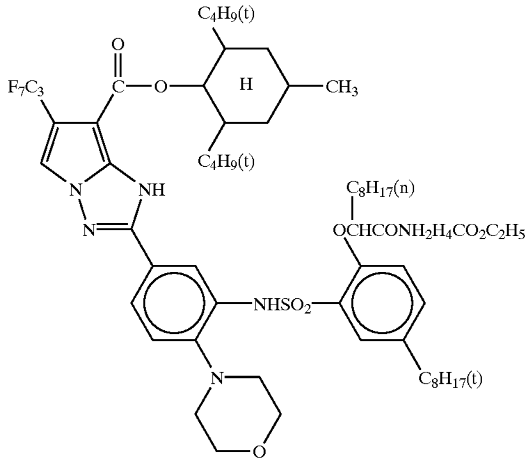
-continued
(62)
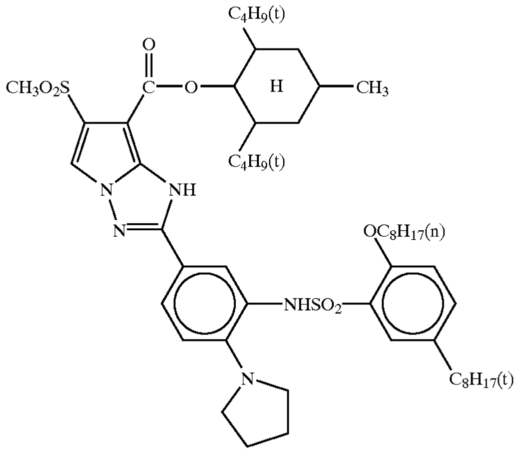
(63)
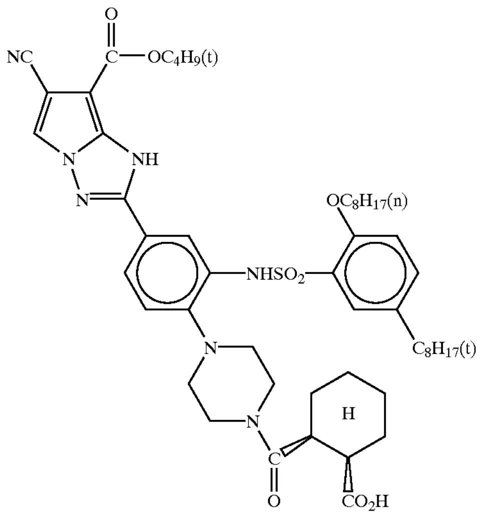
(64)
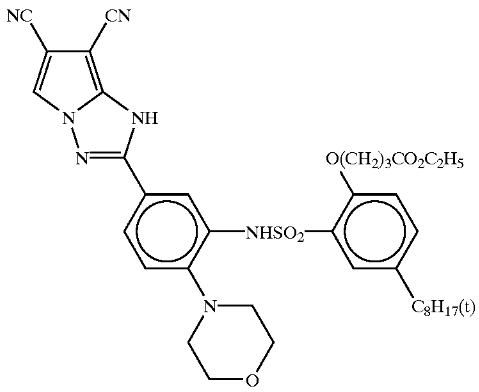

-continued
(65)
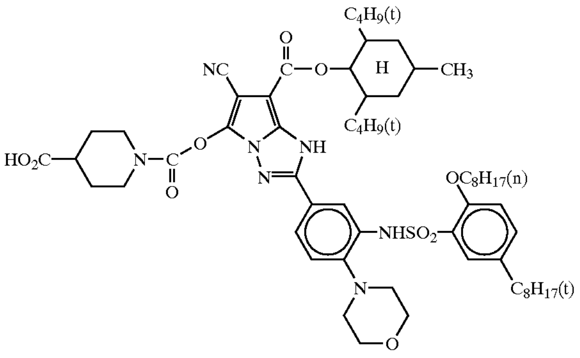
(66)
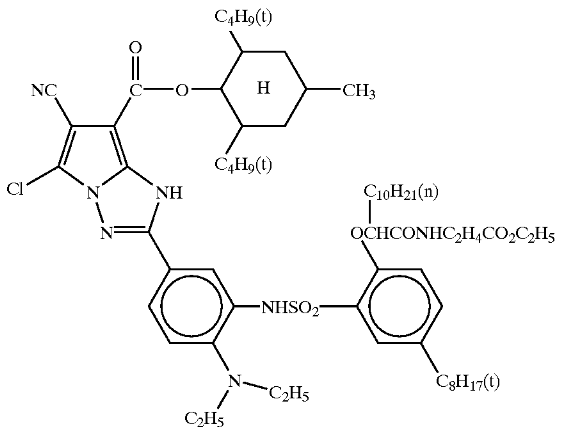
(67)
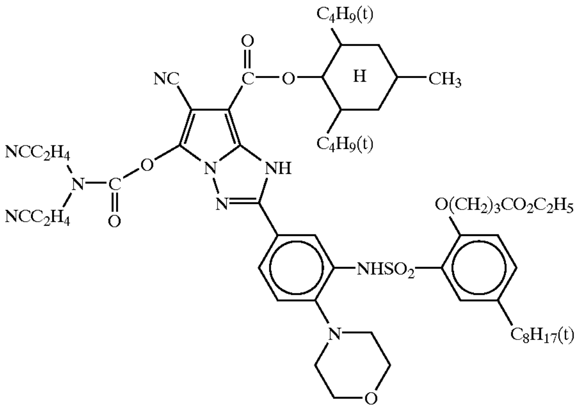
-continued
(68)
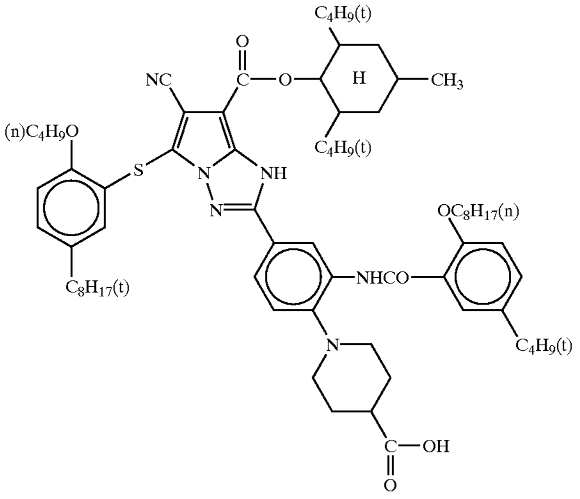
(69)
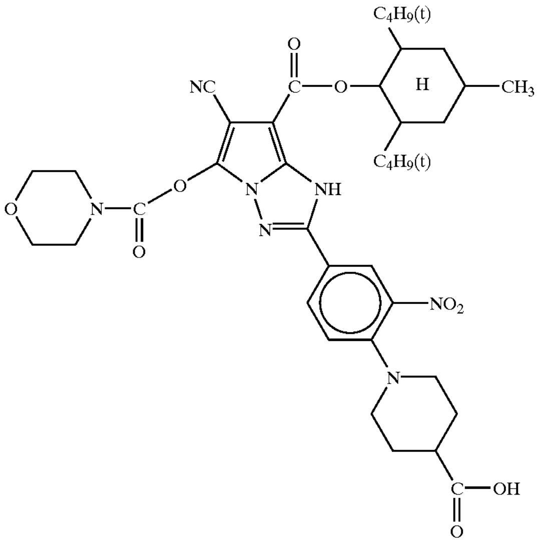
(70)
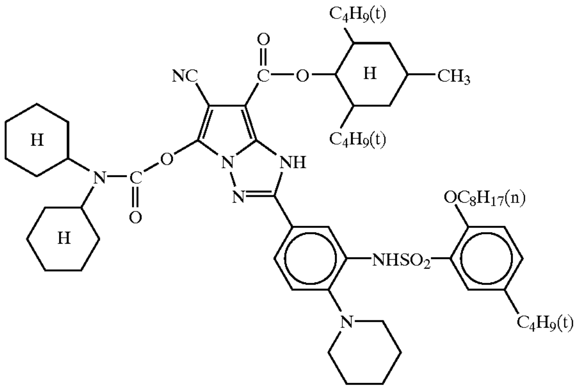

-continued
(71)
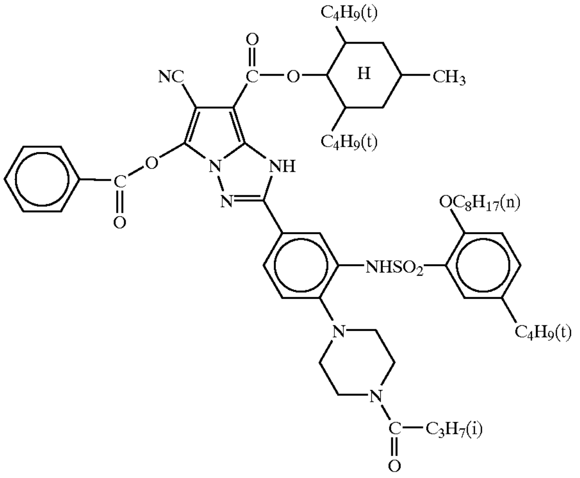
(72)
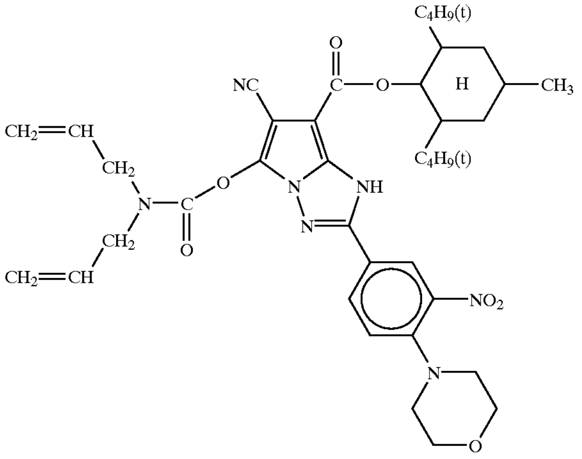
(73)
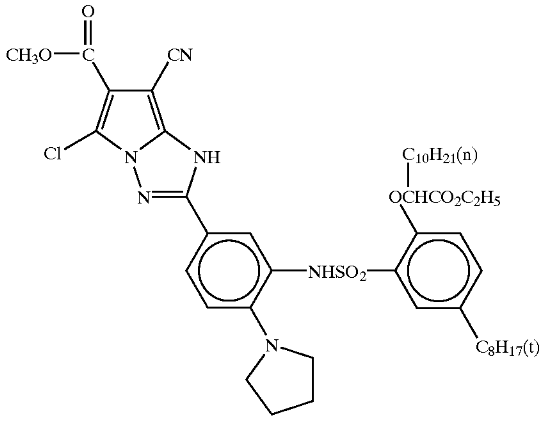
-continued
(74)
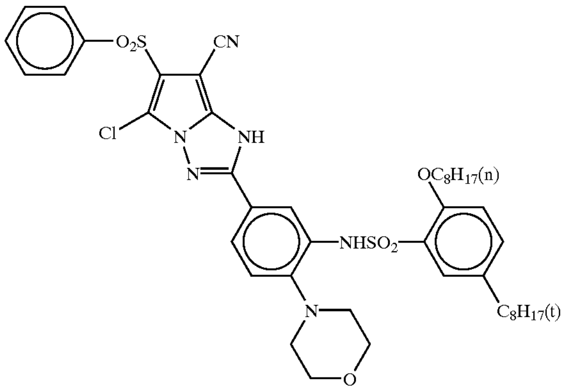
(75)
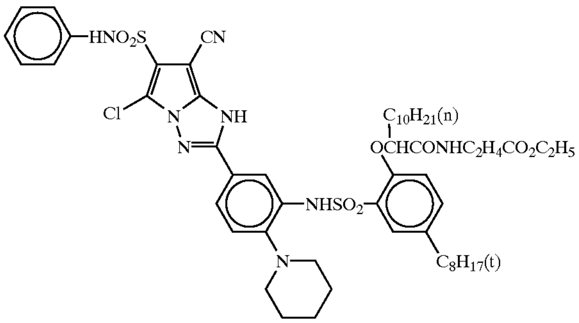
(76)
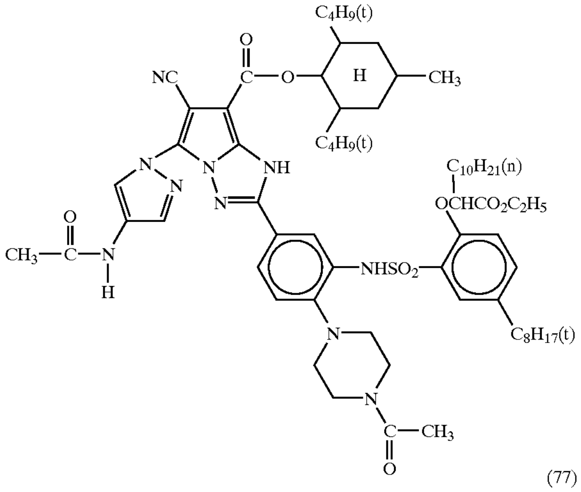
(77)
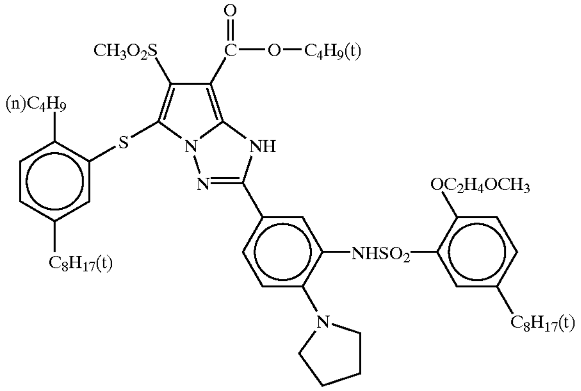

-continued
(78)
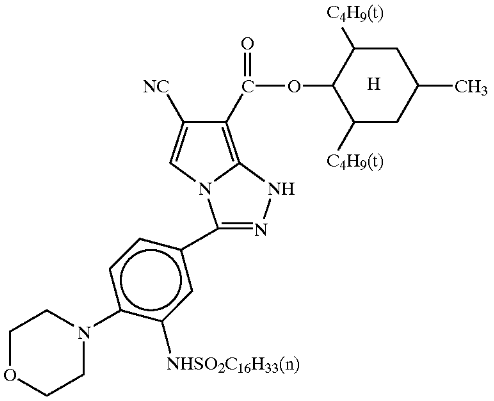
(79)
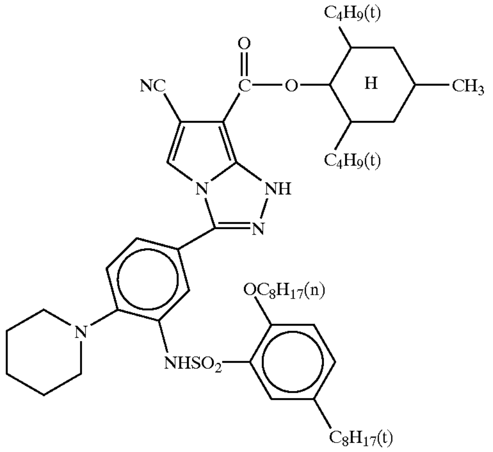
(80)
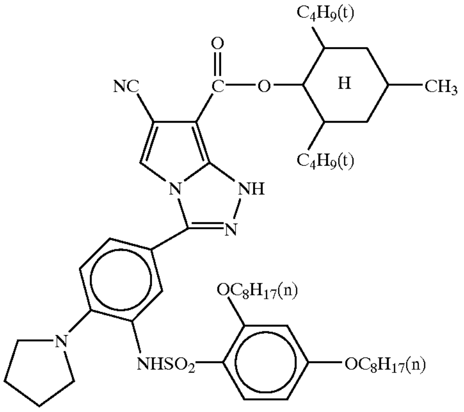
-continued
(81)
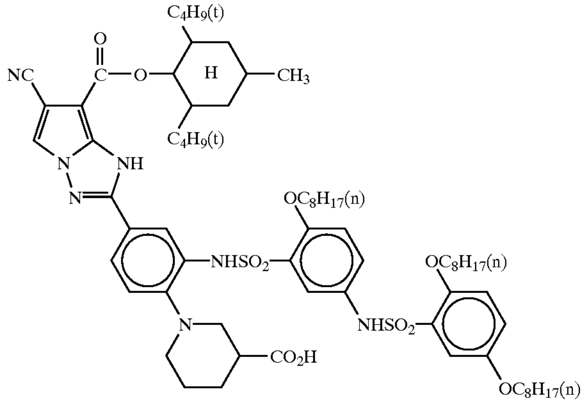
(82)
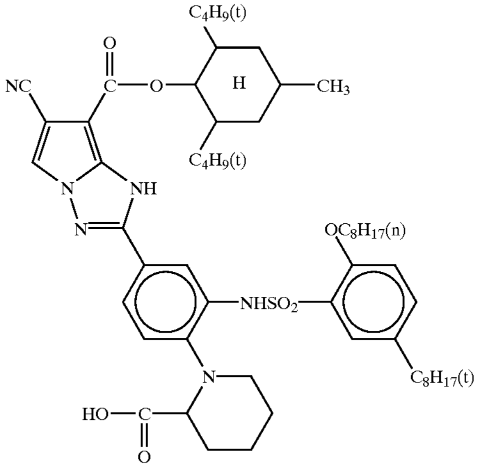
(83)
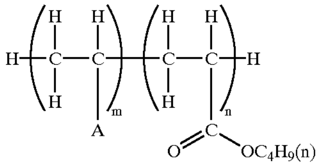
m : n = 60:40
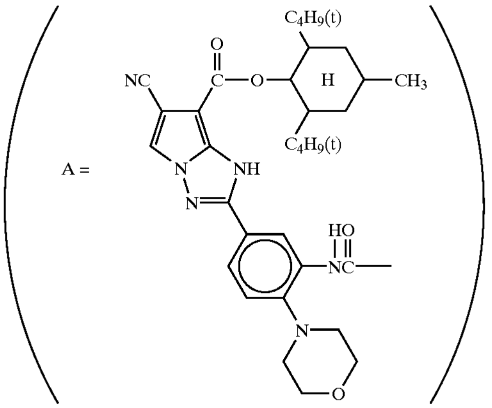
A compound represented by formula (V) can be synthesized by the following method.
Practical synthesis examples of a pyrrolotriazole compound of the present invention will be described below.
Synthesis Example 1
Synthesis of Example Compounds 6 and 40
Example compounds (6) and (40) were synthesized by the following synthesis route.

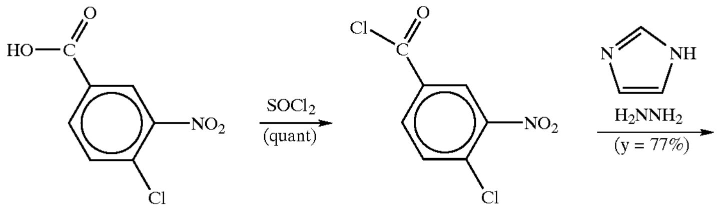
(A)
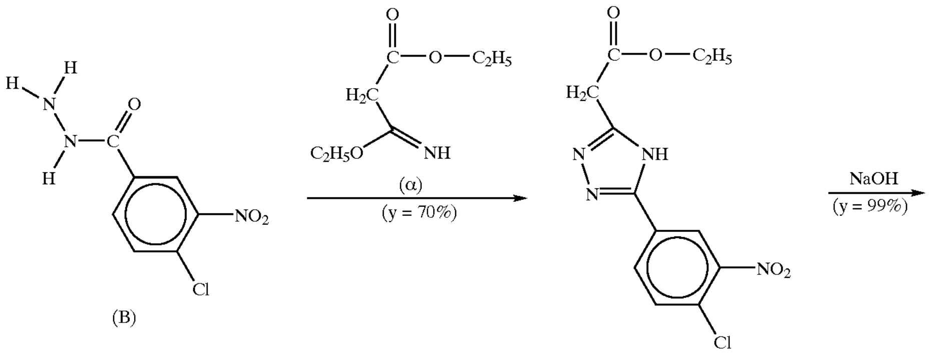
(B) (C)
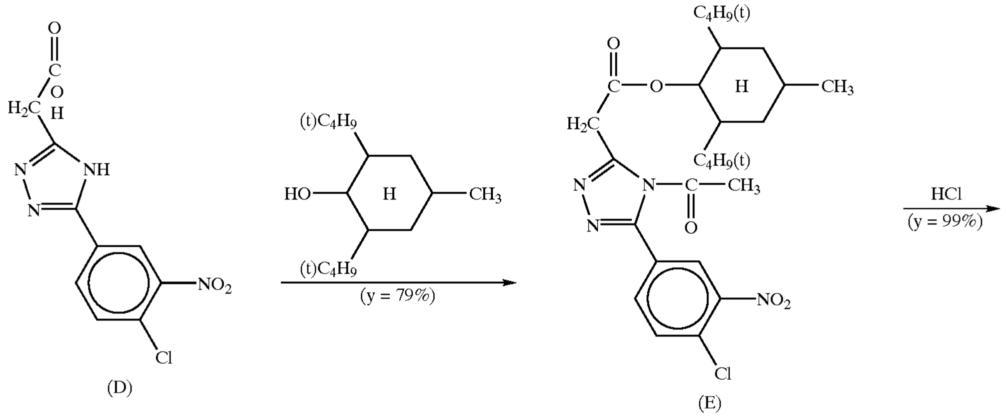
(D) (E)
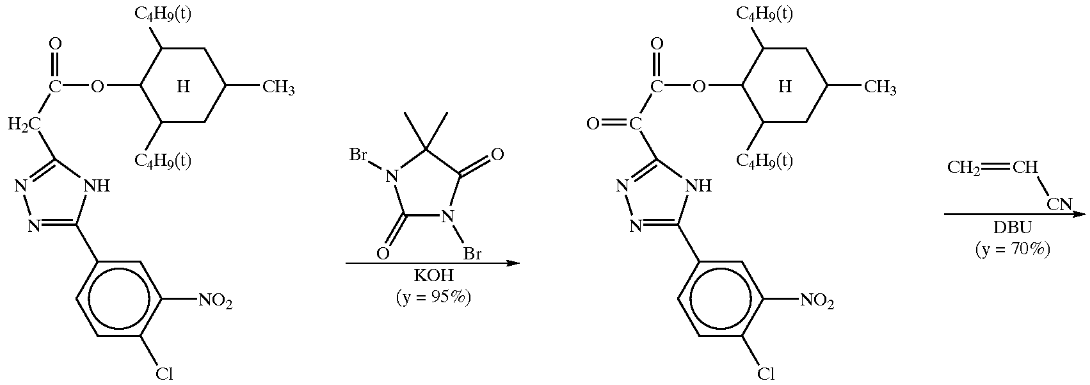
(F) (G)

-continued

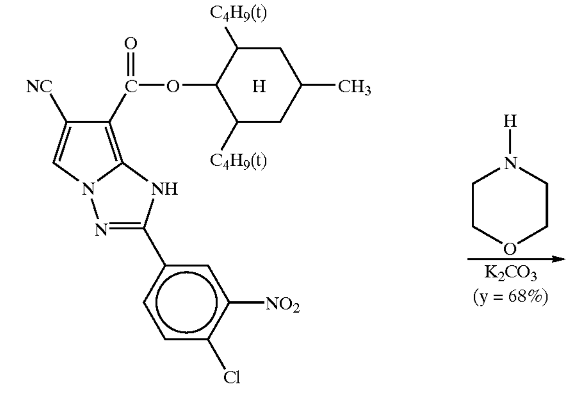

(H)

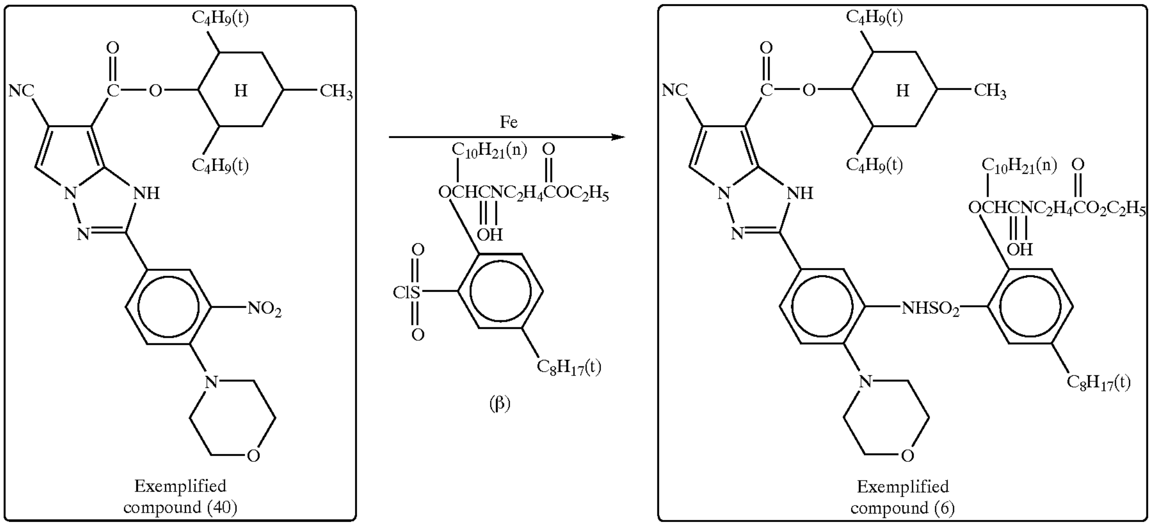

Synthesis of Compound (A)

At 10° C. or less, 76.3 mL (1.05 mol) of thionyl chloride were dropped into a solution of 500 mL of toluene containing 202 g (1 mol) of 4-chloro-3-nitro-benzoic acid and 1 mL of N,N-dimethylformamide. The reaction solution was heated and stirred for 90 min at reflux temperature (the reaction solution changed from a suspension to a uniform solution). The toluene was distilled off at reduced pressure to obtain a wax-like solid matter (A) weighing 220 g.

Synthesis of Compound (B)

At 5° C. or less, 300 mL of an acetonitrile solution containing 220 g (1 mol) of the compound (A) was slowly dropped into 3,000 mL of an acetonitrile solution containing 136.2 g (2 mol) of imidazole. Subsequently, 150 g (3 mol) of hydrazine monohydrate were dropped at 13° C. or less. The reaction solution was stirred for 90 min at 15° C., and the precipitate was filtered and well washed with water. The obtained crystal was dried over night at 50° C. to obtain a compound (B) weighing 166 g (yield 77%) (melting point: 170 to 172° C.; dec.)

Synthesis of Compound (C)

At room temperature, 104.6 mL (0.75 mol) of triethylamine were slowly dropped into 500 mL of an ethyl acetate solution containing 146.7 g (0.75 mol) of a compound (α-HCl salt) under stirring. The reaction solution was subsequently stirred for 30 min at room temperature, and then 500 mL of water were added to perform separation and extraction. The organic layer was washed with salt water. After the organic layer was dried by magnesium sulfate, the ethyl acetate was distilled off at reduced pressure to obtain an oily matter (α) weighing 119 g. 119 g of this oily matter (α) were injected into 1,000 mL of a toluene solution containing 161.7 g (0.75 mol) of the compound (B) under stirring at room temperature. The reaction solution was heated and held at an internal temperature of 80° C., and ethanol produced was distilled off. The internal temperature was further raised to 110° C., and water produced was distilled off over 3 hr. After that, 500 mL of the toluene were distilled off at reduced pressure, the internal temperature was lowered to 70 to 75° C., and 500 mL of acetonitrile were slowly injected. The reaction solution was stirred under reflux for 1 hr and slowly cooled over long periods of time until the internal temperature became room temperature. Furthermore, the resultant solution was stirred for 30 min while being cooled with water. The precipitated crystal was filtered, washed with cold acetonitrile, and dried over night at 40° C. to obtain a compound (C) weighing 163 g (yield 70%) (melting point: 152 to 153° C.).

Synthesis of Compound (D)

At 10° C. or less, 100 g (2.5 mol) of a sodium hydroxide particulate matter were slowly, divisionally added to 1,600 mL of a methanol solution containing 155.4 g (0.5 mol) of the compound (C) while the solution was stirred under ice cooling. The reaction solution was heated to 40° C. and stirred for 90 min at 40° C. After that, the reaction solution was cooled to A an internal temperature of 30° C. and slowly injected into a solution containing 430 mL of hydrochloric acid, 2,000 mL of water, and 1 kg of crushed ice, thereby performing acid precipitation. Furthermore, the reaction solution was stirred for 90 min at 10° C. After that, the crystal was filtered, washed with water and then with cold acetonitrile, and dried over night at 40° C. to obtain a compound (D) weighing 140 g (yield 99%) (melting point: 133 to 152° C.).

Synthesis of Compound (E)

48.1 g (0.49 mol) of potassium acetate were divisionally added to 1,500 mL of an ethyl acetate solution containing 111 g (0.49 mol) of 2,6-di-t-butyl-4-methylcyclohexanol and 138.5 g (0.49 mol) of the compound (D) while the solution was stirred at room temperature. The reaction solution was cooled to 10° C. or less, and 236 mL (2.5 mol) of acetic anhydride were slowly dropped while the internal temperature was held at 15° C. or less. Subsequently, the reaction solution was stirred for 90 min at 40 to 45° C., and the internal temperature was lowered to 5° C. The precipitated crystal was filtered and washed with enough water to remove inorganic substances. Finally, the crystal was washed with cold acetonitrile and dried over night at 50° C. to obtain a compound (E) weighing 206.4 g (yield 79%) (melting point: 178 to 179° C.).

Synthesis of Compound (F)

At room temperature, 39.2 mL of concentrated hydrochloric acid were slowly dropped into 600 mL of an acetonitrile solution containing 203 g (0.38 mol) of a compound (E). The reaction solution was heated and stirred under reflux for 2 hr. After that, the internal temperature was lowered to 40° C., 600 mL of water were dropped, and the resultant solution was stirred for 1 hr at room temperature. The precipitated crystal was filtered, washed with water, and dried over night at 50° C. to obtain a compound (F) weighing 185.1 g (yield 99.2%) (melting point: 191 to 195° C.).

Synthesis of Compound (G)

At room temperature, 108.7 g (0.38 mol) of 1,3-dibromo-5,5-dimethylhydantoin were added to 700 mL of an acetonitrile solution containing 181.7 g (0.37 mol) of a compound (F). Subsequently, 0.44 g of methanesulfonic acid were dropped. The reaction solution was heated and stirred for 90 min under reflux. After the internal temperature was lowered to 30° C., 370 mL of N,N-dimethylformamide were injected, and 150 mL of an aqueous solution containing 45.7 g (0.82 mol) of potassium hydroxide were dropped at 20 to 25° C. under water cooling. The reaction solution was stirred for 90 min at 60° C. and cooled to room temperature, and 1,000 mL of ethyl acetate and 1,000 mL of water were added to perform extraction. The ethyl acetate layer was washed with water and salt water and dried by magnesium sulfate. After that, the solvent was distilled off at reduced pressure, and the resultant material was recrystallized by acetonitrile to obtain a compound (G) weighing 178.3 g (yield 95.4%) (melting point: 195 to 197° C.).

Synthesis of Compound (H)

At room temperature, 186 g (3.5 mol) of acrylonitrile were injected into 370 mL of N,N-dimethylformamide containing 176.8 g (0.35 mol) of a compound (G). Subsequently, 63.9 g (0.42 mol) of DBU (1,8-diazabicyclo [5,4,0]-7-undecene) were injected, and the reaction solution was stirred for 4 hr at 80° C. After the reaction solution was cooled to room temperature, 500 mL of acetonitrile were injected, and 72.3 mL of concentrated hydrochloric acid and 1,500 mL of water were slowly dropped at room temperature. The reaction solution was stirred for 1 hr at room temperature. After that, the precipitated crystal was filtered and washed with water, and the resultant coarse crystal was recrystallized by acetonitrile to obtain a compound (H) weighing 133.3 g (yield 70.5%) (melting point: 265° C.; dec.)

Synthesis of Example Compound 40

43.7 mL (0.5 mol) of morpholine and 65 mL of an N,N-dimethylacetamide solution containing 6.9 g (0.05 mol) of potassium carbonate were heated under stirring until the internal temperature became 100° C. 35 mL of an N,N-dimethylacetamide solution containing 27 g of the compound (H) were dropped, and the resultant solution was stirred for 90 min at 110° C. The reaction solution was cooled to room temperature, and 150 mL of ethyl acetate and 500 mL of water were added to perform extraction. The ethyl acetate layer was washed with water and salt water and dried by magnesium sulfate. After the solvent was distilled off at reduced pressure, the resultant material was recrystallized by acetonitrile to obtain an example compound (40) weighing 20.1 g (yield 68%) (melting point: 283 to 284° C.; dec.)

Synthesis of Example Compound 6

While a solution containing 2 g of ammonium chloride, 40 mL of water, and 200 mL of isopropyl alcohol was stirred at room temperature, 20 g of reduced iron were divisionally added. After the reaction solution was heated under reflux, 20 g of the example compound (40) were slowly, divisionally added, and the resultant solution was stirred under reflux for 30 min. The reaction solution was filtered through Celite under heating, and 100 mL of ethyl acetate and 500 mL of water were added to the filtrate to perform extraction. The ethyl acetate layer was washed with water and salt water and dried by magnesium sulfate. After the solvent was distilled off at reduced pressure, the resultant material was recrystallized by acetonitrile to obtain an intermediate (—$NH_2$ derivative) weighing 17.7 g. At 50° C., 9.2 g of the obtained intermediate were divisionally added to a solution containing 12 g of a compound (β) and 150 mL of acetonitrile. Furthermore, 2 mL of pyridine were dropped, and the resultant solution was stirred under reflux for 1 hr. The reaction solution was cooled to room temperature, and 150 mL of ethyl acetate and 500 mL of water were added to perform extraction. The ethyl acetate layer was washed with water and salt water and dried by magnesium sulfate. After the solvent was distilled off at reduced pressure, the resultant material was recrystallized by acetonitrile to obtain an example compound (6) weighing 9.8 g (melting point: 215 to 217° C.).

Synthesis Example 2

Synthesis of Example Compound 41

77.1 mL (0.5 mol) of ethyl isonipecotate and 65 mL of an N,N-dimethylacetamide solution containing 6.9 g (0.05 mol) of potassium carbonate were heated under stirring until the internal temperature became 80° C. 35 mL of an N,N-dimethylacetamide solution containing 27 g of the compound (H) were dropped, and the resultant solution was stirred for 2 hr at 85° C. The reaction solution was cooled to room temperature, and 150 mL of ethyl acetate and 500 mL of water were added to perform extraction. The ethyl acetate layer was washed with water and salt water and dried by magnesium sulfate. After that, the solvent was distilled off at reduced pressure, and the resultant material was recrystallized by acetonitrile to obtain an example compound (41) weighing 25.5 g (yield 77%) (melting point: 178 to 180° C.).

Synthesis Example 3

Synthesis of Example Compound 42

41.7 mL (0.5 mol) of pyrrolidine and 65 mL of an N,N-dimethylacetamide solution containing 6.9 g (0.05 mol) of potassium carbonate were heated under stirring until the internal temperature became 75° C. 35 mL of an N,N-dimethylacetamide solution containing 27 g of the compound (H) were dropped, and the resultant solution was stirred for 90 min at 85° C. The reaction solution was cooled to room temperature, and 150 mL of ethyl acetate and 500 mL of water were added to perform extraction. The ethyl acetate layer was washed with water and salt water and dried by magnesium sulfate. After that, the solvent was distilled off at reduced pressure, and the resultant material was recrystallized by acetonitrile to obtain an example compound (42) weighing 25.9 g (yield 90.1%) (melting point: 210 to 215° C.).

Synthesis Example 4

Synthesis of Example Compound 43

49.4 mL (0.5 mol) of piperidine and 65 mL of an N,N-dimethylacetamide solution containing 6.9 g (0.05 mol) of potassium carbonate were heated under stirring until the internal temperature was 80° C. 35 mL of an N,N-dimethylacetamide solution containing 27 g of the compound (H) were dropped, and the resultant solution was stirred for 90 min at 85° C. The reaction solution was cooled to room temperature, and 150 mL of ethyl acetate and 500 mL of water were added to perform extraction. The ethyl acetate layer was washed with water and salt water and dried by magnesium sulfate. After that, the solvent was distilled off at reduced pressure, and the resultant material was recrystallized by acetonitrile to obtain an example compound (43) weighing 23.6 g (yield 80.1%) (melting point: 235 to 240° C.).

Synthesis Example 5

Synthesis of Example Compound 44

43.1 mL (0.5 mol) of piperazine anhydride and 65 mL of an N,N-dimethylacetamide solution containing 6.9 g (0.05 mol) of potassium carbonate were heated under stirring until the internal temperature became 80° C. 35 mL of an N,N-dimethylacetamide solution containing 27 g of the compound (H) were dropped, and the resultant solution was stirred for 3 hr at 90° C. The reaction solution was cooled to room temperature, and 150 mL of ethyl acetate and 500 mL of water were added to perform extraction. The ethyl acetate layer was washed with water and salt water and dried by magnesium sulfate. After that, the solvent was distilled off at reduced pressure, and the resultant material was recrystallized by acetonitrile/water to obtain an example compound (44) weighing 25.1 g (yield 85%) (melting point: 233 to 238° C.; dec.).

Synthesis Example 6

Synthesis of Example Compound 47

1.7 mL of pivalic acid chloride were dropped into 50 mL of an N,N-dimethylacetamide solution containing 8.85 g (0.015 mol) of the example compound (44) under stirring at an internal temperature of 10° C., and the resultant solution was stirred for 30 min at room temperature. 100 mL of ethyl acetate and 300 mL of water were added to the reaction solution to perform extraction. The ethyl acetate layer was washed with water and salt water and dried by magnesium sulfate. After that, the solvent was distilled off at reduced pressure, and the resultant material was recrystallized by acetonitrile to obtain an example compound (47) weighing 9.3 g (yield 91.7%).

Synthesis Example 7

Synthesis of Example Compound 7

While a solution containing 1 g of ammonium chloride, 20 mL of water, and 100 mL of isopropyl alcohol was stirred at room temperature, 10 g of reduced iron were divisionally added. After the reaction solution was heated under reflux, 8.8 g (0.013 mol) of the example compound (47) were slowly, divisionally added, and the resultant solution was stirred under reflux for 30 min. The reaction solution was filtered through Celite under heating, and 100 mL of ethyl acetate and 500 mL of water were added to the filtrate to perform extraction. The ethyl acetate layer was washed with water and salt water and dried by magnesium sulfate. After the solvent was distilled off at reduced pressure, the resultant material was recrystallized by acetonitrile to obtain an intermediate (—$NH_2$ derivative) weighing 6.7 g. At 50° C., 6.7 g of the obtained intermediate were divisionally added to a solution containing 9 g of the compound (β) used in synthesis example 1 described earlier and 100 mL of acetonitrile. Furthermore, 1.5 mL of pyridine were dropped, and the resultant solution was stirred under reflux for 1 hr. The reaction solution was cooled to room temperature, and 100 mL of ethyl acetate and 300 mL of water were added to perform extraction. The ethyl acetate layer was washed with water and salt water and dried by magnesium sulfate. After the solvent was distilled off at reduced pressure, the resultant material was recrystallized by acetonitrile to obtain an example compound (7) weighing 6.3 g (melting point: 216 to 219° C.).

Synthesis Example 8

Synthesis of Example Compound 9

While a solution containing 2 g of ammonium chloride, 40 mL of water, and 200 mL of isopropyl alcohol was stirred at room temperature, 20 g of reduced iron were divisionally added. After the reaction solution was heated under reflux, 23 g of the example compound (41) were slowly, divisionally added, and the resultant solution was stirred under reflux for 30 min. The reaction solution was filtered through Celite under heating, and 200 mL of ethyl acetate and 500 mL of water were added to the filtrate to perform extraction. The ethyl acetate layer was washed with water and salt water and dried by magnesium sulfate. After the solvent was distilled off at reduced pressure, the resultant material was recrystallized by acetonitrile to obtain an intermediate (—$NH_2$ derivative) weighing 17.2 g. At 50° C., 17.2 g of the obtained intermediate were divisionally added to a solution containing 15 g of 5-(t-octyl)-2-octyloxybenzenesulfonyl chloride and 150 mL of acetonitrile. Furthermore, 3 mL of pyridine were dropped, and the resultant solution was stirred under reflux for 1 hr. The reaction solution was cooled to room temperature, and 150 mL of ethyl acetate and 500 mL of water were added to perform extraction. The ethyl acetate layer was washed with water and salt water and dried by magnesium sulfate. After the solvent was distilled off at reduced pressure, the resultant material was recrystallized by acetonitrile to obtain an example compound (9) weighing 20.2 g, (melting point: 218 to 219° C.).

Synthesis Example 9

Synthesis of Example Compound 33

At 15° C. or less, 11 g of a potassium hydroxide particulate matter were divisionally added to a solution containing 20 g of the example compound (9) and 100 mL of methanol. Subsequently, the reaction solution was stirred for 90 min at 50° C. The reaction solution was then cooled to room temperature and slowly injected into a solution, containing 25 mL of hydrochloric acid and 200 mL of water, whose internal temperature was lowered to 10° C., thereby crystallizing the material. The resultant material was recrystallized by acetonitrile to obtain an example compound (33) weighing 16.1 g (melting point: 252 to 254° C.; dec.)

The coating amount of a cyan coupler of the present invention is preferably 0.01 to 2 $g/m^2$, and more preferably, 0.05 to 1.0 $g/m^2$.

In a silver halide color photographic light-sensitive material of the present invention, at least one sensitive layer need only be formed on a support. A typical example is a silver halide photographic lightsensitive material having, on a support, at least one sensitive layer consisting of a plurality of silver halide emulsion layers sensitive to essentially the same color but different in sensitivity. This sensitive layer is a unit sensitive layer sensitive to one of blue light, green light, and red light. In a multilayered silver halide color photographic lightsensitive material, unit sensitive layers are generally arranged in the order of red-, green-, and blue-sensitive layers from a support. However, according to the intended use, this order of arrangement can be reversed, or sensitive layers sensitive to the same color can sandwich another sensitive layer sensitive to a different color. Non-sensitive layers can be formed between the silver halide sensitive layers and as the uppermost layer and the lowermost layer. These non-sensitive layers can contain, e.g., couplers, DIR compounds, and color-mixing inhibitors to be described later. As a plurality of silver halide emulsion layers constituting each unit sensitive layer, as described in DE1,121,470 or GB923,045, the disclosures of which are incorporated herein by reference, high- and low-speed emulsion layers are preferably arranged such that the sensitivity is sequentially decreased toward a support. Also, as described in Jpn. Pat. Appln. KOKAI Publication No. (hereinafter referred to as JP-A-)57-112751, JP-A-62-200350, JP-A-62-206541, and JP-A-62-206543, the disclosures of which are incorporated herein by reference, layers can be arranged such that a low-speed emulsion layer is formed apart from a support and a high-speed layer is formed close to the support.

More specifically, layers can be arranged from the farthest side from a support in the order of low-speed blue-sensitive layer (BL)/high-speed blue-sensitive layer (BH)/high-speed green-sensitive layer (GH)/low-speed green-sensitive layer (GL)/high-speed red-sensitive layer (RH)/low-speed red-sensitive layer (RL), the order of BH/BL/GL/GH/RH/RL, or the order of BH/BL/GH/GL/RL/RH.

In addition, as described in Jpn. Pat. Appln. KOKOKU Publication No. (hereinafter referred to as JP-B-)55-34932, the disclosure of which is incorporated herein by reference, layers can be arranged from the farthest side from a support in the order of blue-sensitive layer/GH/RH/GL/RL. Furthermore, as described in JP-A-56-25738 and JP-A-62-63936, the disclosures of which are incorporated herein by reference, layers can be arranged from the farthest side from a support in the order of blue-sensitive layer/GL/RL/GH/RH.

As described in JP-B-49-15495, the disclosure of which is incorporated herein by reference, three layers can be arranged such that a silver halide emulsion layer having the highest sensitivity is arranged as an upper layer, a silver halide emulsion layer having sensitivity lower than that of the upper layer is arranged as an interlayer, and a silver halide emulsion layer having sensitivity lower than that of the interlayer is arranged as a lower layer, i.e., three layers having different sensitivities can be arranged such that the sensitivity is sequentially decreased toward a support. When a layer structure is thus constituted by three layers having different sensitivities, these layers can be arranged, in a layer sensitive to one color, in the order of medium-speed emulsion layer/high-speed emulsion layer/low-speed emulsion layer from the farthest side from a support as described in JP-A-59-202464, the disclosure of which is incorporated herein by reference.

In addition, the order of high-speed emulsion layer/low-speed emulsion layer/medium-speed emulsion layer or low-speed emulsion layer/medium-speed emulsion layer/high-speed emulsion layer can be used. Furthermore, the arrangement can be changed as described above even when four or more layers are formed.

To improve the color reproduction, as described in U.S. Pat. Nos. 4,663,271, 4,705,744, 4,707,436, JP-A-62-160448, and JP-A-63-89850, the disclosures of which are incorporated herein by reference, a donor layer (CL) with an interlayer effect, which has a different spectral sensitivity distribution from that of a main sensitive layer such as BL, GL, or RL, is preferably formed adjacent to, or close to, this main sensitive layer.

A silver halide used in the present invention is silver iodobromide, silver iodochloride, or silver bromochloroiodide containing about 30 mol % or less of silver iodide. A silver halide is most preferably silver iodobromide or silver bromochloroiodide containing about 2 to about 10 mol % of silver iodide.

Silver halide grains contained in a photographic emulsion can have regular crystals such as cubic, octahedral, or tetradecahedral crystals, irregular crystals such as spherical or tabular crystals, crystals having crystal defects such as twin planes, or composite shapes thereof.

A silver halide can consist of fine grains having a grain size of about 0.2 μm or less or large grains having a projected area diameter of about 10 μm, and an emulsion can be either a polydisperse or monodisperse emulsion.

A silver halide photographic emulsion which can be used in the present invention can be prepared by methods described in, e.g., "I. Emulsion preparation and types," Research Disclosure (RD) No. 17643 (December, 1978), pp. 22 and 23, RD No. 18716 (November, 1979), page 648, and RD No. 307105 (November, 1989), pp. 863 to 865; P. Glafkides, "Chemie et Phisique Photographiques", Paul Montel, 1967; G. F. Duffin, "Photographic Emulsion Chemistry", Focal Press, 1966; and V. L. Zelikman et al., "Making and Coating Photographic Emulsion", Focal Press, 1964, the disclosures of which are incorporated herein by reference.

Monodisperse emulsions described in, e.g., U.S. Pat. Nos. 3,574,628, 3,655,394, and GB1,413,748 are also preferable, the disclosures of which are incorporated herein by reference.

Tabular grains having an aspect ratio of 3 or more can also be used in the present invention. Tabular grains can be easily prepared by methods described in Gutoff, "Photographic Science and Engineering", Vol. 14, pp. 248 to 257 (1970); and U.S. Pat. Nos. 4,434,226, 4,414,310, 4,433,048, 4,439,520, and GB2,112,157, the disclosures of which are incorporated herein by reference.

A crystal structure can be uniform, can have different halogen compositions in the interior and the surface layer thereof, or can be a layered structure. Alternatively, a silver halide having a different composition can be bonded by an epitaxial junction or a compound except for a silver halide such as silver rhodanide or zinc oxide can be bonded. A mixture of grains having various types of crystal shapes can also be used.

The above emulsion can be any of a surface latent image type emulsion which mainly forms a latent image on the surface of a grain, an internal latent image type emulsion which forms a latent image in the interior of a grain, and another type of emulsion which has latent images on the surface and in the interior of a grain. However, the emulsion must be a negative type emulsion. The internal latent image type emulsion can be a core/shell internal latent image type emulsion described in JP-A-63-264740, the disclosure of which is incorporated herein by reference. A method of preparing this core/shell internal latent image type emulsion is described in JP-A-59-133542, the disclosure of which is incorporated herein by reference. Although the thickness of a shell of this emulsion depends on, e.g., development conditions, it is preferably 3 to 40 nm, and most preferably, 5 to 20 nm.

A silver halide emulsion layer is normally subjected to physical ripening, chemical ripening, and spectral sensitization steps before it is used. Additives for use in these steps are described in RD Nos. 17643, 18716, and 307105, the disclosures of which are incorporated herein by reference, and they are summarized in a table to be presented later.

In a sensitive material of the present invention, it is possible to mix, in a single layer, two or more types of emulsions different in at least one of the characteristics of a sensitive silver halide emulsion, i.e., the grain size, grain size distribution, halogen composition, grain shape, and sensitivity.

It is also possible to preferably use surface-fogged silver halide grains described in U.S. Pat. No. 4,082,553, internally fogged silver halide grains described in U.S. Pat. No. 4,626,498 and JP-A-59-214852, and colloidal silver, in sensitive silver halide emulsion layers and/or substantially non-sensitive hydrophilic colloid layers, the disclosures of which are incorporated herein by reference. The internally fogged or surface-fogged silver halide grain means a silver halide grain which can be developed uniformly (non-imagewise) regardless of whether the location is a non-exposed portion or an exposed portion of a sensitive material. A method of preparing the internally fogged or surface-fogged silver halide grain is described in U.S. Pat. No. 4,626,498 and JP-A-59-214852, the disclosures of which are incorporated herein by reference. A silver halide which forms the internal core of an internally fogged core/shell type silver halide grain can have a different halogen composition. As the internally fogged or surface-fogged silver halide, any of silver chloride, silver chlorobromide, silver bromoiodide, and silver bromochloroiodide can be used. The average grain size of these fogged silver halide grains is preferably 0.01 to 0.75 μm, and most preferably, 0.05 to 0.6 μm. The grain shape can be a regular grain shape. Although the emulsion can be a polydisperse emulsion, it is preferably a monodisperse emulsion (in which at least 95% in weight or number of grains of silver halide grains have grain sizes falling within the range of ±40% of the average grain size).

In the present invention, it is preferable to use a non-sensitive fine grain silver halide. The non-sensitive fine grain silver halide preferably consists of silver halide grains which are not exposed during imagewise exposure for obtaining a dye image and are not substantially developed during development. These silver halide grains are preferably not fogged in advance. In the fine grain silver halide, the content of silver bromide is 0 to 100 mol %, and silver chloride and/or silver iodide can be added if necessary. The fine grain silver halide preferably contains 0.5 to 10 mol % of silver iodide. The average grain size (the average value of equivalent-circle diameters of projected areas) of the fine grain silver halide is preferably 0.01 to 0.5 μm, and more preferably, 0.02 to 0.2 μm.

The fine grain silver halide can be prepared following the same procedures as for a common sensitive silver halide. The surface of each silver halide grain need not be optically sensitized nor spectrally sensitized. However, before the silver halide grains are added to a coating solution, it is preferable to add a well-known stabilizer such as a triazole-based compound, azaindene-based compound, benzothiazolium-based compound, mercapto-based compound, or zinc compound. Colloidal silver can be added to this fine grain silver halide grain-containing layer.

The silver coating amount of a sensitive material of the present invention is preferably 6.0 $g/m^2$ or less, and most preferably, 4.5 $g/m^2$ or less.

Photographic additives usable in the present invention are also described in RDs, the disclosures of which are incorporated herein by reference, and the relevant portions are summarized in the following table.

| Additives | RD17643 | RD18716 | RD307105 |
|---|---|---|---|
| 1. Chemical sensitizers | page 23 | page 648, right column | page 866 |
| 2. Sensitivity increasing agents | | page 648, right column | |
| 3. Spectral sensitizers, super sensitizers | pages 23–24 | page 648, right column to page 649, right column | pages 866–868 |
| 4. Brighteners | page 24 | page 647, right column | page 868 |
| 5. Light absorbers, filter dyes, ultraviolet absorbers | pages 25–26 | page 649, right column to page 650, left column | page 873 |
| 6. Binders | page 26 | page 651, left column | pages 873–874 |
| 7. Plasticizers, lubricants | page 27 | page 650, right column | page 876 |
| 8. Coating aids, surface active agents | pages 26–27 | page 650, right column | pages 875–876 |
| 9. Antistatic agents | page 27 | page 650, right column | pages 876–877 |
| 10. Matting agents | | | pages 878–879 |

Various dye forming couplers can be used in a sensitive material of the present invention, and the following couplers are particularly preferable.

Yellow couplers: couplers represented by formulas (I) and (II) in EP502,424A; couplers (particularly Y-28 on page 18) represented by formulas (1) and (2) in EP513,496A; a coupler represented by formula (I) in claim 1 of EP568,037A; a coupler represented by formula (I) in column 1, lines 45 to 55 of U.S. Pat. No. 5,066,576; a coupler represented by formula (I) in paragraph 0008 of JP-A-4-274425; couplers (particularly D-35 on page 18) described in claim 1 on page 40 of EP498,381A1; couplers (particularly Y-1 (page 17) and Y-54 (page 41)) represented by formula (Y) on page 4 of EP447,969A1; and couplers (particularly II-17 and II-19 (column 17), and II-24 (column 19)) represented by formulas (II) to (IV) in column 7, lines 36 to 58 of U.S. Pat. No. 4,476,219.

Magenta couplers: L-57 (page 11, lower right column), L-68 (page 12, lower right column), and L-77 (page 13, lower right column) in JP-A-3-39737; A-4-63 (page 134), and A-4-73 and A-4-75 (page 139) in EP456,257; M-4 and M-6 (page 26), and M-7 (page 27) in EP486,965; M-45 (page 19) in EP571,959A; (M-1) (page 6) in JP-A-5-204106; and M-22 in paragraph 0237 of JP-A-4-362631.

Cyan couplers: CX-1, CX-3, CX-4, CX-5, CX-11, CX-12, CX-14, and CX-15 (pages 14 to 16) in JP-A-4-204843; C-7 and C-10 (page 35), C-34 and C-35 (page 37), and (I-1) and (I-17) (pages 42 and 43) in JP-A-4-43345; and couplers represented by formulas (Ia) and (Ib) in claim 1 of JP-A-6-67385.

Polymer couplers: P-1 and P-5 (page 11) in JP-A-2-44345.

Couplers for forming a colored dye with proper diffusibility are preferably those described in U.S. Pat. No. 4,366,237, GB2,125,570, EP96,873B, and DE3,234,533.

Couplers for correcting unnecessary absorption of a colored dye are preferably yellow colored cyan couplers (particularly YC-86 on page 84) represented by formulas (CI), (CII), (CIII), and (CIV) described on page 5 of EP456,257A1; yellow colored magenta couplers ExM-7 (page 202), EX-1 (page 249), and EX-7 (page 251) in EP456,257A1; magenta colored cyan couplers CC-9 (column 8) and CC-13 (column 10) described in U.S. Pat. No. 4,833,069; (2) (column 8) in U.S. Pat. No. 4,837,136; and colorless masking couplers (particularly compound examples on pages 36 to 45) represented by formula (A) in claim 1 of WO92/11575.

Examples of couplers which release a photographically useful group are as follows. Development inhibitor release compounds: compounds (particularly T-101 (page 30), T-104 (page 31), T-113 (page 36), T-131 (page 45), T-144 (page 51), and T-158 (page 58)) represented by formulas (I), (II), (III), (IV) described on page 11 of EP378,236A1, compounds (particularly D-49 (page 51)) represented by formula (I) described on page 7 of EP436,938A2, compounds (particularly (23) (page 11)) represented by formula (1) in EP568,037A, and compounds (particularly I-(1) on page 29) represented by formulas (I), (II), and (III) described on pages 5 and 6 of EP440,195A2; bleaching accelerator release compounds: compounds (particularly (60) and (61) on page 61) represented by formulas (I) and (I') on page 5 of EP310,125A2, and compounds (particularly (7) (page 7)) represented by formula (I) in claim 1 of JP-A-6-59411; ligand release compounds: compounds (particularly compounds in column 12, lines 21 to 41) represented by LIG-X described in claim 1 of U.S. Pat. No. 4,555,478; leuco dye release compounds: compounds 1 to 6 in columns 3 to 8 of U.S. Pat. No. 4,749,641; fluorescent dye release compounds: compounds (particularly compounds 1 to 11 in columns 7 to 10) represented by COUP-DYE in claim 1 of U.S. Pat. No. 4,774,181; development accelerator or fogging agent release compounds: compounds (particularly (I-22) in column 25) represented by formulas (1), (2), and (3) in column 3 of U.S. Pat. No. 4,656,123, and ExZK-2 on page 75, lines 36 to 38 of EP450,637A2; compounds which release a group which does not function as a dye unless it splits off: compounds (particularly Y-1 to Y-19 in columns 25 to 36) represented by formula (I) in claim 1 of U.S. Pat. No. 4,857,447.

Preferred examples of additives other than couplers are as follows.

Dispersants of an oil-soluble organic compound: P-3, P-5, P-16, P-19, P-25, P-30, P-42, P-49, P-54, P-55, P-66, P-81, P-85, P-86, and P-93 (pages 140 to 144) in JP-A-62-215272; impregnating latexes of an oil-soluble organic compound: latexes described in U.S. Pat. No. 4,199,363; developing agent oxidized form scavengers: compounds (particularly I-(1), I-(2), I-(6), and I-(12) (columns 4 and 5)) represented by formula (I) in column 2, lines 54 to 62 of U.S. Pat. No. 4,978,606, and formulas (particularly a compound 1 (column 3)) in column 2, lines 5 to 10 of U.S. Pat. No. 4,923,787; stain inhibitors: formulas (I) to (III) on page 4, lines 30 to 33, particularly I-47, I-72, III-1, and III-27 (pages 24 to 48) in EP298321A; discoloration inhibitors: A-6, A-7, A-20, A-21, A-23, A-24, A-25, A-26, A-30, A-37, A-40, A-42, A-48, A-63, A-90, A-92, A-94, and A-164 (pages 69 to 118) in EP298321A, II-1 to III-23, particularly III-10 in columns 25 to 38 of U.S. Pat. No. 5,122,444, I-1 to III-4, particularly II-2 on pages 8 to 12 of EP471347A, and A-1 to A-48, particularly A-39 and A-42 in columns 32 to 40 of U.S. Pat. No. 5,139,931; materials which reduce the use amount of a color enhancer or a color-mixing inhibitor: I-1 to II-15, particularly I-46 on pages 5 to 24 of EP411324A; formalin scavengers: SCV-1 to SCV-28, particularly SCV-8 on pages 24 to 29 of EP477932A; film hardeners: H-1, H-4, H-6, H-8, and H-14 on page 17 of JP-A-1-214845, compounds (H-1 to H-54) represented by formulas (VII) to (XII) in columns 13 to 23 of U.S. Pat. No. 4,618,573, compounds (H-1 to H-76), particularly H-14 represented by formula (6) on page 8, lower right column of JP-A-2-214852, and compounds described in claim 1 of U.S. Pat. No. 3,325,287; development inhibitor precursors: P-24, P-37, and P-39 (pages 6 and 7) in JP-A-62-168139; compounds described in claim 1, particularly 28 and 29 in column 7 of U.S. Pat. No. 5,019,492; antiseptic agents and mildewproofing agents: I-1 to III-43, particularly II-1, II-9, II-10, II-18, and III-25 in columns 3 to 15 of U.S. Pat. No. 4,923,790; stabilizers and antifoggants: I-1 to (14), particularly I-1, I-60, (2), and (13) in columns 6 to 16 of U.S. Pat. No. 4,923,793, and compounds 1 to 65, particularly a compound 36 in columns 25 to 32 of U.S. Pat. No. 4,952,483; chemical sensitizers: triphenylphosphine selenide and a compound 50 in JP-A-5-40324; dyes: a-1 to b-20, particularly a-1, a-12, a-18, a-27, a-35, a-36, and b-5 on pages 15 to 18 and V-1 to V-23, particularly V-1 on pages 27 to 29 of JP-A-3-156450, F-I-1 to F-II-43, particularly F-I-11 and F-II-8 on pages 33 to 55 of EP445627A, III-1 to III-36, particularly III-1 and III-3 on pages 17 to 28 of EP457153A, fine crystal dispersions of Dye-1 to Dye-124 on pages 8 to 26 of WO88/04794, compounds 1 to 22, particularly a compound 1 on pages 6 to 11 of EP319999A, compounds D-1 to D-87 (pages 3 to 28) represented by formulas (1) to (3) in EP519306A, compounds 1 to 22 (columns 3 to 10) represented by formula (I) in U.S. Pat. No. 4,268,622, and compounds (1) to (31) (columns 2 to 9) represented by formula (I) in U.S. Pat. No. 4,923,788; UV absorbers: compounds (18b) to (18r) and 101 to 427 (pages 6 to 9) represented by formula (1) in JP-A-

46-3335, compounds (3) to (66) (pages 10 to 44) represented by formula (I) and compounds HBT-1 to HBT-10 (page 14) represented by formula (III) in EP520938A, and compounds (1) to (31) (columns 2 to 9) represented by formula (1) in EP521823A.

The present invention can be applied to various color sensitive materials such as color negative films for general purposes or motion pictures, color reversal films for slides or television, color paper, color positive films, and color reversal paper. The present invention is also suited to film units with lens described in JP-B-2-32615 and Jpn. UM Appln. KOKOKU Publication No. 3-39784.

A support which can be suitably used in the present invention is described in, e.g., RD. No. 17643, page 28, RD. No. 18716, page 647, right column to page 648, left column, and RD. No. 307105, page 879.

In a sensitive material of the present invention, the total film thickness of all hydrophilic colloid layers on the side having emulsion layers is preferably 28 μm or less, more preferably, 23 μm or less, further preferably, 18 μm or less, and particularly preferably, 16 μm or less. A film swell speed $T_{1/2}$ is preferably 30 sec or less, and more preferably, 20 sec or less. $T_{1/2}$ is defined as a time which the film thickness requires to reach ½ of a saturation film thickness which is 90% of a maximum swell film thickness reached when processing is performed by using a color developer at 30° C. for 3 min and 15 sec. A film thickness means the thickness of a film measured under moisture conditioning at a temperature of 25° C. and a relative humidity of 55% (two days). $T_{1/2}$ can be measured by using a swell meter described in Photogr. Sci. Eng., A. Green et al., Vol. 19, No. 2, pp. 124 to 129. $T_{1/2}$ can be adjusted by adding a film hardening agent to gelatin as a binder or changing aging conditions after coating. The swell ratio is preferably 150 to 400%. The swell ratio can be calculated from the maximum swell film thickness under the conditions mentioned above by using formula: (maximum swell film thickness—film thickness)/film thickness.

In a sensitive material of the present invention, hydrophilic colloid layers (to be referred to as back layers hereinafter) having a total dried film thickness of 2 to 20 μm are preferably formed on the side opposite to the side having emulsion layers. The back layers preferably contain the aforementioned light absorbers, filter dyes, ultraviolet absorbers, antistatic agents, film hardeners, binders, plasticizers, lubricants, coating aids, and surfactants. The swell ratio of the back layers is preferably 150 to 500%.

A sensitive material of the present invention can be developed by conventional methods described in RD. No. 17643, pp. 28 and 29, RD. No. 18716, page 651, left to right columns, and RD No. 307105, pp. 880 and 881.

Color negative film processing solutions used in the present invention will be described below.

Compounds described in JP-A-4-121739, page 9, upper right column, line 1 to page 11, lower left column, line 4 can be used in a color developer of the present invention. As a color developing agent used when particularly rapid processing is to be performed, 2-methyl-4-[N-ethyl-N-(2-hydroxyethyl)amino]aniline, 2-methyl-4-[N-ethyl-N-(3-hydroxypropyl)amino]aniline, or 2-methyl-4-[N-ethyl-N-(4-hydroxybutyl)amino]aniline is preferable.

The use amount of any of these color developing agents is preferably 0.01 to 0.08 mol, more preferably, 0.015 to 0.06 mol, and most preferably, 0.02 to 0.05 mol per liter (to be also referred to as "L" hereinafter) of a color developer. Also, a replenisher of a color developer preferably contains a color developing agent at a concentration 1.1 to 3 times, particularly 1.3 to 2.5 times the above concentration.

As a preservative of a color developer, hydroxylamine can be extensively used. If higher preservability is necessary, the use of a hydroxylamine derivative having a substituent such as an alkyl group, hydroxyalkyl group, sulfoalkyl group, or carboxyalkyl group is preferable. Preferred examples are N,N-di(sulfoethyl)hydroxylamine, monomethylhydroxylamine, dimethylhydroxylamine, monoethylhydroxylamine, diethylhydroxylamine, and N,N-di(carboxylethyl)hydroxylamine. Of these derivatives, N,N-di(sulfoethyl)hydroxylamine is particularly preferable. Although these derivatives can be used together with hydroxylamine, it is preferable to use one or two types of these derivatives instead of hydroxylamine.

The use amount of a preservative is preferably 0.02 to 0.2 mol, more preferably, 0.03 to 0.15 mol, and most preferably, 0.04 to 0.1 mol per L of a color developer. As in the case of a color developing agent, a replenisher preferably contains a preservative at a concentration 1.1 to 3 times that of a mother solution (processing tank solution).

A color developer contains sulfite as an agent for preventing an oxide of a color developing agent from changing into tar. The use amount of this sulfite is preferably 0.01 to 0.05 mol, and more preferably, 0.02 to 0.04 mol per L of a color developer. In a replenisher, sulfite is preferably used at a concentration 1.1 to 3 times the above concentration.

The pH of a color developer is preferably 9.8 to 11.0, and more preferably, 10.0 to 10.5. In a replenisher, the pH is preferably set to be higher by 0.1 to 1.0 than these values. To stably maintain this pH, a known buffering agent such as carbonate, phosphate, sulfosalicylate, or borate is used.

The replenishment rate of a color developer is preferably 80 to 1,300 per $m^2$ of a sensitive material. However, the replenishment rate is preferably smaller in order to reduce environmental pollution. For example, the replenishment rate is preferably 80 to 600 mL, and more preferably, 80 to 400 mL.

The bromide ion concentration in a color developer is usually 0.01 to 0.06 mol per L of the color developer. However, this bromide ion concentration is preferably set at 0.015 to 0.03 mol per L of the color developer in order to suppress fog and improve the discrimination and graininess while maintaining the sensitivity. To set the bromide ion concentration in this range, it is only necessary to add bromide ions calculated by the following equation to a replenisher. If C takes a negative value, however, no bromide ions are preferably added to a replenisher.

$$C=A-W/V$$

where

C: the bromide ion concentration (mol/L) in a color developer replenisher

A: the target bromide ion concentration (mol/L) in a color developer

W: the amount (mol) of bromide ions dissolving into a color developer from 1 $m^2$ of a sensitive material when the sensitive material is color-developed V: the replenishment rate (L) of a color developer replenisher per 1 $m^2$ of a sensitive material As a method of increasing the sensitivity when the replenishment rate is decreased or high bromide ion concentration is set, it is preferable to use a development accelerator such as pyrazolidones represented by 1-phenyl-3-pyrazolidone and 1-phenyl-2-methyl-2-hydroxylmethyl- 3-pyrazolidone, or a thioether compound represented by 3,6-dithia-1,8-octanediol.

Compounds and processing conditions described in JP-A-4-125558, page 4, lower left column, line 16 to page 7, lower left column, line 6 can be applied to a processing solution having bleaching capacity in the present invention.

This bleaching agent preferably has an oxidation-reduction potential of 150 mV or more. Preferable practical examples of the bleaching agent are described in JP-A-5-72694 and JP-A-5-173312. In particular, 1,3-diaminopropane tetraacetic acid and ferric complex salt of a compound as practical example 1 in JP-A-5-173312, page 7 are preferable.

To improve the biodegradability of a bleaching agent, it is preferable to use compound ferric complex salts described in JP-A-4-251845, JP-A-4-268552, EP588,289, EP591,934, and JP-A-6-208213 as the bleaching agent. The concentration of any of these bleaching agents is preferably 0.05 to 0.3 mol per L of a solution having bleaching capacity. To reduce the amount of waste to the environment, the concentration is preferably designed to be 0.1 to 0.15 mol per L of the solution having bleaching capacity. When the solution having bleaching capacity is a bleaching solution, preferably 0.2 to 1 mol, and more preferably, 0.3 to 0.8 mol of a bromide is added per L of the bleaching solution.

A replenisher of the solution having bleaching capacity basically contains components at concentrations calculated by the following equation. This makes it possible to maintain the concentrations in a mother solution constant.

$$CR=CT\times(V1+V2)/V1+CP$$

where

CR: the concentrations of components in a replenisher

CT: the concentrations of components in a mother solution (processing tank solution)

CP: the concentrations of components consumed during processing

V1: the replenishment rate (mL) of a replenisher having bleaching capacity per $m^2$ of a sensitive material V2: the amount (mL) carried over from a pre-bath by $m^2$ of a sensitive material Additionally, a bleaching solution preferably contains a pH buffering agent, and more preferably contains succinic acid, maleic acid, malonic acid, glutaric acid, adipic acid, or dicarboxylic acid with little odor. Also, the use of known bleaching accelerators described in JP-A-53-95630, RD No. 17129, and U.S. Pat. No. 3,893,858 is preferable.

It is preferable to replenish 50 to 1,000 mL of a bleaching replenisher to a bleaching solution per $m^2$ of a sensitive material. The replenishment rate is more preferably 80 to 500 mL, and most preferably, 100 to 300 mL. Aeration of a bleaching solution is also preferable.

Compounds and processing conditions described in JP-A-4-125558, page 7, lower left column, line 10 to page 8, lower right column, line 19 can be applied to a processing solution with fixing capacity.

In particular, to improve the fixing rate and preservability, compounds represented by formulas (I) and (II) described in JP-A-6-301169 are preferably added singly or together to a processing solution with fixing capacity. To improve the preservability, the use of sulfinic acid such as p-toluenesulfinate described in JP-A-1-224762 is also preferable.

To improve the desilvering characteristics, ammonium is preferably used as cation in a solution with bleaching capacity or a solution with fixing capacity. However, the amount of ammonium is preferably reduced, or zero, to reduce environmental pollution.

In the bleaching, bleach-fixing, and fixing steps, it is particularly preferable to perform jet stirring described in JP-A-1-309059.

The replenishment rate of a replenisher in the bleach-fixing or fixing step is preferably 100 to 1,000 mL, more preferably, 150 to 700 mL, and most preferably, 200 to 600 mL per $m^2$ of a sensitive material.

In the bleach-fixing or fixing step, an appropriate silver collecting apparatus is preferably installed either in-line or off-line to collect silver. When the apparatus is installed in-line, processing can be performed while the silver concentration in a solution is reduced, so the replenishment rate can be reduced. It is also preferable to install the apparatus off-line to collect silver and reuse the residual solution as a replenisher.

The bleach-fixing or fixing step can be performed by using a plurality of processing tanks, and these tanks are preferably cascaded to form a multistage counterflow system. To balance the system with the size of a processor, a two-tank cascade system is generally efficient. The processing time ratio of the front tank to the rear tank is preferably 0.5:1 to 1:0.5, and more preferably, 0.8:1 to 1:0.8.

In a bleach-fixing or fixing solution, the presence of free chelating agents which are not metal complexes is preferable to improve the preservability. As these chelating agents, the use of the biodegradable chelating agents previously described in connection to a bleaching solution is preferable.

Contents described in aforementioned JP-A-4-125558, page 12, lower right column, line 6 to page 13, lower right column, line 16 can be preferably applied to the washing and stabilization steps. To improve the safety of the work environment, it is preferable to use azolylmethylamines described in EP504,609 and EP519,190 or N-methylolazoles described in JP-A-4-362943 instead of formaldehyde in a stabilizer and to make a magenta coupler divalent to form a solution of surfactant containing no image stabilizing agent such as formaldehyde.

To reduce adhesion of dust to a magnetic recording layer formed on a sensitive material, a stabilizer described in JP-A-6-289559 can be preferably used.

The replenishment rate of washing water and a stabilizer is preferably 80 to 1,000 mL, more preferably, 100 to 500 mL; and most preferably, 150 to 300 mL per $m^2$ of a sensitive material in order to maintain the washing and stabilization functions and at the same time reduce the waste liquors for environmental protection. In processing performed with this replenishment rate, it is preferable to prevent the propagation of bacteria and mildew by using known mildewproofing agents such as thiabendazole, 1,2-benzoisothiazoline-3-one, and 5-chloro-2-methylisothiazoline-3-one, antibiotics such as gentamicin, and water deionized by an ion exchange resin or the like. It is more effective to use deionized water together with a mildewproofing agent or an antibiotic.

The replenishment rate of a solution in a washing water tank or stabilizer tank is preferably reduced by performing reverse osmosis membrane processing described in JP-A-3-46652, JP-A-3-53246, JP-A-3-55542, JP-A-3-121448, and JP-A-3-126030. A reverse osmosis membrane used in this processing is preferably a low-pressure reverse osmosis membrane.

In the processing of the present invention, it is particularly preferable to perform evaporation correction of processing solution disclosed in JIII Journal of Technical Disclosure No. 94-4992. In particular, a method of performing correction on the basis of (formula-1) on page 2 by using temperature and humidity information of an environment in which a processor is installed is preferable. Water for use in this evaporation correction is preferably taken from the washing water replenishment tank. If this is the case, deionized water is preferably used as the washing replenishing water.

Processing agents described in aforementioned JIII Journal of Technical Disclosure No. 94-4992, page 3, right column, line 15 to page 4, left column, line 32 are preferably used in the present invention. As a processor for these processing agents, a film processor described on page 3, right column, lines 22 to 28 is preferable.

Practical examples of processing agents, automatic processors, and evaporation correction methods suited to practicing the present invention are described in the same JIII Journal of Technical Disclosure No. 94-4992, page 5, right column, line 11 to page 7, right column, last line.

Processing agents used in the present invention can be supplied in any form: a liquid agent having the concentration of a solution to be used, concentrated liquid agent, granules, powder, tablets, paste, and emulsion, and the like. Examples of such processing agents are a liquid agent contained in a low-oxygen permeable vessel disclosed in JP-A-63-17453, vacuum-packed powders and granules disclosed in JP-A-4-19655 and JP-A-4-230748, granules containing a water-soluble polymer disclosed in JP-A-4-221951, tablets disclosed in JP-A-51-61837 and JP-A-6-102628, and a paste disclosed in PCT National Publication No. 57-500485. Although any of these processing agents can be preferably used, the use of a liquid previously adjusted to have the concentration of a solution to be used is preferable for the sake of convenience in use.

As a vessel for containing these processing agents, polyethylene, polypropylene, polyvinylchloride, polyethyleneterephthalate, and nylon are used singly or as a composite material. These materials are selected in accordance with the level of necessary oxygen permeability. For a readily oxidizable solution such as a color developer, a low-oxygen permeable material is preferable. As the low-oxygen permeable material, more specifically, polyethyleneterephthalate or a composite material of polyethylene and nylon is preferable. A vessel made of any of these materials preferably has a thickness of 500 to 1,500 μm and an oxygen permeability of 20 $mL/m^2 \cdot 24$ hrs·atm or less.

Color reversal film processing solutions used in the present invention will be described below.

Processing for a color reversal film is described in detail in Aztech Ltd., Known Technology No. 6 (1991, April 1), page 1, line 5 to page 10, line 5 and page 15, line 8 to page 24, line 2, and any of the contents can be preferably applied.

In this color reversal film processing, an image stabilizing agent is contained in a control bath or a final bath. Preferred examples of this image stabilizing agent are formalin, sodium formaldehyde bisulfite, and N-methylolazoles. Sodium formaldehyde bisulfite or N-methylolazoles are preferable in terms of work environment, and N-methyloltriazole is particularly preferable as N-methylolazoles. The contents pertaining to a color developer, bleaching solution, fixing solution, and washing water described in the color negative film processing can be preferably applied to the color reversal film processing.

Preferred examples of color reversal film processing agents containing the above contents are an E-6 processing agent manufactured by Eastman Kodak Co. and a CR-56 processing agent manufactured by Fuji Photo Film Co., Ltd.

EXAMPLE 1

The present invention will be described in detail below by way of its examples, but the invention is not limited to these examples.

Making of Sample 101

A multilayered color sensitive material including layers having the following compositions was formed on a 127-μm thick undercoated cellulose triacetate film support to make sample 101. Numbers represent addition amounts per $m^2$. Note that the effects of added compounds are not restricted to the described purposes.

| | | |
|---|---|---|
| 1st layer: Antihalation layer | | |
| Black colloidal silver | | 0.15 g |
| Gelatin | | 2.00 g |
| Ultraviolet absorber U-1 | | 0.15 g |
| Ultraviolet absorber U-3 | | 0.040 g |
| Ultraviolet absorber U-4 | | 0.20 g |
| High-boiling organic solvent Oil-1 | | 0.10 g |
| Dye D-4 | | 1.0 mg |
| Dye D-8 | | 2.5 mg |
| Fine crystal solid dispersion of dye E-1 | | 0.10 g |
| 2nd layer: Interlayer | | |
| Gelatin | | 0.30 g |
| Compound Cpd-C | | 0.5 mg |
| Compound Cpd-J | | 1.5 mg |
| Compound Cpd-K | | 4.0 mg |
| Compound Cpd-G | | 0.30 g |
| Ultraviolet absorber U-6 | | 0.02 g |
| High-boiling organic solvent Oil-3 | | 0.019 g |
| High-boiling organic solvent Oil-4 | | 0.020 g |
| High-boiling organic solvent Oil-5 | | 2.0 mg |
| High-boiling organic solvent Oil-7 | | 2.0 mg |
| High-boiling organic solvent Oil-8 | | 5.0 mg |
| Dye D-7 | | 2.5 mg |
| 3rd layer: Interlayer | | |
| Yellow colloidal silver | silver | 0.010 g |
| Gelatin | | 0.30 g |
| Compound Cpd-M | | 0.015 g |
| Compound Cpd-F | | 0.10 g |
| High-boiling organic solvent Oil-3 | | 0.050 g |
| 4th layer: Low-speed red-sensitive emulsion layer | | |
| Emulsion A | silver | 0.18 g |
| Emulsion B | silver | 0.20 g |
| Emulsion C | silver | 0.20 g |
| Gelatin | | 0.60 g |
| Coupler C-1 | | 0.14 g |
| Coupler C-2 | | 0.070 g |
| Coupler C-9 | | 0.010 g |
| Compound Cpd-C | | 5.0 mg |
| Compound Cpd-I | | 0.020 g |
| Compound Cpd-J | | 5.0 mg |
| High-boiling organic solvent Oil-2 | | 0.10 g |
| Additive P-1 | | 0.10 g |
| 5th layer: Medium-speed red-sensitive emulsion layer | | |
| Emulsion C | silver | 0.25 g |
| Emulsion D | silver | 0.20 g |
| Gelatin | | 0.70 g |
| Coupler C-1 | | 0.20 g |
| Coupler C-2 | | 0.15 g |
| High-boiling organic solvent Oil-2 | | 0.10 g |
| Additive P-1 | | 0.10 g |
| 6th layer: High-speed red-sensitive emulsion layer | | |
| Emulsion E | silver | 0.25 g |
| Emulsion F | silver | 0.25 g |
| Gelatin | | 1.30 g |
| Coupler C-1 | | 0.10 g |
| Coupler C-2 | | 0.050 g |
| Coupler C-3 | | 0.70 g |

-continued

| | | | |
|---|---|---|---|
| High-boiling organic solvent Oil-2 | | 0.10 | g |
| Compound Cpd-F | | 0.10 | g |
| Additive P-1 | | 0.10 | g |
| 7th layer: Interlayer | | | |
| Gelatin | | 0.60 | g |
| Additive P-2 | | 0.30 | g |
| Compound Cpd-I | | 2.6 | mg |
| Dye D-5 | | 0.020 | g |
| Dye D-6 | | 0.010 | g |
| Compound Cpd-M | | 0.040 | g |
| Compound Cpd-O | | 3.0 | mg |
| Compound Cpd-P | | 2.5 | mg |
| Compound Cpd-F | | 0.30 | g |
| High-boiling organic solvent Oil-1 | | 0.020 | g |
| High-boiling organic solvent Oil-6 | | 0.050 | g |
| 8th layer: Interlayer | | | |
| Yellow colloidal silver | silver | 0.010 | g |
| Gelatin | | 0.40 | g |
| Additive P-1 | | 0.05 | g |
| Compound Cpd-A | | 0.10 | g |
| Compound Cpd-M | | 0.10 | g |
| High-boiling organic solvent Oil-6 | | 0.10 | g |
| 9th layer: Low-speed green-sensitive emulsion layer | | | |
| Emulsion G | silver | 0.25 | g |
| Emulsion H | silver | 0.30 | g |
| Emulsion I | silver | 0.25 | g |
| Gelatin | | 1.00 | g |
| Coupler C-7 | | 0.80 | g |
| Coupler C-8 | | 0.50 | g |
| Coupler C-11 | | 0.080 | g |
| Compound Cpd-B | | 0.030 | g |
| Compound Cpd-D | | 0.020 | g |
| Compound Cpd-E | | 0.020 | g |
| Compound Cpd-G | | 2.5 | mg |
| Compound Cpd-F | | 0.040 | g |
| Compound Cpd-K | | 2.0 | mg |
| Compound Cpd-L | | 0.020 | g |
| High-boiling organic solvent Oil-1 | | 0.05 | g |
| High-boiling organic solvent Oil-2 | | 0.10 | g |
| 10th layer: Medium-speed green-sensitive emulsion layer | | | |
| Emulsion I | silver | 0.20 | g |
| Emulsion J | silver | 0.20 | g |
| Gelatin | | 0.50 | g |
| Coupler C-4 | | 0.10 | g |
| Coupler C-11 | | 0.070 | g |
| Compound Cpd-B | | 0.030 | g |
| Compound Cpd-D | | 0.020 | g |
| Compound Cpd-F | | 0.050 | g |
| Compound Cpd-G | | 2.0 | mg |
| High-boiling organic solvent Oil-2 | | 0.10 | g |
| 11th layer: High-speed green-sensitive emulsion layer | | | |
| Emulsion K | silver | 0.45 | g |
| Gelatin | | 0.60 | g |
| Coupler C-4 | | 0.20 | g |
| Coupler C-11 | | 0.10 | g |
| Compound Cpd-B | | 0.080 | g |
| Compound Cpd-D | | 0.020 | g |
| Compound Cpd-F | | 0.040 | g |
| Compound Cpd-K | | 5.0 | mg |
| High-boiling organic solvent Oil-2 | | 0.15 | g |
| 12th layer: Interlayer | | | |
| Gelatin | | 0.30 | g |
| Compound Cpd-M | | 0.05 | g |
| High-boiling organic solvent Oil-3 | | 0.025 | g |
| High-boiling organic solvent Oil-6 | | 0.025 | g |
| 13th layer: Yellow filter layer | | | |
| Yellow colloidal silver | silver | 5.0 | mg |
| Gelatin | | 1.00 | g |
| Compound Cpd-C | | 0.010 | g |
| Compound Cpd-M | | 0.030 | g |
| Compound Cpd-L | | 0.010 | g |
| High-boiling organic solvent Oil-1 | | 0.020 | g |

-continued

| | | | |
|---|---|---|---|
| Fine crystal solid dispersion of dye E-2 | | 0.030 | g |
| Fine crystal solid dispersion of dye E-3 | | 0.020 | g |
| 14th layer: Interlayer | | | |
| Gelatin | | 0.30 | g |
| 15th layer: Low-speed blue-sensitive emulsion layer | | | |
| Emulsion L | silver | 0.20 | g |
| Emulsion M | silver | 0.20 | g |
| Gelatin | | 0.80 | g |
| Coupler C-5 | | 0.20 | g |
| Coupler C-6 | | 0.10 | g |
| Coupler C-10 | | 0.13 | g |
| Compound Cpd-I | | 0.010 | g |
| Compound Cpd-M | | 0.010 | g |
| 16th layer: Medium-speed blue-sensitive emulsion layer | | | |
| Emulsion N | silver | 0.20 | g |
| Emulsion O | silver | 0.20 | g |
| Gelatin | | 0.90 | g |
| Coupler C-5 | | 0.10 | g |
| Coupler C-6 | | 0.10 | g |
| Coupler C-10 | | 0.13 | g |
| Compound Cpd-N | | 2.0 | mg |
| Compound Cpd-K | | 2.0 | mg |
| High-boiling organic solvent Oil-2 | | 0.050 | g |
| 17th layer: High-speed blue-sensitive emulsion layer | | | |
| Emulsion O | silver | 0.20 | g |
| Emulsion P | silver | 0.25 | g |
| Gelatin | | 1.20 | g |
| Coupler C-5 | | 0.10 | g |
| Coupler C-6 | | 0.10 | g |
| Coupler C-10 | | 0.90 | g |
| High-boiling organic solvent Oil-2 | | 0.10 | g |
| Compound Cpd-N | | 5.0 | mg |
| Compound Cpd-Q | | 0.20 | g |
| 18th layer: 1st protective layer | | | |
| Gelatin | | 0.70 | g |
| Ultraviolet absorber U-1 | | 0.20 | g |
| Ultraviolet absorber U-2 | | 0.050 | g |
| Ultraviolet absorber U-5 | | 0.30 | g |
| Compound Cpd-O | | 5.0 | mg |
| Compound Cpd-A | | 0.030 | g |
| Compound Cpd-H | | 0.20 | g |
| Dye D-1 | | 0.10 | g |
| Dye D-2 | | 0.050 | g |
| Dye D-3 | | 0.07 | g |
| High-boiling organic solvent Oil-3 | | 0.10 | g |
| 19th layer: 2nd protective layer | | | |
| Colloidal silver | silver | 0.10 | mg |
| Fine grain silver iodobromide emulsion (average grain size 0.06 μm, AgI content 1 mol%) | silver | 0.10 | g |
| Gelatin | | 0.50 | g |
| 20th layer: 3rd protective layer | | | |
| Gelatin | | 0.80 | g |
| Polymethylmethacrylate (average grain size 1.5 μm) | | 0.10 | g |
| 6:4 copolymer of methylmethacrylate and methacrylic acid (average grain size 1.5 μm) | | 0.10 | g |
| Silicone oil SO-1 | | 0.030 | g |
| Surfactant W-1 | | 3.0 | mg |
| Surfactant W-2 | | 0.030 | g |
| Surfactant W-7 | | 2.5 | mg |

In addition to the above compositions, additives F-1 to F-10 were added to all emulsion layers. Also, a gelatin hardener H-1 and surfactants W-3, W-4, W-5, and W-6 for coating and emulsification were added to each layer.

Furthermore, phenol, 1,2-benzisothiazoline-3-one, 2-phenoxyethanol, phenethylalcohol, and p-benzoic butylester were added as antiseptic and mildewproofing agents.

TABLE 1

Silver iodobromide emulsions used in sample 101 were as follows

| Emulsion | Characteristics | Sphere-equivalent average grain size (μm) | Variation coefficient (%) | AgI content (%) |
|---|---|---|---|---|
| A | Monodisperse tetradecahedral grain | 0.13 | 10 | 4.0 |
| B | Monodisperse cubic internal latent image type grain | 0.25 | 10 | 4.8 |
| C | Monodisperse tabular grain Average aspect ratio 2.0 | 0.30 | 15 | 3.8 |
| D | Monodisperse tabular grain Average aspect ratio 3.0 | 0.35 | 18 | 4.8 |
| E | Monodisperse tabular grain Average aspect ratio 3.0 | 0.40 | 15 | 2.0 |
| F | Monodisperse tabular grain Average aspect ratio 4.5 | 0.50 | 12 | 1.8 |
| G | Monodisperse cubic grain | 0.15 | 9 | 3.5 |
| H | Monodisperse cubic internal latent image type grain | 0.24 | 12 | 3.5 |
| I | Monodisperse tabular grain Average aspect ratio 4.0 | 0.30 | 17 | 3.5 |
| J | Monodisperse tabular grain Average aspect ratio 5.0 | 0.45 | 16 | 3.0 |
| K | Monodisperse tabular grain Average aspect ratio 5.5 | 0.60 | 13 | 3.3 |
| L | Monodisperse tetradecahedral grain | 0.33 | 10 | 4.5 |
| M | Monodisperse cubic grain | 0.33 | 9 | 4.5 |
| N | Monodisperse tabular grain Average aspect ratio 3.0 | 0.43 | 10 | 2.5 |
| O | Monodisperse tabular grain Average aspect ratio 6.0 | 0.75 | 9 | 2.0 |
| P | Monodisperse tabular grain Average aspect ratio 6.0 | 0.90 | 8 | 1.8 |

TABLE 2

Spectral sensitization of emulsions A to P

| Emulsion name | Added sensitizing dye | Addition amount (g) per mol of silver halide |
|---|---|---|
| A | S-1 | 0.010 |
| | S-2 | 0.25 |
| | S-3 | 0.010 |
| | S-13 | 0.025 |
| B | S-2 | 0.25 |
| | S-8 | 0.015 |
| | S-13 | 0.025 |
| C | S-2 | 0.20 |
| | S-8 | 0.030 |
| | S-13 | 0.025 |
| D | S-1 | 0.030 |
| | S-2 | 0.15 |
| | S-3 | 0.020 |
| | S-13 | 0.10 |
| E | S-1 | 0.020 |
| | S-2 | 0.15 |
| | S-8 | 0.020 |
| | S-13 | 0.10 |
| F | S-1 | 0.020 |
| | S-2 | 0.20 |
| | S-8 | 0.050 |
| | S-13 | 0.025 |
| G | S-4 | 0.35 |
| | S-5 | 0.10 |
| | S-12 | 0.05 |
| H | S-4 | 0.25 |
| | S-12 | 0.10 |
| I | S-4 | 0.25 |
| | S-5 | 0.10 |
| | S-12 | 0.15 |

TABLE 3

Spectral sensitization of emulsions A to P (continuation of Table 2)

| Emulsion name | Added sensitizing dye | Addition amount (g) per mol of silver halide |
|---|---|---|
| J | S-4 | 0.35 |
| | S-9 | 0.10 |
| | S-12 | 0.10 |
| K | S-4 | 0.30 |
| | S-5 | 0.050 |
| | S-9 | 0.050 |
| | S-12 | 0.15 |
| L | S-6 | 0.25 |
| | S-7 | 0.15 |
| | S-10 | 0.050 |
| M | S-6 | 0.10 |
| | S-10 | 0.15 |
| | S-11 | 0.25 |
| N | S-10 | 0.25 |
| | S-11 | 0.25 |
| O | S-6 | 0.10 |
| | S-10 | 0.20 |
| | S-11 | 0.25 |
| P | S-6 | 0.050 |
| | S-7 | 0.050 |
| | S-10 | 0.20 |
| | S-11 | 0.25 |

C-1
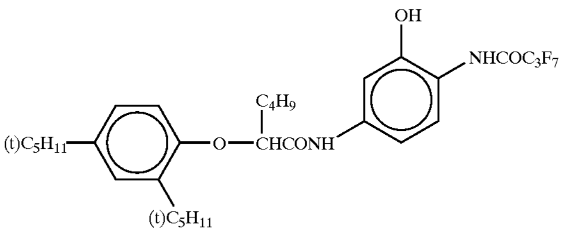
C-2
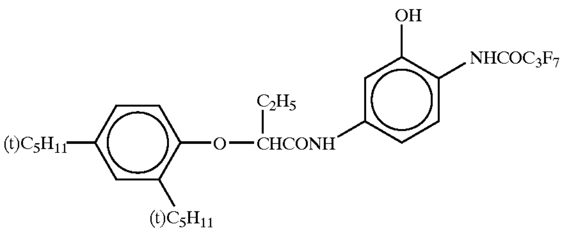
C-3
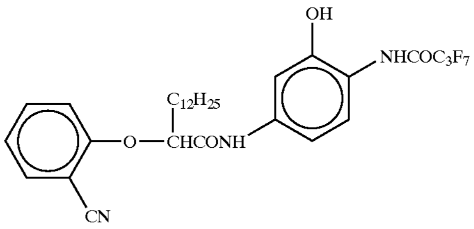
C-4
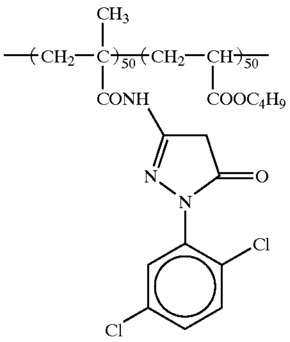
Numbers are expressed in weight %
Av. mol. wt.: about 25,000
C-5
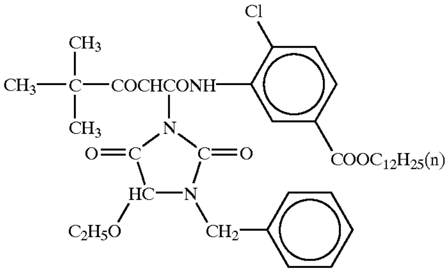
C-6
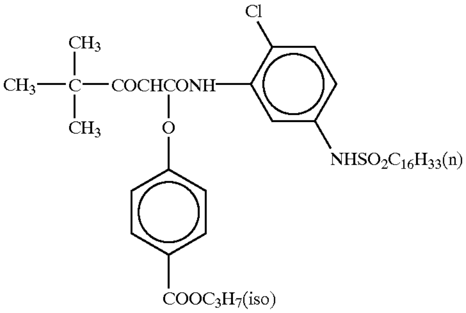
C-7
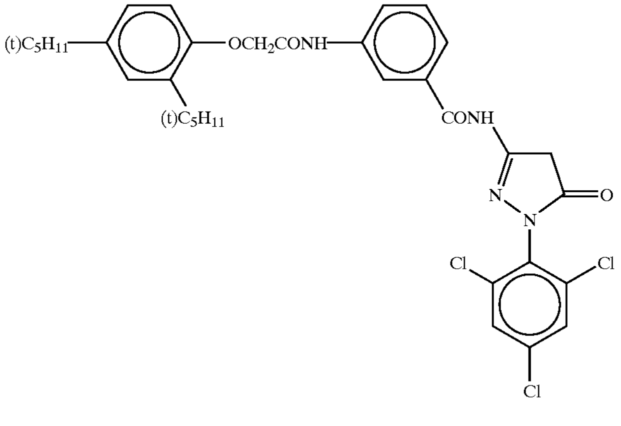

-continued
C-8
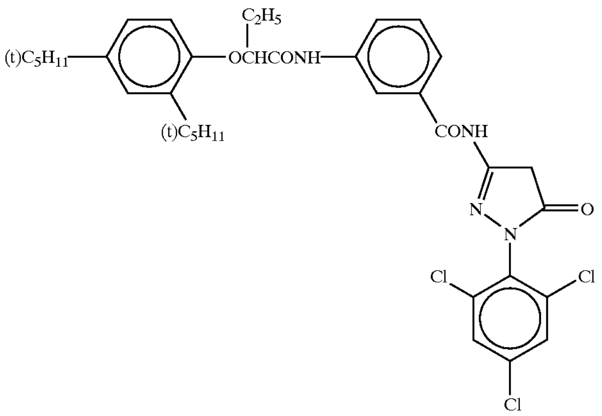
C-9
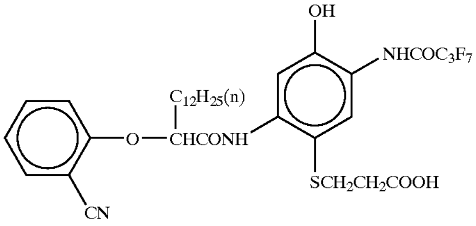
C-10
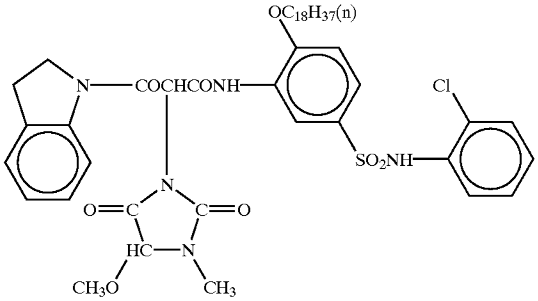
C-11
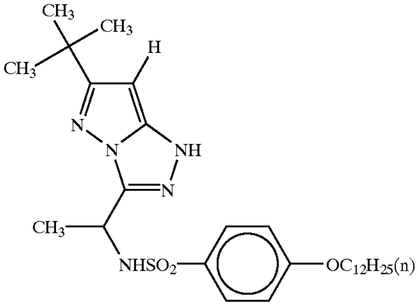
Oil-1
Dibutyl phthalate
Oil-2
Tricresyl phosphate
Oil-3
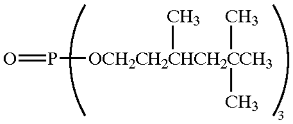
Oil-4
Tricyclohexyl phosphate
Oil-5
Dicyclohexyl phthalate
Oil-6
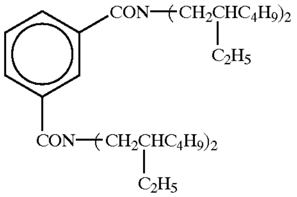
Oil-7
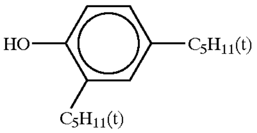
Oil-8
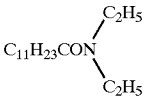
Oil-9
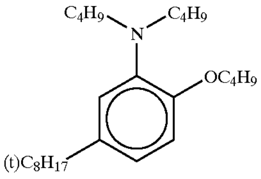

-continued
Cpd-A
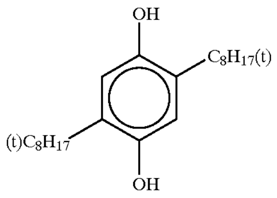
Cpd-B
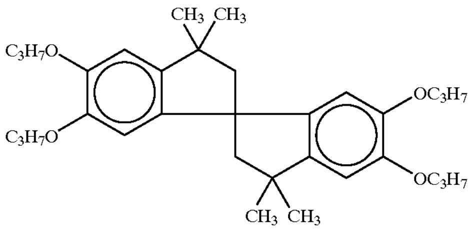
Cpd-C
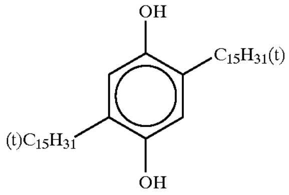
Cpd-D
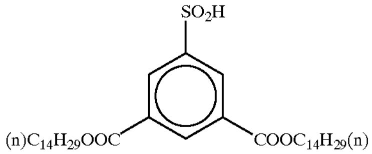
Cpd-E
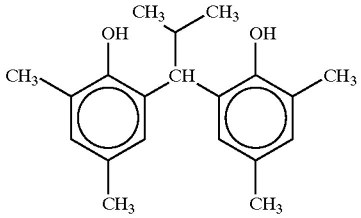
Cpd-F
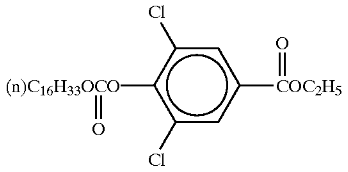
Cpd-G
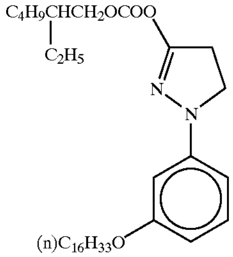
Cpd-H
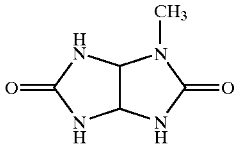
Cpd-I
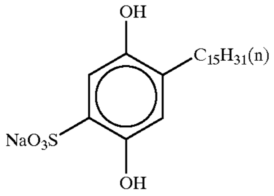
Cpd-M
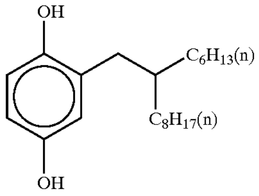
Cpd-J
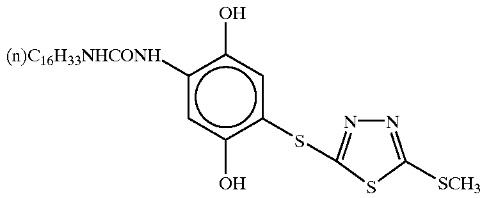
Cpd-K
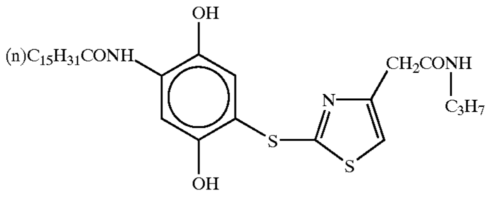
Cpd-L
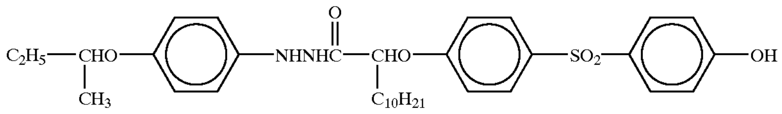
Cpd-N
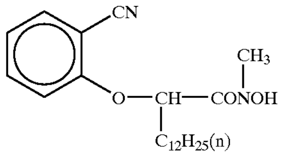
Cpd-O
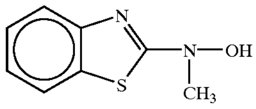

-continued
Cpd-P
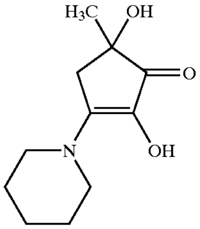
Cpd-Q
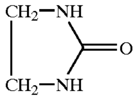
U-1
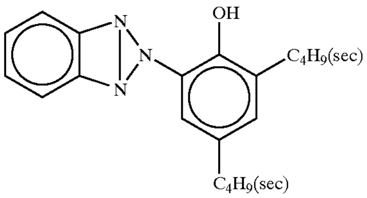
U-2
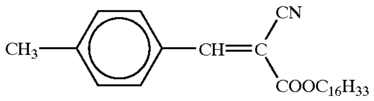
U-3
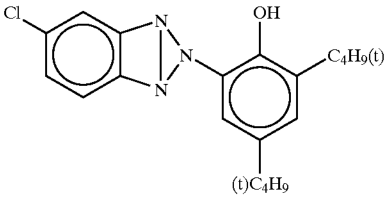
U-4
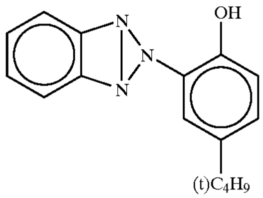
U-5
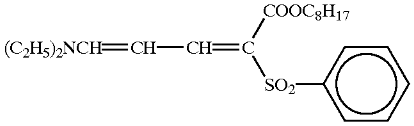
U-6
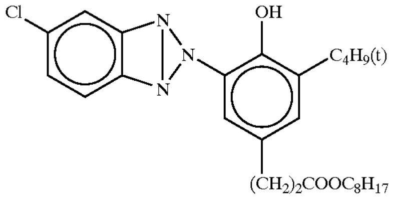
S-1
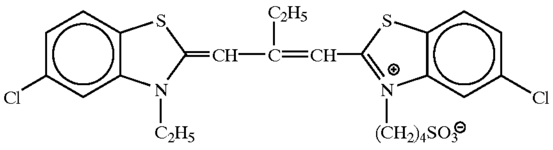
S-2
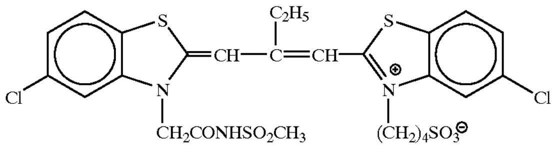
S-3
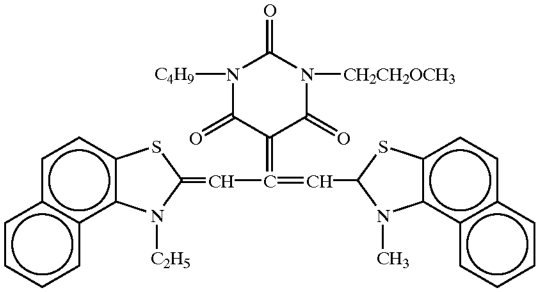
S-4
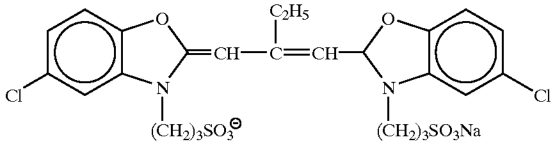
S-5
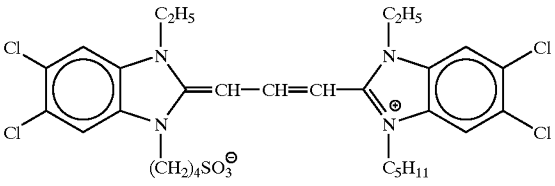
S-6
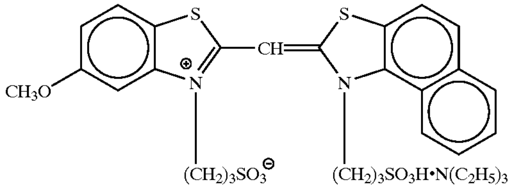

-continued
S-7
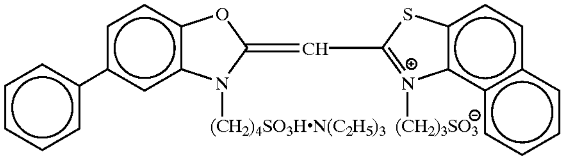
S-8
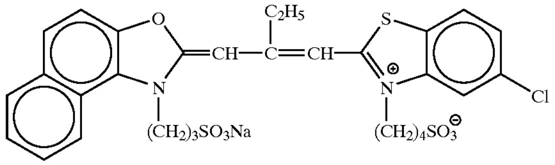
S-9
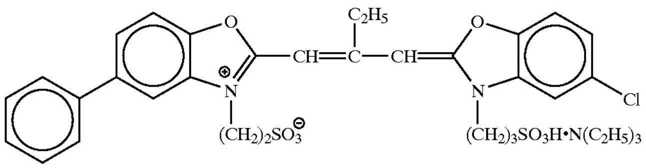
S-10
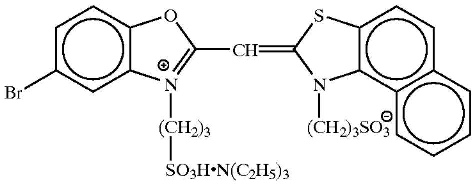
S-11
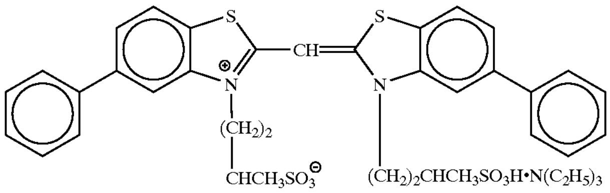
S-12
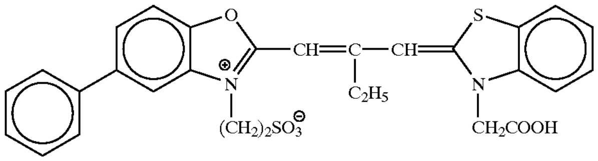
S-13
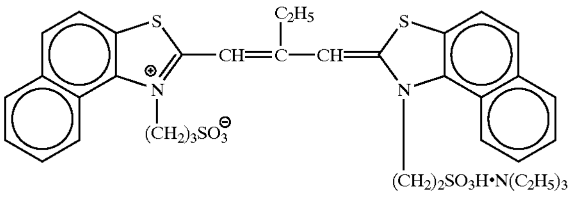
D-1
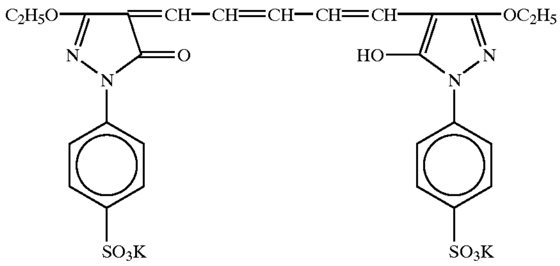
D-2
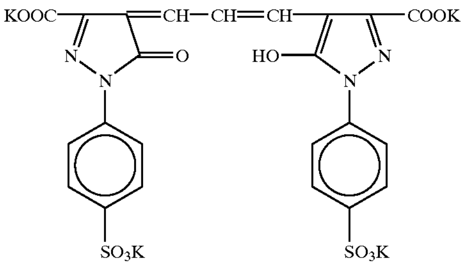
D-3
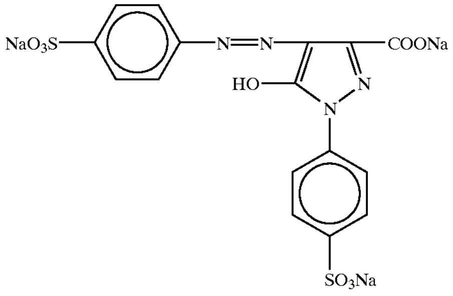

-continued
D-4
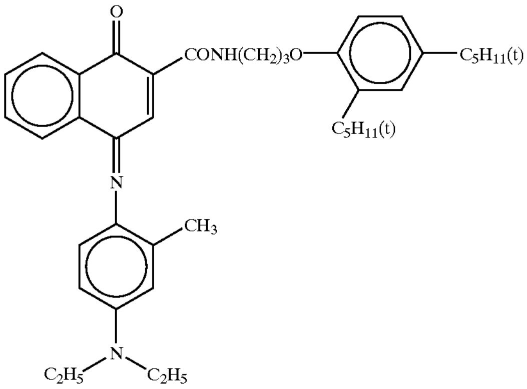
D-5
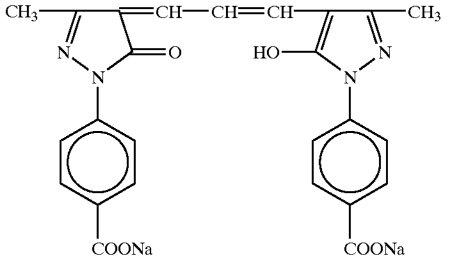
D-6
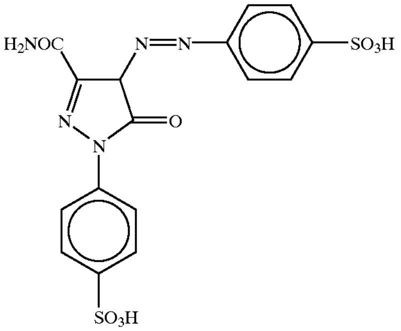
D-7
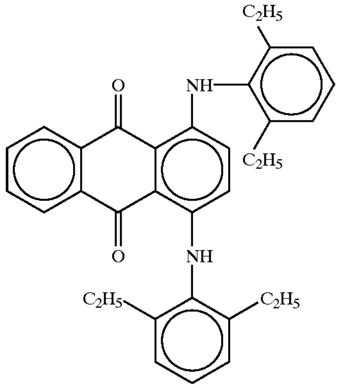
D-8
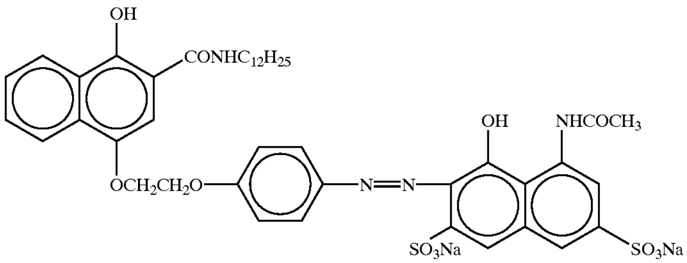
D-9
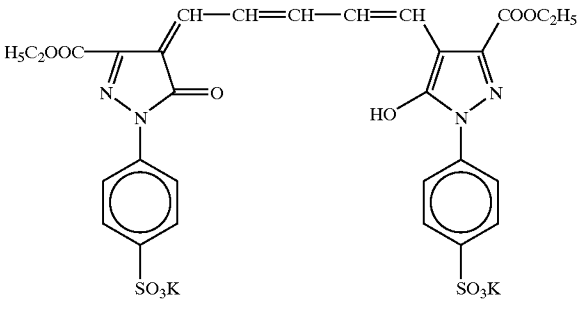
E-1
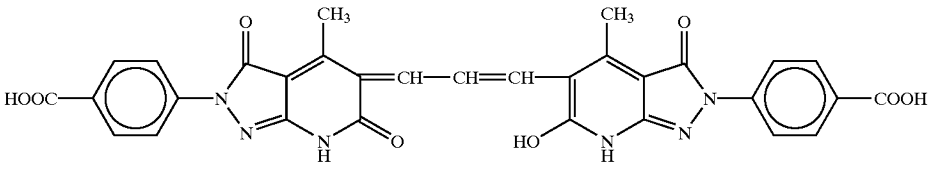

-continued
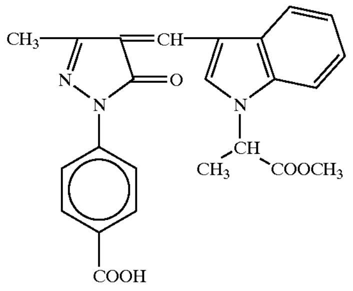
E-2
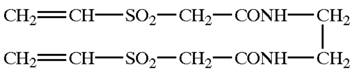
H-1
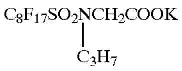
W-2
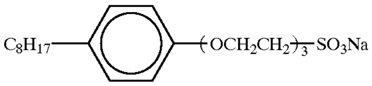
W-4
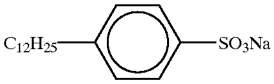
W-6
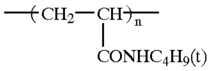
($n$ = 100–1000)
P-1
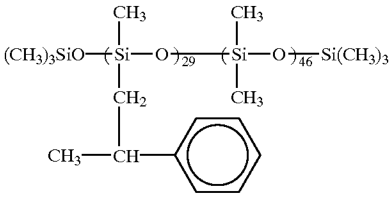
SO-1
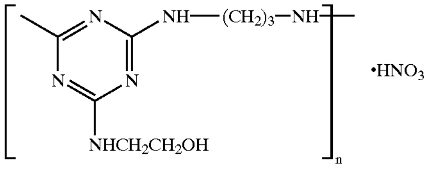
($n$ = 3–4)
F-2
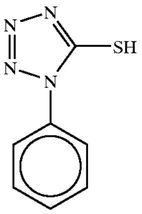
F-4
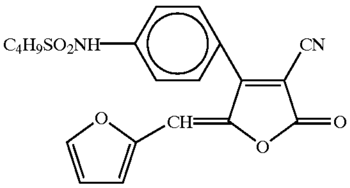
E-3
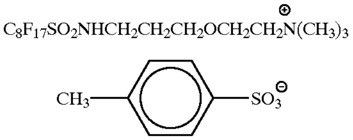
W-1
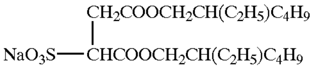
W-3
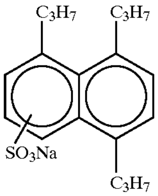
W-5
$C_8F_{17}SO_3Li$
W-7
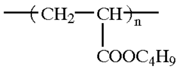
($n$ = 100–1000)
P-2
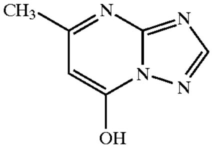
F-1
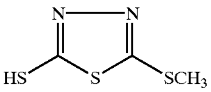
F-3
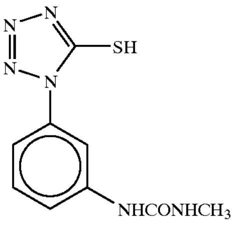
F-5

-continued
F-6
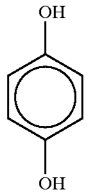
F-7
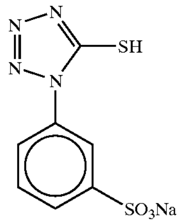
F-8
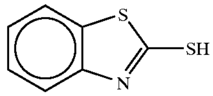
F-9
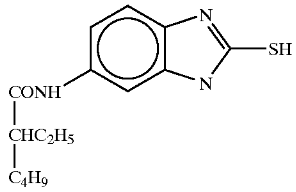
F-10
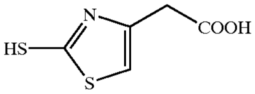
Comparative coupler A
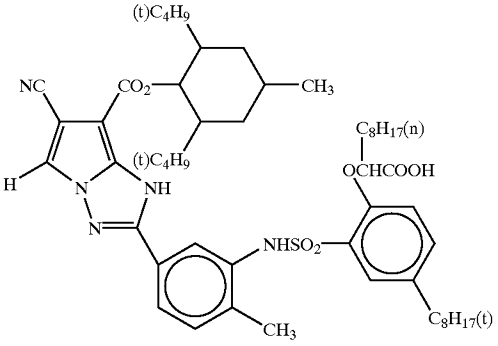
((46) described in JP-A-10-198009)
Comparative coupler B
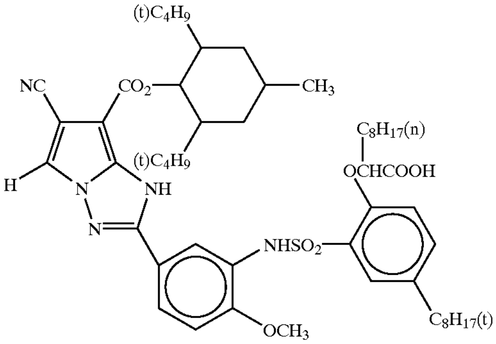
((41) described in JP-A-10-198009)
Comparative coupler C
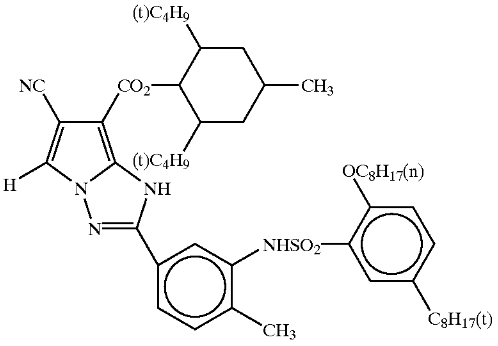
Competing coupler A
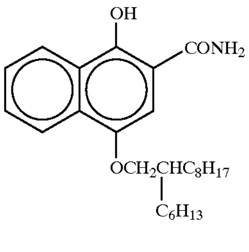
Oil-10
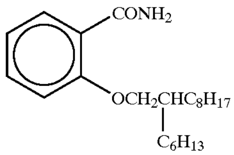

-continued

Oil-11

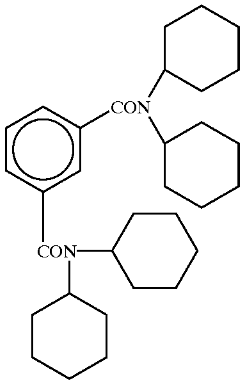

Preparation of Dispersion of Organic Solid Disperse Dye

The dye E-1 was dispersed by the following method. That is, water and 200 g of Pluronic F88 (ethylene oxide-propylene oxide block copolymer) manufactured by BASF CORP. were added to 1,430 g of a dye wet cake containing 30% of methanol, and the resultant material was stirred to form a slurry having a dye concentration of 6%. Subsequently, Ultra Visco Mill (UVM-2) manufactured by Imex K. K. was filled with 1,700 mL of zirconia beads with an average grain size of 0.5 mm, and the slurry was milled through UVM-2 at a peripheral speed of approximately 11 m/sec and a discharge rate of 0.5 L/min for 8 hr. The beads were filtered away, and water was added to dilute the material to a dye concentration of 3%. After that, the material was heated to 90° C. for 12 hr for a stabilization purpose. The average grain size of the obtained fine dye grains was 0.58 μm. The grain size distribution (grain size standard deviation×100/average grain size) was 18%.

Following the same procedure as above, solid dispersions of the dyes E-2 and E-3 were obtained. The average grain sizes were found to be 0.50 and 0.54 μm, respectively.

Samples 102 to 117 were formed by replacing the couplers in the 4th, 5th, and 6th layers of sample 101 as shown in Table 4. That is, C-1, C-2, and C-3 were replaced by 0.5-fold molar quantities of couplers of the present invention or comparative couplers, and the high-boiling organic solvent Oil-2 was added in amounts (weight ratios to couplers) given in parentheses (the addition amounts from the state in which the high-boiling organic solvent Oil-2 added to sample 101 was removed). (0) indicates that the high-boiling organic solvent Oil-2 was not used at all. When other types of high-boiling organic solvents were used, they are also described in Table 4.

TABLE 4

Arrangements of samples

| Sample | | Coupler 4th layer | Coupler 5th layer | Coupler 6th layer |
|---|---|---|---|---|
| 101 | Comparative example | As described in text | As described in text | As described in text |
| 102 | Comparative example | Comparative coupler A (0.2) | Comparative coupler A (0.2) | Comparative coupler A (0.2) |
| 103 | Comparative example | Comparative coupler B (0.2) | Comparative coupler B (0.2) | Comparative coupler B (0.2) |
| 104 | Comparative example | Comparative coupler C (1.0) | Comparative coupler C (1.0) | Comparative coupler C (1.0) |
| 105 | Present invention | Ex-(30) (0.2) | Ex-(30) (0.2) | Ex-(30) (0.2) |
| 106 | Present invention | Ex-(36) (0.2) | Ex-(36) (0.2) | Ex-(36) (0.2) |
| 107 | Present invention | Ex-(34) (0.2) | Ex-(34) (0.2) | Ex-(34) (0.2) |
| 108 | Present invention | Ex-(30) (0) | Ex-(30) (0) | Ex-(30) (0) |
| 109 | Present invention | Ex-(30) (Oil-10; 0.2) | Ex-(30) (Oil-10; 0.2) | Ex-(30) (Oil-10; 0.2) |
| 110 | Present invention | Ex-(22) (1.0) | Ex-(22) (1.0) | Ex-(22) (1.0) |
| 111 | Present invention | Ex-(22) (0.3) | Ex-(30) (0.2) | Ex-(30) (0.2) |
| 112 | Present invention | Ex-(51) (0.2) | Ex-(51) (0.2) | Ex-(51) (0.2) |
| 113 | Present invention | Ex-(49) (Oil-11; 0.3) | Ex-(49) (Oil-11; 0.3) | Ex-(49) (Oil-11; 0.3) |
| 114 | Present invention | Ex-(36) (Oil-9; 0.1) | Ex-(36) (Oil-9; 0.1) | Ex-(36) (Oil-9; 0.1) |
| 115 | Present invention | Ex-(20) (Oil-3; 0.5) | Ex-(20) (Oil-3; 0.5) | Ex-(20) (Oil-3; 0.5) |
| 116 | Present invention | Ex-(36) (Oil-11; 0.2) Cpd-M was added in amount of 30 mol % to Ex-(36) | Ex-(36) (Oil-11; 0.2) | Ex-(36) (Oil-11; 0.2) |
| 117 | Present invention | Ex-(36) (Oil-11; 0.2) Competing coupler A was added in amount of 50 mol % to Ex-(36) | Ex-(36) (Oil-11; 0.2) Competing coupler A was added in amount of 50 mol % to Ex-(36) | Ex-(36) (Oil-11; 0.2) |

In the table, Ex-( ) means an example compound ( ).

Development A below was performed in this example. In this processing, 50% of each of FUJICHROME RVP, FUJICHROME RDPII, ECTACHROME EPR, and ECTACHROME E100S were completely exposed to white light, and the resultant materials were used after being processed at a ratio of 1:2:1:2 until the replenishment amount was five times the tank volume.

| Processing step | Time | Temperature | Tank volume | Replenishment rate |
|---|---|---|---|---|
| 1st development | 6 min | 38° C. | 12 L | 2,200 mL/m$^2$ |
| 1st washing | 2 min | 38° C. | 4 L | 7,500 mL/m$^2$ |
| Reversal | 2 min | 38° C. | 4 L | 1,100 mL/m$^2$ |
| Color development | 6 min | 38° C. | 12 L | 2,200 mL/m$^2$ |
| Pre-bleaching | 2 min | 38° C. | 4 L | 1,100 mL/m$^2$ |
| Bleaching | 6 min | 38° C. | 12 L | 220 mL/m$^2$ |
| Fixing | 4 min | 38° C. | 8 L | 1,100 mL/m$^2$ |
| 2nd washing | 4 min | 38° C. | 8 L | 7,500 mL/m$^2$ |
| Final rinsing | 1 min | 25° C. | 2 L | 1,100 mL/m$^2$ |

The compositions of the processing solutions were as follows.

| <1st developer> | <Tank solution> | <Replenisher> |
|---|---|---|
| Nitrilo-N,N,N-trimethylene phosphonic acid pentasodium salt | 1.5 g | 1.5 g |
| Diethylenetriamine pentaacetic acid. pentasodium salt | 2.0 g | 2.0 g |
| Sodium sulfite | 30 g | 30 g |
| Hydroquinone.potassium monosulfonate | 20 g | 20 g |
| Potassium carbonate | 15 g | 20 g |
| Sodium bicarbonate | 12 g | 15 g |
| 1-phenyl-4-methyl-4-hydroxymethyl-3-pyrazolidone | 1.5 g | 2.0 g |
| Potassium bromide | 2.5 g | 1.4 g |
| Potassium thiocyanate | 1.2 g | 1.2 g |
| Potassium iodide | 2.0 mg | — |
| Diethyleneglycol | 13 g | 15 g |
| Water to make | 1,000 mL | 1,000 mL |
| pH | 9.60 | 9.60 |

The pH was adjusted by sulfuric acid or potassium hydroxide.

| <Reversal solution> | <Tank solution> | <Replenisher> |
|---|---|---|
| Nitrilo-N,N,N-trimethylene phosphonic acid. pentasodium salt | 3.0 g | the same as tank solution |
| Stannous chloride.dihydrate | 1.0 g | do |
| p-aminophenol | 0.1 g | do |
| Sodium hydroxide | 8 g | do |
| Glacial acetic acid | 15 mL | do |
| Water to make | 1,000 mL | do |
| pH | 6.00 | do |

The pH was adjusted by acetic acid or sodium hydroxide.

| <Color developer> | <Tank solution> | <Replenisher> |
|---|---|---|
| Nitrilo-N,N,N-trimethylene phosphonic acid. pentasodium salt | 2.0 g | 2.0 g |
| Sodium sulfite | 7.0 g | 7.0 g |
| Trisodium phosphate. dodecahydrate | 36 g | 36 g |
| Potassium bromide | 1.0 g | — |
| Potassium iodide | 90 mg | — |
| Sodium hydroxide | 3.0 g | 3.0 g |
| Citrazinic acid | 1.5 g | 1.5 g |
| N-ethyl-N-(β-methanesulfon amidoethyl)-3-methyl-4 aminoaniline.3/2 sulfuric acid.monohydrate | 11 g | 11 g |
| 3,6-dithiaoctane-1,8-diol | 1.0 g | 1.0 g |
| Water to make | 1,000 mL | 1,000 mL |
| pH | 11.80 | 12.00 |

The pH was adjusted by sulfuric acid or potassium hydroxide.

| <Pre-bleaching solution> | <Tank solution> | <Replenisher> |
|---|---|---|
| Ethylenediaminetetraacetic acid.disodium salt. dihydrate | 8.0 g | 8.0 g |
| Sodium sulfite | 6.0 g | 8.0 g |
| 1-thioglycerol | 0.4 g | 0.4 g |
| Formaldehyde sodium bisulfite adduct | 30 g | 35 g |
| Water to make | 1,000 mL | 1,000 mL |
| pH | 6.30 | 6.10 |

The pH was adjusted by acetic acid or sodium hydroxide.

| <Bleaching solution> | <Tank solution> | <Replenisher> |
|---|---|---|
| Ethylenediaminetetraacetic acid.disodium salt. dihydrate | 2.0 g | 4.0 g |
| Ethylenediaminetetraacetic acid.Fe(III).ammonium. dihydrate | 120 g | 240 g |
| Potassium bromide | 100 g | 200 g |
| Ammonium nitrate | 10 g | 20 g |
| Water to make | 1,000 mL | 1,000 mL |
| pH | 5.70 | 5.50 |

The pH was adjusted by nitric acid or sodium hydroxide.

| <Fixing solution> | <Tank solution> | <Replenisher> |
|---|---|---|
| Ammonium thiosulfate | 80 g | the same as tank solution |
| Sodium sulfite | 5.0 g | the same as tank solution |
| Sodium bisulfite | 5.0 g | the same as tank solution |
| Water to make | 1,000 mL | the same as tank solution |
| pH | 6.60 | |

The pH was adjusted by acetic acid or ammonia water.

| <Stabilizer> | <Tank solution> | <Replenisher> |
|---|---|---|
| 1,2-benzoisothiazoline-3-one | 0.02 g | 0.03 g |
| Polyoxyethylene-p-monononyl phenylether (average polymerization degree = 10) | 0.3 g | 0.3 g |
| Polymaleic acid (average molecular weight = 2,000) | 0.1 g | 0.15 g |
| Water to make | 1,000 mL | 1,000 mL |
| pH | 7.0 | 7.0 |

(Evaluation of Samples)

(Evaluation of Color Reproduction)

Each of samples 101 to 117 was cut into a 135 size, processed into the form of a magazine, and loaded into a camera. Each resultant film was used to photograph a neutral gray chart having a reflection density of 1.0 and subjected to the abovementioned development. Filter conditions by which the gray balance after the processing was met were obtained for each sample, and green and cyan objects were photographed through the filter. Ten research workers participating in image evaluation at Fuji Photo Film Co., Ltd. Ashigara Laboratory made organoleptic evaluation on the photographed and developed results. That is, each research worker marked the degrees of reproduction of the saturation of each original on the basis of 10 points, and the points were totaled.

(Evaluation of Image Storage Stability)

Samples 101 to 117 were subjected to development B which was the same as the development A described above except that each sample was exposed to white light having a color temperature of 4,800 K through a wedge having a continuously changing density, that the time of the second washing was 1 min, and that the replenishment rate was reduced to 1,000 mL per $m^2$ of the sensitive material. After the densities of these processed samples were measured, they were stored at 60° C. and 70% RH for 40 days, and their densities were again measured. As evaluation of the image storage stability, Table 5 shows development of the cyan density in a Dmax portion.

TABLE 5

| Sample | | Evaluation results | | |
|---|---|---|---|---|
| | | Color reproduction | Image stability (Cyan density change (from initial density 2.0) at 60° C. 70% RH for 60 days) | Magenta stain (Increase of magenta density at minimum density portion at 60° C. 70% RH for 60 days) |
| 101 | Comparative example | 60 | 0.30 | 0.01 |
| 102 | Comparative example | 85 | 0.45 | 0.10 |
| 103 | Comparative example | 88 | 0.40 | 0.08 |
| 104 | Comparative example | 85 | 0.40 | 0.07 |
| 105 | Present invention | 92 | 0.10 | 0.02 |
| 106 | Present invention | 92 | 0.12 | 0.01 |
| 107 | Present invention | 92 | 0.10 | 0.02 |
| 108 | Present invention | 90 | 0.10 | 0.02 |
| 109 | Present invention | 96 | 0.10 | 0.02 |
| 110 | Present invention | 92 | 0.08 | 0.03 |
| 111 | Present invention | 92 | 0.08 | 0.02 |
| 112 | Present invention | 90 | 0.06 | 0.01 |
| 113 | Present invention | 95 | 0.06 | 0.02 |
| 114 | Present invention | 90 | 0.08 | 0.01 |
| 115 | Present invention | 94 | 0.10 | 0.02 |
| 116 | Present invention | 95 | 0.10 | 0.01 |
| 117 | Present invention | 95 | 0.08 | 0.02 |

As shown in Table 5, couplers of the present invention were preferable because they were superior in color reproduction and could form stable images. Also, when a blix fading test was conducted, any coupler of the present invention kept being excellent without causing any blix fading.

EXAMPLE 2

Corona discharge was performed on the surface of a support formed by coating the two surfaces of a paper sheet with a polyethylene resin. After that, a gelatin undercoat layer containing sodium dodecylbenzenesulfonate was formed. In addition, first to seventh photographic constituent layers were formed by coating to make sample (201) of a silver halide color photographic lightsensitive material having the following layer arrangement. H-A, H-B, and H-C were used as gelatin hardeners of each layer.

Also, Ab-1, Ab-2, Ab-3, and Ab-4 were added to each layer such that the total amounts were 15.0, 60.0, 5.0, and 10.0 $mg/m^2$, respectively.

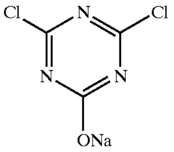

(H-A) Hardner (Used in an amount of 0.50 wt % of gelatin)

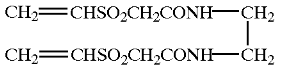

(H-B) Hardner (Used in an amount of 1.20 wt % of gelatin)

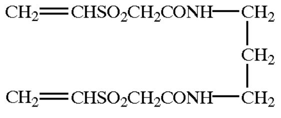

(H-C) Hardner (Used in an amount of 0.40 wt % of gelatin)

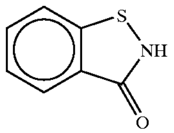

(Ab-1) Antiseptic

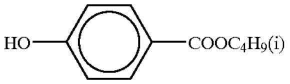

(Ab-2) Antiseptic

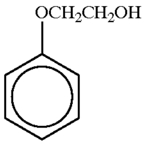

(Ab-3) Antiseptic

-continued

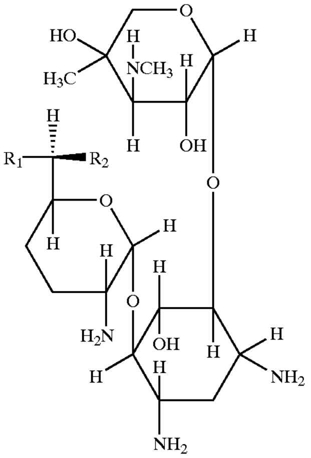

| | $R_1$ | $R_2$ |
|---|---|---|
| a | $-CH_3$ | $-NHCH_3$ |
| b | $-CH_3$ | $-NH_2$ |
| c | $-H$ | $-NH_2$ |
| d | $-H$ | $-NHCH_3$ |

(Ab-4) Antiseptic

A mixture of a:b:c:d in a molar ratio of 1:1:1:1

Spectral sensitizing dyes and a crystal phase control agent 1 below were used in silver chlorobromide emulsions of the individual photosensitive emulsion layers.

Blue-sensitive emulsion layer

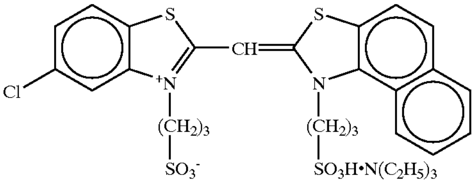

Sensitizing dye A

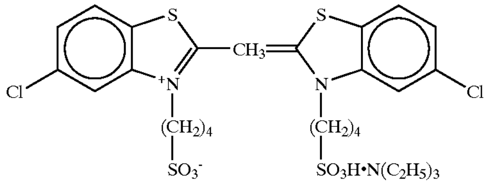

Sensitizing dye B

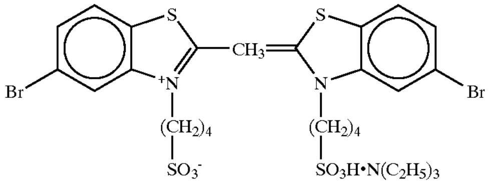

Sensitizing dye C

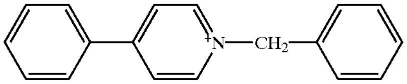

Crystal habit controller 1

(Each of the sensitizing dyes A and C was added in amounts of $0.42\times10^{-4}$ and $0.50\times10^{-4}$ mol for large- and small-size emulsions, respectively, per mol of a silver halide. The sensitizing dye B was added in amounts of $3.4\times10^{-4}$ and $4.1\times10^{-4}$ mol for large- and small-size emulsions, respectively, per mol of a silver halide.)

Green-sensitive emulsion layer

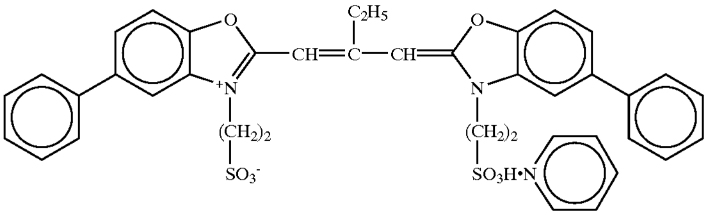

Sensitizing dye D

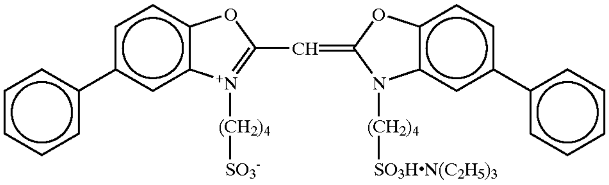

Sensitizing dye E

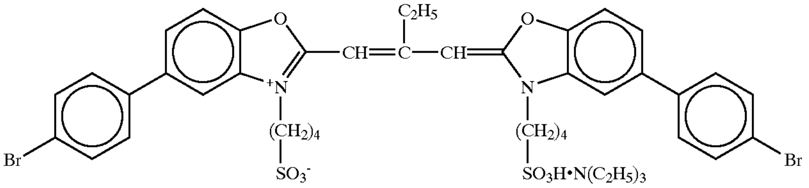

Sensitizing dye F (The sensitizing dye D was added in amounts of $3.0\times10^{-4}$ and $3.6\times10^{-4}$ mol for large- and small-size emulsions, respectively, per mol of a silver halide. The sensitizing dye E was added in amounts of $4.0\times10^{-5}$ and $7.0\times10^{-5}$ mol for large- and small-size emulsions, respectively, per mol of a silver halide. The sensitizing dye F was added in amounts of $2.0\times10^{-4}$ and $2.8\times10^{-4}$ mol for large- and small-size emulsions, respectively, per mol of a silver halide.)

Red-sensitive emulsion layer

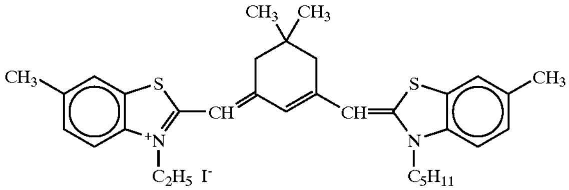

Sensitizing dye G

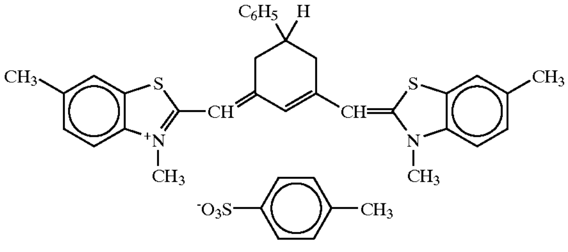

Sensitizing dye H (Each of the sensitizing dyes G and H was added in amounts of $8.0\times10^{-5}$ and $10.7\times10^{-5}$ mol for large- and small-size emulsions, respectively, per mol of a silver halide.)

In addition, $3.0\times10^{-3}$ mol of a compound I presented below was added to the red-sensitive emulsion layer per mol of a silver halide.

Compound I

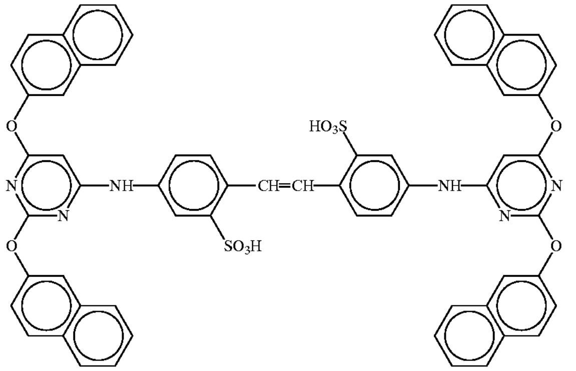

$3.3\times10^{-4}$, $1.0\times10^{-3}$, and $5.9\times10^{-4}$ mol of 1-(3-methylureidophenyl)-5-mercaptotetrazole were added to the blue-, green-, and red-sensitive emulsion layers, respectively, per mol of a silver halide.

Furthermore, 0.2, 0.2, 0.6, and 0.1 mg/m$^2$ of the same compound were added to the second, fourth, sixth, and seventh layers, respectively.

$1\times10^{-4}$ and $2\times10^{-4}$ mol of 4-hydroxy-6-methyl-1,3,3a,7-tetrazaindene were added to the blue- and green-sensitive layers, respectively, per mol of a silver halide.

0.05 g/m$^2$ of a copolymer latex of methacrylic acid and butyl acrylate (weight ratio 1:1, average molecular weight 200,000 to 400,000) were added to the red-sensitive emulsion layer.

6, 6, and 18 mg/m$^2$ of disodium catechol-3,5-disulfonate were added to the second, fourth, sixth layers, respectively.

To prevent irradiation, the following dyes (coating amounts are given in parentheses) were added.

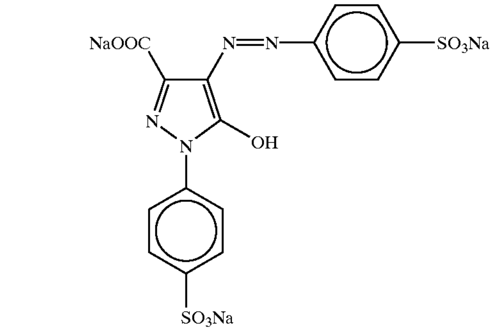

(2mg/m$^2$)

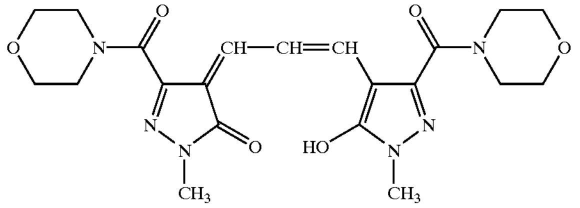

(4mg/m$^2$)

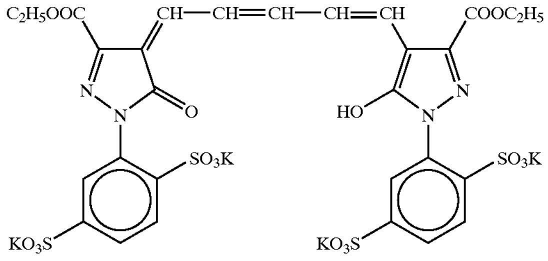

(9mg/m$^2$)

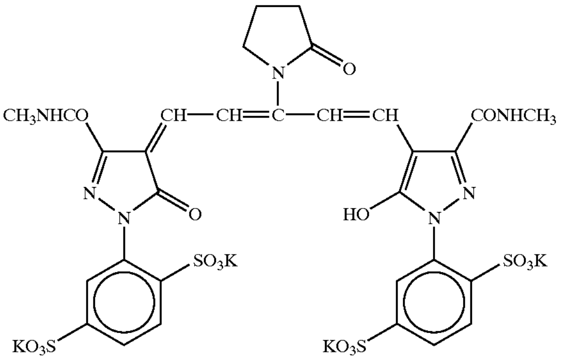

(9mg/m$^2$)

(Layer Arrangement)

The arrangement of the layers was as follows. The numbers indicate the coating amounts (g/m$^2$). The amount of a silver halide emulsion is represented by a silver coating amount.

Support

Polyethylene Resin Laminated Paper

[Polyethylene resin on the first layer side contained a white pigment ($TiO_2$; content 16 wt %, ZnO; content 4 wt %), a fluorescent whitening agent (4,4'-bis(5-methylbenzoxazolyl)stilbene; content 0.03 wt %), and a blue dye (ultramarine blue)].

First Layer (Blue-sensitive Emulsion Layer)

Silver chlorobromide emulsion A (cubic, a 5:5 mixture (silver molar ratio) of a large-size emulsion A having an average grain size of 0.72 μm and a small-size emulsion A having an average grain size of 0.60 μm. The variation coefficients of grain size distributions of the large- and small-size emulsions were 0.08 and 0.10, respectively. In each emulsion, a portion of the surface of a grain having silver chloride as a substrate locally contained 0.3 mol % of silver bromide)

| | |
|---|---|
| | 0.24 |
| Gelatin | 1.25 |
| Yellow coupler (ExY) | 0.57 |
| Color image stabilizer (Cpd-1) | 0.07 |
| Color image stabilizer (Cpd-2) | 0.04 |
| Color image stabilizer (Cpd-3) | 0.07 |
| Color image stabilizer (Cpd-8) | 0.02 |
| Solvent (Solv-1) | 0.21 |
| Second layer (Color-mixing inhibiting layer) | |
| Gelatin | 0.99 |
| Color-mixing inhibitor (Cpd-4) | 0.09 |
| Color-mixing inhibitor (Cpd-19) | 0.03 |
| Color-mixing preventing aid (Cpd-5) | 0.018 |
| Stabilizer (Cpd-6) | 0.13 |
| Color-mixing inhibitor (Cpd-7) | 0.01 |
| Solvent (Solv-1) | 0.06 |
| Solvent (Solv-2) | 0.22 |
| Solvent (Solv-6) | 0.05 |

Third Layer (Green-sensitive Emulsion Layer)

Silver chlorobromide emulsion B (cubic, a 1:3 mixture (silver molar ratio) of a large-size emulsion B having an average grain size of 0.45 μm and a small-size emulsion B having an average grain size of 0.35 μm. The variation coefficients of grain size distributions of the large- and small-size emulsions were 0.10 and 0.08, respectively. In each emulsion, a portion of the surface of a grain having silver chloride as a substrate locally contained 0.4 mol % of silver bromide)

| | |
|---|---|
| | 0.14 |
| Gelatin | 1.36 |
| Magenta coupler (ExM) | 0.15 |
| Ultraviolet absorber (UV-A) | 0.14 |
| Color image stabilizer (Cpd-2) | 0.02 |
| Color-mixing inhibitor (Cpd-4) | 0.002 |
| Stabilizer (Cpd-6) | 0.09 |
| Color image stabilizer (Cpd-8) | 0.02 |
| Color image stabilizer (Cpd-9) | 0.03 |
| Color image stabilizer (Cpd-10) | 0.01 |
| Colorating agent (Cpd-11) | 0.0001 |
| Solvent (Solv-3) | 0.11 |
| Solvent (Solv-4) | 0.22 |
| Solvent (Solv-5) | 0.20 |
| Fourth layer (Color-mixing inhibiting layer) | |
| Gelatin | 0.71 |
| Color-mixing inhibitor (Cpd-4) | 0.06 |
| Color-mixing preventing aid (Cpd-5) | 0.013 |
| Stabilizer (Cpd-6) | 0.10 |
| Color-mixing inhibitor (Cpd-7) | 0.007 |
| Solvent (Solv-1) | 0.04 |
| Solvent (Solv-2) | 0.16 |

Fifth Layer (Red-sensitive Emulsion Layer)

Silver chlorobromide emulsion C (cubic, a 5:5 mixture (silver molar ratio) of a large-size emulsion C having an average grain size of 0.40 μm and a small-size emulsion C having an average grain size of 0.30 μm. The variation coefficients of grain size distributions of the large- and small-size emulsions were 0.09 and 0.11, respectively. In each emulsion, a portion of the surface of a grain having silver chloride as a substrate locally contained 0.5 mol % of silver bromide)

| | |
|---|---|
| | 0.12 |
| Gelatin | 1.11 |
| Cyan coupler (ExC-2) | 0.13 |
| Cyan coupler (ExC-3) | 0.03 |
| Color image stabilizer (Cpd-1) | 0.05 |
| Stabilizer (Cpd-6) | 0.06 |
| Color-mixing inhibitor (Cpd-7) | 0.02 |
| Color image stabilizer (Cpd-9) | 0.04 |
| Color image stabilizer (Cpd-10) | 0.01 |
| Color image stabilizer (Cpd-12) | 0.01 |
| Hue-regulating agent (Cpd-14) | 0.01 |
| Hue-regulating agent (Cpd-15) | 0.12 |
| Color-regulating agent (Cpd-16) | 0.03 |
| Color-regulating agent (Cpd-17) | 0.09 |
| Color image stabilizer (Cpd-18) | 0.07 |
| Solvent (Solv-5) | 0.15 |
| Solvent (Solv-8) | 0.05 |
| Surfactant (Cpd-20) | 0.01 |
| Sixth layer (Ultraviolet absorbing layer) | |
| Gelatin | 0.46 |
| Ultraviolet absorber (UV-B) | 0.45 |
| Solvent (Solv-7) | 0.25 |
| Seventh layer (Protective layer) | |
| Gelatin | 1.00 |
| Acryl modified copolymer of polyvinyl alcohol (modification degree 17%) | 0.04 |
| Liquid paraffin | 0.02 |
| Surfactant (Cpd-13) | 0.01 |

(ExY) Yellow couplers : A mixture of

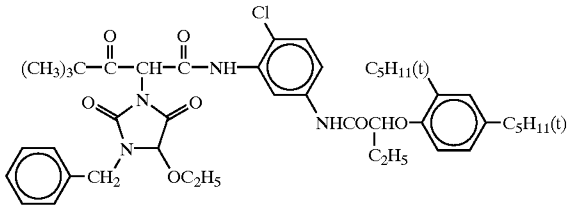

and

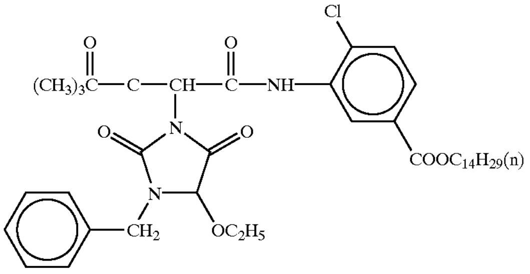

in a molar ratio of 70:30

-continued (ExM) Magenta couplers : A mixture of

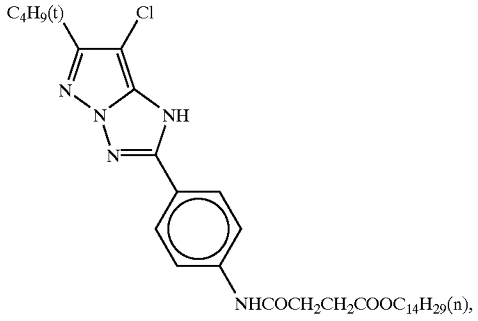

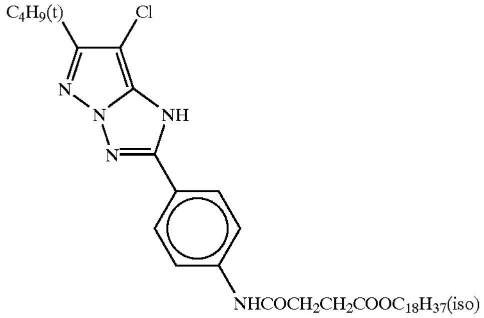

and

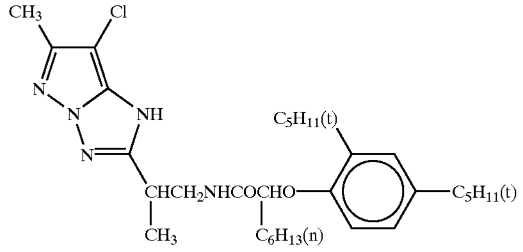

in a molar ratio of 40:40:20

(ExC-2) Cyan coupler

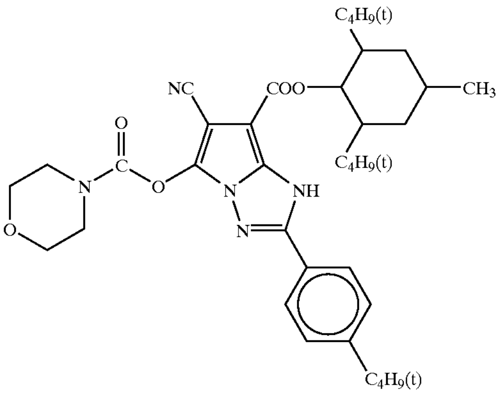

(ExC-3) Cyan couplers : A mixture of

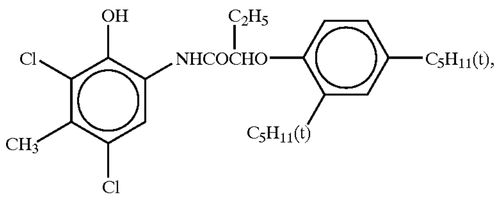

-continued

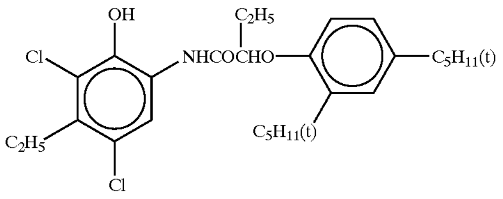

and

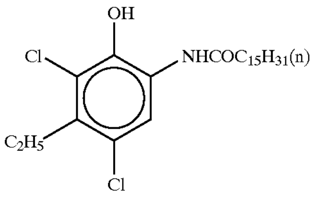

in a molar ratio of 50:25:50

(Cpd-1) Color image stabilizer

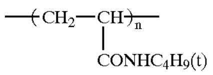

Number average molecular weight 60,000

(Cpd-2) Color image stabilizer

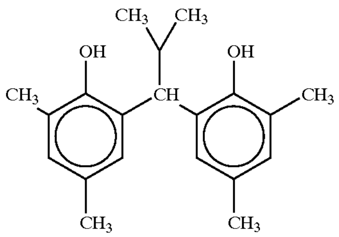

(Cpd-3) Color image stabilizer

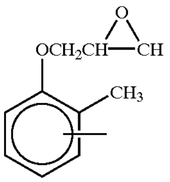

(Cpd-5) Color-mixing preventing aid

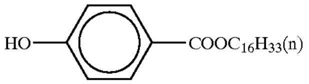

(Cpd-6) Stabilizer

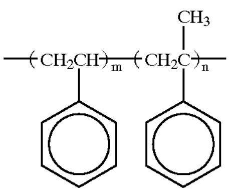

Number average molecular weight 600
m/n = 10/90

-continued (Cpd-7) Color-mixing inhibitor

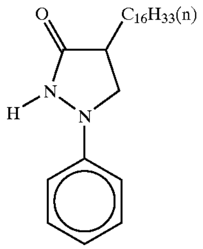

(Cpd-8) Color image stabilizer

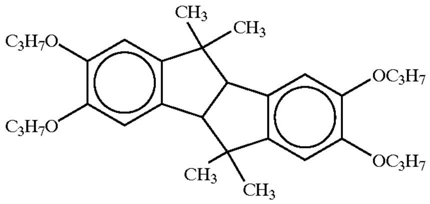

(CPd-9) Color image stabilizer

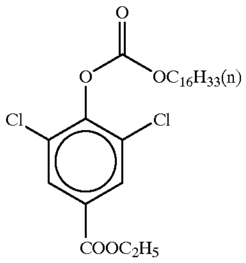

(Cpd-10) Color image stabilizer

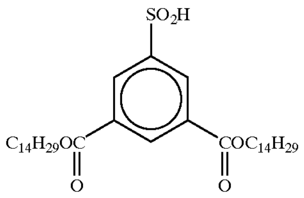

(Cpd-11)

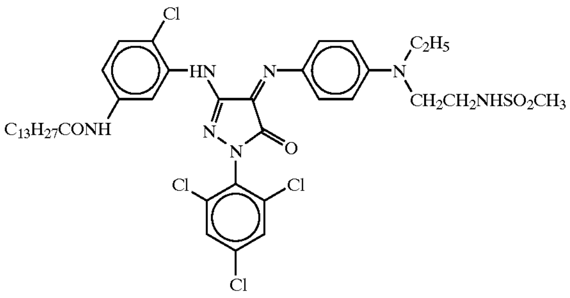

(Cpd-12) Color image stabilizer

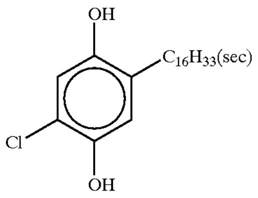

-continued
(Cpd-13) Surfactants : A7 : 3 mixture of
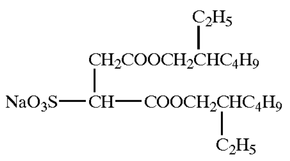
and
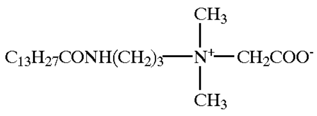
(Cpd-14)
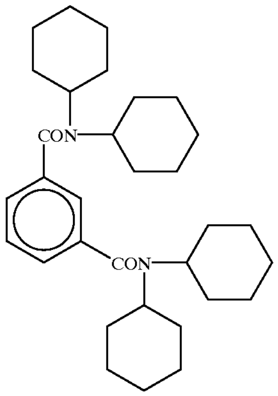
(Cpd-15)
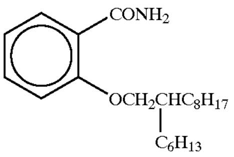
(Cpd-16)
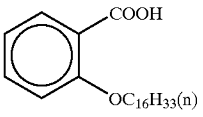
(Cpd-17)
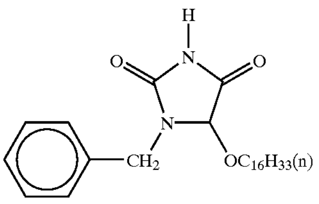
(Cpd-18)
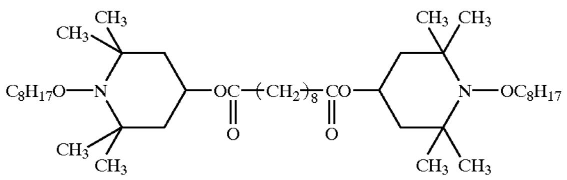
-continued
(Cpd-19) Color-mixing inhibitor
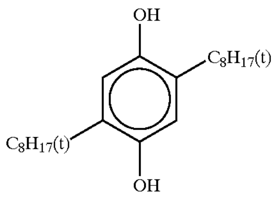
(Cpd-20) Surfactants : A mixture of
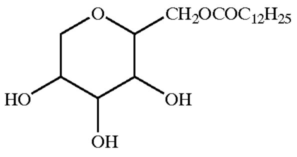
and
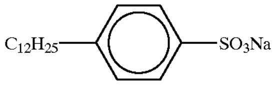
in a molar ratio 1:4
(UV-1) UV absorber
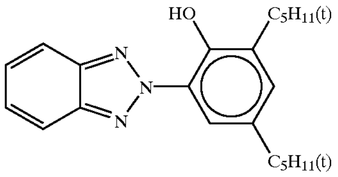
(UV-2) UV absorber
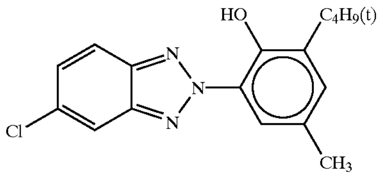
(UV-3) UV absorber
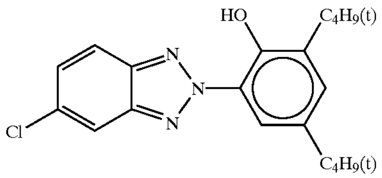
(UV-4) UV absorber
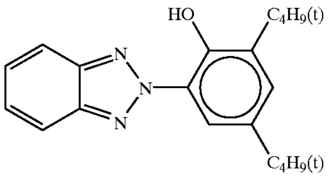
(UV-5) UV absorber
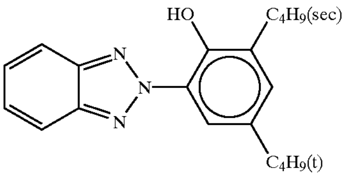

-continued (UV-6) UV absorber

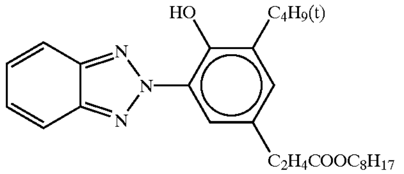

UV-A : A mixture in a weight ratio of UV-1/UV-2/UV-3/UV-4=4/2/2/3

UV- B : A mixture in a weight ratio of UV-1/UV-2/UV-3/UV-4/UV-5/UV-6=9/3/3/4/5/3

(Solv-1)

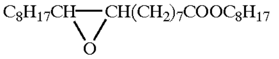

(Solv-2)

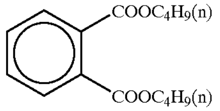

(Solv-3)

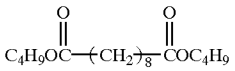

(Solv-4)

$O{=}P{-}(OC_6H_{13}(n))_3$ (Solv-5)

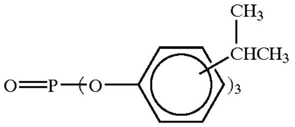

(Solv-6)A mixture of

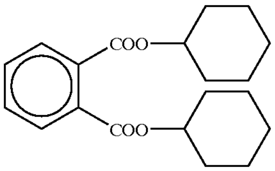

and

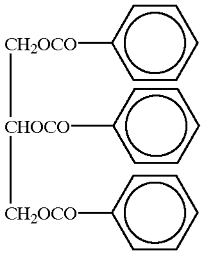

in a weight ratio of 1:1

(Solv-7)

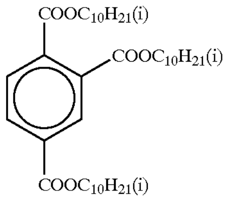

(Solv-8)

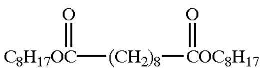

Samples 202 to 210 were formed following the same procedures as for sample 201 except that the coupler ExC-2 in the fifth layer of sample 201 was replaced with an equal molar quantity of couplers shown in Table 6.

TABLE 6

Arrangements of samples and evaluation results

| Sample | | Coupler (replaced by ExC-2) in 5th layer | Image stability Cyan density change in processing B/cyan density change in processing A |
|---|---|---|---|
| 201 | Comparative example | As described in text | 1.3 |
| 202 | Comparative example | Comparative coupler A | 2.5 |
| 203 | Comparative example | Comparative coupler B | 2.2 |
| 204 | Present invention | Ex-(30) | 1.2 |
| 205 | Present invention | Ex-(51) | 1.0 |
| 206 | Present invention | Ex-(49) | 1.0 |
| 207 | Present invention | Ex-(52) | 1.0 |
| 208 | Present invention | Ex-(50) | 1.0 |
| 209 | Present invention | Ex-(54) | 1.0 |
| 210 | Present invention | Ex-(53) | 1.0 |

Samples 201 to 210 were imagewise exposed such that yellow, magenta, cyan, and gray images were formed, and subjected to processing A and processing B, and the density of each sample was measured. After that, each sample was stored for 40 days at 60° C. and 70% RH, and a density change (at the point at which a cyan density of 2.0 was given in the gray image immediately after the processing) was measured before and after the storage. This density change was measured for each of the processing A and processing B (to be described later), and a density change in the processing B/a density change in the processing A is rile shown in Table 6. If this value is 1, the image stability remained unchanged in the processing A and processing B. If this value is larger than 1, the image stability in the processing B suffered.

As can be seen from Table 6, couplers of the present invention did not worsen the image stability and gave favorable results even when the rapid processing (processing B) was performed.

Processing A

The sensitive materials 201 and 208 were formed into 127-mm wide rolls and subjected to continuous processing (running test) (201:208=1:1) by the following processing steps after imagewise exposure until a twofold amount of the color development tank volume was replenished by using a PP1258AR mini-lab printer processor manufactured by Fuji Photo Film Co., Ltd. Processing using this running solution was the processing A.

| Processing step | Temperature | Time | Replenishment rate* |
|---|---|---|---|
| Color development | 38.5° C. | 45 sec | 45 mL |
| Bleach-fixing | 38.0° C. | 45 sec | 35 mL |

-continued

| Processing step | Temperature | Time | Replenishment rate* |
|---|---|---|---|
| Rinsing (1) | 38.0° C. | 20 sec | — |
| Rinsing (2) | 38.0° C. | 20 sec | — |
| Rinsing (3) | **38.0° C. | 20 sec | — |
| Rinsing (4) | **38.0° C. | 30 sec | 121 mL |

*A replenishment amount per $m^2$ of the sensitive material

**An RC50D rinse cleaning system manufactured by Fuji Photo Film Co., Ltd. was set in rinsing (3), and the rinsing solution was extracted from rinsing (3) and supplied to a reverse osmosis membrane module (RC50D) by a pump. The tramsmitted water obtained by the tank was supplied to rinsing (4), and the concentrated water was returned to rinsing (3). The pump pressure was so adjusted that the amount of the transmitted water to the reverse osmosis module was maintained at 50 to 300 mL/min. In this manner, the rinsing solution was circulated for 10 hr/day at controlled termperature.

(Rinsing was done by a tank counterflow system from (1) to (4)).

The compositions of the individual processing solutions were as follows.

| | <Tank Solution> | <Replenisher> |
|---|---|---|
| <Color developer> | | |
| Water | 800 mL | 800 mL |
| Dimethylpolysiloxane-based surfactant (Silicone KF351A/manufactured by Shin-Etsu Chemical Co., Ltd.) | 0.1 g | 0.1 g |
| Tri(isopropanol)amine | 8.8 g | 8.8 g |
| Ethylenediaminetetraacetic acid | 4.0 g | 4.0 g |
| Polyethyleneglycol (molecular weight 300) | 10.0 g | 10.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene-based fluorescent whitening agent (Hakkol FWA-SF/ manufactured by Showa Chemical Industry Co., Ltd.) | 2.5 g | 5.0 g |
| Sodium sulfite | 0.1 g | 0.1 g |
| Disodium-N,N-bis(sulfonatoethyl) hydroxylamine | 8.5 g | 11.1 g |
| N-ethyl-N-(β-methanesulfonamido-ethyl)-3-methyl-4-amino-4-aminoaniline.3/2 sulfuric acid.monohydrate | 5.0 g | 15.7 g |
| Potassium carbonate | 26.3 g | 26.3 g |
| Water to make | 1,000 mL | 1,000 mL |
| pH (25° C./adjusted by potassium hydroxide and sulfuric acid) | 10.15 | 12.50 |
| <Bleach-fixing solution> | | |
| Water | 700 mL | 600 mL |
| Ammonium ethylenediaminetetra-acetate iron(III) | 47.0 g | 94.0 g |
| Ethylenediaminetetraacetic acid | 1.4 g | 2.8 g |
| m-carboxybenzenefulfinic acid | 8.3 g | 16.5 g |
| Nitric acid (67%) | 16.5 g | 33.0 g |
| Imidazole | 14.6 g | 29.2 g |
| Ammonium thiosulfate (750 g/L) | 107.0 mL | 214.0 mL |
| Ammonium sulfite | 16.0 g | 32.0 g |
| Ammonium bisulfite | 23.1 g | 46.2 g |
| Water to make | 1,000 mL | 1,000 mL |
| pH (25° C./adjusted by acetic acid and ammonia) | 6.0 | 6.0 |

-continued

| | <Tank Solution> | <Replenisher> |
|---|---|---|
| <Rinsing solution> | | |
| Chlorinated sodium isocyanurate | 0.02 g | 0.02 g |
| Deionized water (conductivity = 5 μs/cm or less) | 1,000 mL | 1,000 mL |
| pH | 6.5 | 6.5 |

The sensitive materials 201 and 208 were formed into 127-mm wide rolls and subjected to continuous processing (running test) (201:208=1:1) by the following processing steps after imagewise exposure until a twofold amount of the color development tank volume was replenished. Processing using this running solution was the processing B. The processing was done by using a PP1258AR mini-lab printer processor manufactured by Fuji Photo Film Co., Ltd., which was remodeled to raise the conveyance velocity in order to reduce the processing time.

| Processing step | Temperature | Time | Replenishment rate* |
|---|---|---|---|
| Color development | 45.0° C. | 12 sec | 45 mL |
| Bleach-fixing | 40.0° C. | 12 sec | 35 mL |
| Rinsing (1) | 40.0° C. | 4 sec | — |
| Rinsing (2) | 40.0° C. | 4 sec | — |
| Rinsing (3) | **40.0° C. | 4 sec | — |
| Rinsing (4) | **40.0° C. | 4 sec | 121 mL |

*A replenishment amount per $m^2$ of the sensitive material

**An RC50D rinse cleaning system manufactured by Fuji Photo Film Co., Ltd. was set in rinsing (3), and the rinsing solution was extracted from rinsing (3) and supplied to a reverse osmosis membrane module (RC50D) by a pump. The tramsmitted water obtained by the tank was supplied to rinsing (4), and the concentrated water was returned to rinsing (3). The pump pressure was so adjusted that the amount of the transmitted water to the reverse osmosis module was maintained at 50 to 300 mL/min. In this manner, the rinsing solution was circulated for 10 hr/day at controlled termperature.

(Rinsing was done by a tank counterflow system from (1) to (4)).

The compositions of the individual processing solutions were as follows.

| | <Tank Solution> | <Replenisher> |
|---|---|---|
| <Color developer> | | |
| Water | 800 mL | 800 mL |
| Dimethylpolysiloxane-based surfactant (Silicone KF351A/manufactured by Shin-Etsu Chemical Co., Ltd.) | 0.1 g | 0.1 g |
| Tri(isopropanol)amine | 8.8 g | 8.8 g |
| Ethylenediaminetetraacetic acid | 4.0 g | 4.0 g |
| Polyethyleneglycol (molecular weight 300) | 10.0 g | 10.0 g |
| Sodium 4,5-dihydroxybenzene 1,3-disulfonate | 0.5 g | 0.5 g |
| Potassium chloride | 10.0 g | — |
| Potassium bromide | 0.040 g | 0.010 g |
| Triazinylaminostilbene-based fluorescent whitening agent (Hakkol FWA-SF/manufactured by Showa Chemical Industry Co., Ltd.) | 2.5 g | 5.0 g |
| Sodium sulfite | 0.1 g | 0.1 g |
| Disodium-N,N-bis(sulfonatoethyl) hydroxylamine | 8.5 g | 11.1 g |

-continued

| | <Tank Solution> | <Replenisher> |
|---|---|---|
| N-ethyl-N-(-62 -methanesulfon-amido-ethyl)-3-methyl-4-amino-4-aminoaniline.3/2 sulfuric acid.monohydrate | 10.0 g | 22.0 g |
| Potassium carbonate | 26.3 g | 26.3 g |
| Water to make | 1,000 mL | 1,000 mL |
| pH (25° C./adjusted by potassium hydroxide and sulfuric acid) | 10.15 | 12.50 |
| <Bleach-fixing Solution> | | |
| Water | 700 mL | 600 mL |
| Ammonium ethylenediaminetetra-acetate iron(III) | 75.0 g | 150.0 g |
| Ethylenediaminetetraacetic acid | 1.4 g | 2.8 g |
| m-Carboxybenzenefulfinic acid | 8.3 g | 16.5 g |
| Nitric acid (67%) | 16.5 g | 33.0 g |
| Imidazole | 14.6 g | 29.2 g |
| Ammonium thiosulfate (750 g/L) | 107.0 mL | 214.0 mL |
| Ammonium sulfite | 16.0 g | 32.0 g |
| Ammonium bisulfite | 23.1 g | 46.2 g |
| Water to make | 1,000 mL | 1,000 mL |
| pH (25° C./adjusted by acetic acid and ammonia) | 5.5 | 5.5 |
| <Rinsing solution> | | |
| Chlorinated sodium isocyanurate | 0.02 g | 0.02 g |
| Deionized water (conductivity = 5 μs/cm or less) | 1,000 mL | 1,000 mL |
| pH | 6.5 | 6.5 |

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pyrrolotriazole compound represented by formula (I) below:

(I)

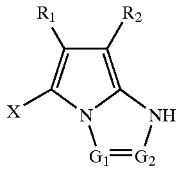

wherein X represents a member selected from the group consisting of a hydrogen atom, halogen atom, alkyloxy group, aryloxy group, acyloxy group, alkylsulfonyloxy and arylsulfonyloxy group, acylamino group, alkylsulfonamide and arylsulfonamide group, alkyloxycarbonyloxy group, aryloxycarbonyloxy group, alkylthio group, arylthio group, heterocyclic thio group, carbamoylamino group, carbamoyloxy group, heterocyclic carbonyloxy group, 5- or 6-membered nitrogen-containing heterocyclic group, imide group; and arylazo group; each of $R_1$ and $R_2$ represents an electron-attracting group having a Hammett's substituent constant p value of not less than 0.20, the sum of the p values of $R_1$ and $R_2$ being not less than 0.65; and each of $G_1$ and $G_2$ represents a nitrogen atom or a substituent represented by formula (II), provided that one of $G_1$ and $G_2$ being a nitrogen atom and the other being a substituent represented by formula (II) below:

(II)

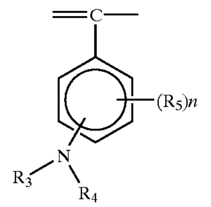

wherein $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a hydrogen atom or a substituent bonded by a carbon atom, $R_3$ and $R_4$ being capable of combining to form a ring; $R_5$ represents a substituent, and n represents an integer of 0 to 4, provided that a group represented by $R_1$, $R_2$, $R_3$, $R_4$, $R_5$, or X may be a divalent group, and thereby the coupler represented by formula (I) may form a polymer, which is a dimer or a higher-order polymer, or may form a homopolymer or a copolymer by combining with a polymeric chain.

2. The pyrrolotriazole compound according to claim 1, wherein the compound represented by formula (I) is represented by formula (III) below:

(III)

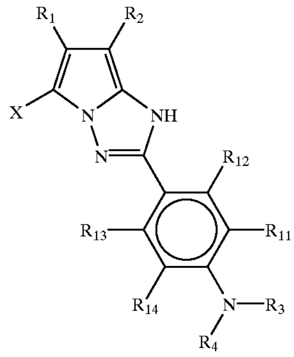

wherein X represents a member selected from the group consisting of a hydrogen atom, halogen atom, 1- to 32-carbon alkyloxy group, 6- to 32-carbon aryloxy group, 1- to 32-carbon alkylthio group, 6- to 32-carbon arylthio group, 2- to 32-carbon heterocyclic thio group, 2- to 32-carbon alkyloxycarbonyloxy group, 7- to 32-carbon aryloxycarbonyloxy group, 1- to 32-carbon carbamoyloxy group, 3- to 32-carbon heterocyclic carbonyloxy group, and 2- to 32-carbon, 5- or 6-membered nitrogen-containing heterocyclic group which bonds to a coupling active position by a nitrogen atom; each of $R_1$ and $R_2$ represents an electron-attracting group having a Hammett's substituent constant p value of not less than 0.20, the sum of the p values of $R_1$ and $R_2$ being not less than 0.65; $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group;

$R_4$ represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, substituted or nonsubstituted acyl group, substituted or nonsubstituted alkyloxycarbonyl group, substituted or nonsubstituted aryloxycarbonyl group and substituted or nonsubstituted carbamoyl group, $R_3$ and $R_4$ being capable of combining to form a ring; and each of $R_{11}$ to $R_{14}$ independently represents a hydrogen atom or a substituent.

3. The pyrrolotriazole compound according to claim 1, wherein the compound represented by formula (I) is represented by formula (IV) below:

(IV)

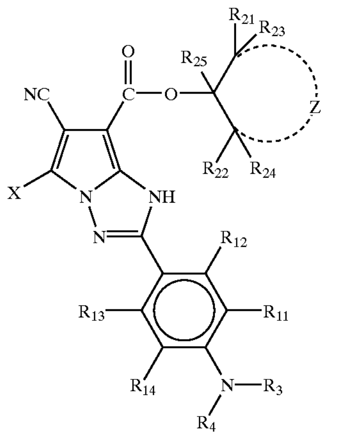

wherein X represents a member selected from the group consisting of a hydrogen atom, halogen atom, substituted or nonsubstituted alkylthio group, substituted or nonsubstituted arylthio group, substituted or nonsubstituted heterocyclic thio group, substituted or nonsubstituted alkyloxycarbonyloxy group, substituted or nonsubstituted aryloxycarbonyloxy group, substituted or nonsubstituted carbamoyloxy group, and substituted or nonsubstituted heterocyclic carbonyloxy group; $R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group; $R_4$ represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group, $R_3$ and $R_4$ being capable of combining to form a ring; $R_{11}$ represents a member selected from the group consisting of a substituted or nonsubstituted acylamino group, substituted or nonsubstituted alkylsulfonylamino group, substituted or nonsubstituted arylsulfonylamino group, and nitro group; $R_{12}$, $R_{13}$, and $R_{14}$ can be the same or different and each represents a member selected from the group consisting of a hydrogen atom, halogen atom, alkyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group; $R_{21}$, $R_{22}$, $R_{23}$, $R_{24}$, and $R_{25}$ can be the same or different and each represents a member selected from the group consisting of a hydrogen atom, substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group; and Z represents a non-metallic atom group required to form a 5- to 8-membered ring, said ring being able to be substituted, be a saturated ring, or have a unsaturated bond.

4. The pyrrolotriazole compound according to claim 1, wherein X represents a member selected from the group consisting of a hydrogen atom, halogen atom, arylthio group, carbamoyloxy group, and heterocyclic carbonyloxy group;

each of $R_1$ and $R_2$ represents a member selected from the group consisting of an acyl group, acyloxy group, carbamoyl group, alkyloxycarbonyl group, aryloxycarbonyl group, cyano group, nitro group, dialkylphosphono group, diarylphosphono group, diarylphosphinyl group, alkylsulfinyl group, arylsulfinyl group, alkylsulfonyl group, arylsulfonyl group, sulfonyloxy group, acylthio group, sulfamoyl group, thiocyanate group, thiocarbonyl group, alkyl halide group, alkoxy halide group, aryloxy halide group, alkylamino halide group, alkylthio halide group, aryl group which is substituted by another electron attracting group having a p value of 0.20 or more, heterocyclic group, halogen atom, azo group, and selenocyanate group;

$R_3$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, substituted or nonsubstituted aryl group, and substituted or nonsubstituted heterocyclic group;

$R_4$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group, $R_3$ and $R_4$ being capable of combining to form a ring; and $R_5$ represents a member selected from the group consisting of an alkyl group, alkenyl group, alkynyl group, cycloalkyl group, cycloalkenyl group, aryl group, heterocyclic group, cyano group, nitro group, acylamino group, anilino group, ureido group, sulfamoylamino group, alkylthio group, arylthio group, alkyloxycarbonylamino group, sulfonamide group (alkylsulfonylamino group and arylsulfonylamino group), carbamoyl group, sulfamoyl group, sulfonyl group, alkyloxycarbonyl group, heterocyclic oxy group, acyloxy group, carbamoyloxy group, aryloxycarbonylamino group, imide group, heterocyclic thio group, sulfinyl group, phosphonyl group, aryloxycarbonyl group, and acyl group.

5. The pyrrolotriazole compound according to claim 2, wherein each of $R_{11}$ to $R_{14}$ independently represents a member selected from the group consisting of a hydrogen atom, halogen atom, alkyl group, alkenyl group, alkynyl group, cycloalkyl group, cycloalkenyl group, aryl group, heterocyclic group, cyano group, hydroxy group, nitro group, carboxy group, sulfo group, amino group, alkyloxy group, aryloxy group, acylamino group, alkylamino group, anilino group, ureido group, sulfamoylamino group, alkylthio group, arylthio group, alkyloxycarbonylamino group, sulfonamide group, carbamoyl group, sulfamoyl group, sulfonyl group, alkyloxycarbonyl group, heterocyclic oxy group, azo group, acyloxy group, carbamoyloxy group, silyloxy group, aryloxycarbonylamino group, imide group, heterocyclic thio group, sulfinyl group, phosphonyl group, aryloxycarbonyl group, and acyl group.

6. The pyrrolotriazole compound according to claim 5, wherein X represents a member selected from the group consisting of a hydrogen atom, halogen atom, arylthio group, carbamoyloxy group, and heterocyclic carbonyloxy group;

each of $R_1$ and $R_2$ represents a member selected from the group consisting of an acyl group, acyloxy group, carbamoyl group, alkyloxycarbonyl group, aryloxycarbonyl group, cyano group, nitro group, dialkylphosphono group, diarylphosphono group, diarylphosphinyl group, alkylsulfinyl group, arylsulfinyl group, alkylsulfonyl group, arylsulfonyl group, sulfonyloxy group, acylthio group, sulfamoyl group, thiocyanate group, thiocarbonyl group, alkyl halide group, alkoxy halide group, aryloxy halide group, alkylamino halide group, alkylthio halide group, aryl group which is substituted by another electron attracting group having a p value of 0.20 or more, heterocyclic group, halogen atom, azo group, and selenocyanate group;

$R_3$ represents a member selected from the group consisting of a 1- to 32-carbon, straight-chain or branched-chain alkyl group, 7- to 32-carbon aralkyl group, 2- to 32-carbon alkenyl group, 2- to 32-carbon alkynyl group, 3- to 32-carbon cycloalkyl group, 3- to 32-carbon cycloalkenyl group, 6- to 36-carbon aryl group, and 5- to 8-membered, 1- to 36-carbon heterocyclic group having a nitrogen atom, oxygen atom, or sulfur atom; and $R_4$ represents a member selected from the group consisting of a substituted or nonsubstituted alkyl group, substituted or nonsubstituted alkenyl group, substituted or nonsubstituted alkynyl group, substituted or nonsubstituted cycloalkyl group, substituted or nonsubstituted cycloalkenyl group, and substituted or nonsubstituted aryl group, $R_3$ and $R_4$ being capable of combining to form a ring.

7. The pyrrolotriazole compound according to claim 3, wherein X is a hydrogen atom; each of $R_{21}$ and $R_{22}$ is t-butyl; each of $R_{23}$, $R_{24}$, and $R_{25}$ is a hydrogen atom; Z forms a cyclohexane ring, and the 4-position of this cyclohexane ring is substituted by a 1- to 8-carbon alkyl group; $R_3$ and $R_4$ form a ring structure; $R_{11}$ is a substituted or nonsubstituted, 1- to 32-carbon alkylsulfonylamino group, substituted or nonsubstituted, 6- to 30-carbon arylsulfonylamino group, or nitro group; and each of $R_{12}$ to $R_{14}$ is a hydrogen atom or a 6- to 30-carbon arylsulfonylamino group having a substituent.

8. The pyrrolotriazole compound according to claim 7, wherein the substituent, which the arylsulfonylamino group has, is a 1- to 32-carbon alkoxy group, 1- to 32-carbon alkyl group, 1- to 32-carbon sulfonylamino group, 1- to 32-carbon acylamino group, or halogen atom.

9. The pyrrolotriazole compound according to claim 7, wherein $R_3$ and $R_4$ form a 6-membered ring bonded by a nitrogen atom.

10. The pyrrolotriazole compound according to claim 9, wherein the 6-membered ring bonded by a nitrogen atom is morpholino, piperadinyl substituted by an acyl group, or piperidino substituted by a carboxyl group.

* * * * *